(12) United States Patent
Robinson et al.

(10) Patent No.: US 7,531,098 B2
(45) Date of Patent: May 12, 2009

(54) INTEGRATED AUTOMATIC BLOOD PROCESSING UNIT

(75) Inventors: Thomas C. Robinson, San Francisco, CA (US); Thomas P. Robinson, Encinitas, CA (US); Richard D'Elia, San Mateo, CA (US); Paul Eibe, Oakland, CA (US); Thomas Sahines, Milpitas, CA (US)

(73) Assignee: Terumo Medical Corporation, Somerset, NJ (US)

( * ) Notice: Subject to any disclaimer, the term of this patent is extended or adjusted under 35 U.S.C. 154(b) by 461 days.

(21) Appl. No.: 11/411,560

(22) Filed: Apr. 26, 2006

(65) Prior Publication Data

US 2006/0226057 A1  Oct. 12, 2006

Related U.S. Application Data

(60) Division of application No. 10/418,490, filed on Apr. 18, 2003, now Pat. No. 7,037,428, which is a continuation-in-part of application No. 10/179,920, filed on Jun. 24, 2002, now Pat. No. 6,890,291.

(60) Provisional application No. 60/374,141, filed on Apr. 19, 2002.

(51) Int. Cl.
*B01D 21/26* (2006.01)

(52) U.S. Cl. ............... 210/787; 210/85; 210/86; 210/87; 210/90; 210/94; 210/97; 210/102; 210/103; 210/109; 210/134; 210/143; 210/194; 210/252; 210/257.1; 210/258; 210/295; 210/313; 210/512.1; 494/1; 494/10; 494/36; 494/37; 494/43; 604/6.09; 604/6.1; 604/6.11; 604/28; 604/408

(58) Field of Classification Search ................. 210/739, 210/741, 745, 746, 767, 787, 788, 789, 790, 210/85, 86, 87, 90, 94, 97, 101, 102, 103, 210/104, 109, 134, 143, 198.1, 194, 252, 210/257.1, 258, 295, 313, 512.1; 494/1, 494/10, 36, 37, 43; 604/4.01, 6.01, 6.02, 604/6.04, 6.09, 6.1, 6.11, 28, 408
See application file for complete search history.

(56) References Cited

U.S. PATENT DOCUMENTS 3,634,228 A * 1/1972 Latham, Jr. ................. 210/636

(Continued)

FOREIGN PATENT DOCUMENTS

EP  0 214 803 A2  8/1986

(Continued)

OTHER PUBLICATIONS

Herschel, L.H. et al., "An automated prototype device to glycerolize red cells at collection," *Transfusion*, 39(10):Supp. 14S (1999).

(Continued)

*Primary Examiner*—John Kim
(74) *Attorney, Agent, or Firm*—Pillsbury Winthrop Shaw Pittman LLP

(57) ABSTRACT

A system for automatically processing blood components is described. The system includes a console, which contains all motors, pumps, sensors, valves and control circuitry, and a unique disposable set that includes a cassette supporting a centrifuge with an improved design, pump interfaces with an improved design, component and solution bags, and tubing. Various processes are implemented using a specific disposable set for each process which allows automatic identification of the process to be performed the console.

17 Claims, 54 Drawing Sheets

U.S. PATENT DOCUMENTS

| | | |
|---|---|---|
| 3,655,123 A | 4/1972 | Judson et al. |
| 3,951,148 A | 4/1976 | Herb |
| 3,957,197 A | 5/1976 | Sartory et al. |
| 3,982,691 A * | 9/1976 | Schlutz ..................... 494/29 |
| 4,007,871 A | 2/1977 | Jones et al. |
| 4,010,894 A | 3/1977 | Kellogg et al. |
| 4,056,224 A | 11/1977 | Lolachi |
| 4,086,924 A | 5/1978 | Latham, Jr. |
| 4,091,989 A | 5/1978 | Schlutz |
| 4,114,802 A | 9/1978 | Brown |
| 4,285,464 A | 8/1981 | Latham, Jr. |
| 4,303,193 A | 12/1981 | Latham, Jr. |
| 4,304,357 A | 12/1981 | Schoendorfer |
| 4,330,080 A | 5/1982 | Mathieu |
| 4,342,420 A | 8/1982 | Rosemeier et al. |
| 4,344,560 A | 8/1982 | Iriguchi et al. |
| 4,356,958 A | 11/1982 | Kolobow et al. |
| 4,379,452 A | 4/1983 | DeVries |
| 4,381,072 A | 4/1983 | Matsumoto et al. |
| 4,386,730 A | 6/1983 | Mulzet |
| 4,387,848 A | 6/1983 | Kellogg et al. |
| 4,416,654 A | 11/1983 | Schoendorfer et al. |
| 4,419,089 A | 12/1983 | Kolobow et al. |
| 4,439,178 A | 3/1984 | Mulzet |
| 4,447,221 A | 5/1984 | Mulzet |
| 4,464,167 A | 8/1984 | Schoendorfer et al. |
| 4,531,932 A | 7/1985 | Luppi et al. |
| 4,636,193 A | 1/1987 | Cullis |
| 4,637,813 A | 1/1987 | DeVries |
| 4,647,279 A | 3/1987 | Mulzet et al. |
| 4,668,214 A | 5/1987 | Reeder |
| 4,680,025 A | 7/1987 | Kruger et al. |
| 4,696,666 A | 9/1987 | Rice, Jr. |
| 4,708,712 A | 11/1987 | Mulzet |
| 4,710,161 A | 12/1987 | Takabayashi et al. |
| 4,734,089 A | 3/1988 | Cullis |
| 4,747,952 A | 5/1988 | Nakano et al. |
| 4,790,807 A | 12/1988 | Neumann et al. |
| 4,806,252 A | 2/1989 | Brown et al. |
| 4,834,890 A | 5/1989 | Brown et al. |
| 4,850,995 A | 7/1989 | Tie et al. |
| 4,897,185 A | 1/1990 | Schuyler et al. |
| 4,940,543 A | 7/1990 | Brown et al. |
| 4,985,153 A | 1/1991 | Kuroda et al. |
| 5,053,127 A | 10/1991 | Schoendorfer et al. |
| 5,076,911 A | 12/1991 | Brown et al. |
| 5,104,526 A | 4/1992 | Brown et al. |
| 5,147,290 A | 9/1992 | Jonsson |
| 5,186,844 A | 2/1993 | Burd et al. |
| 5,217,426 A | 6/1993 | Bacehowski et al. |
| 5,217,427 A | 6/1993 | Cullis |
| 5,217,618 A | 6/1993 | Murakoshi |
| 5,242,384 A | 9/1993 | Robinson et al. |
| 5,273,517 A | 12/1993 | Barone et al. |
| 5,281,342 A | 1/1994 | Biesel et al. |
| 5,298,016 A | 3/1994 | Gordon |
| 5,298,171 A | 3/1994 | Biesel |
| 5,311,908 A | 5/1994 | Barone et al. |
| 5,318,512 A | 6/1994 | Neumann |
| 5,322,620 A | 6/1994 | Brown et al. |
| 5,386,734 A | 2/1995 | Pusinelli |
| 5,387,187 A | 2/1995 | Fell et al. |
| 5,394,732 A | 3/1995 | Johnson et al. |
| 5,403,272 A | 4/1995 | Deniega et al. |
| 5,427,695 A | 6/1995 | Brown |
| 5,437,598 A | 8/1995 | Antwiler |
| 5,437,624 A | 8/1995 | Langley |
| 5,445,506 A | 8/1995 | Afflerbaugh et al. |
| 5,445,593 A | 8/1995 | Biesel et al. |
| 5,462,416 A | 10/1995 | Dennehey et al. |
| 5,478,479 A | 12/1995 | Herrig |
| 5,141,486 A | 1/1996 | Antwiler |
| 5,482,440 A | 1/1996 | Dennehey et al. |
| 5,494,578 A | 2/1996 | Brown et al. |
| 5,494,592 A | 2/1996 | Latham, Jr. et al. |
| 5,501,840 A | 3/1996 | Mantovani et al. |
| 5,514,069 A | 5/1996 | Brown et al. |
| 5,527,472 A | 6/1996 | Bellotti et al. |
| 5,547,453 A | 8/1996 | Di Perna |
| 5,549,834 A | 8/1996 | Brown |
| 5,571,068 A | 11/1996 | Bacehowski et al. |
| 5,573,678 A | 11/1996 | Brown et al. |
| 5,580,465 A | 12/1996 | Pall et al. |
| 5,581,687 A | 12/1996 | Lyle et al. |
| 5,607,579 A | 3/1997 | Latham, Jr. et al. |
| 5,607,830 A | 3/1997 | Biesel et al. |
| 5,614,106 A | 3/1997 | Payrat et al. |
| 5,628,915 A | 5/1997 | Brown et al. |
| 5,632,893 A | 5/1997 | Brown et al. |
| 5,637,082 A | 6/1997 | Pages et al. |
| 5,641,414 A | 6/1997 | Brown |
| 5,649,903 A | 7/1997 | Deniega et al. |
| 5,651,766 A | 7/1997 | Kingsley et al. |
| 5,653,887 A | 8/1997 | Wahl et al. |
| 5,658,240 A | 8/1997 | Urdahl et al. |
| 5,670,060 A | 9/1997 | Matkovich et al. |
| 5,686,238 A | 11/1997 | Martinson et al. |
| 5,693,232 A | 12/1997 | Brown et al. |
| 5,702,357 A | 12/1997 | Bainbridge et al. |
| 5,704,887 A | 1/1998 | Slowik et al. |
| 5,704,888 A | 1/1998 | Hlavinka et al. |
| 5,704,889 A | 1/1998 | Hlavinka et al. |
| 5,712,798 A | 1/1998 | Langley et al. |
| 5,720,716 A | 2/1998 | Blakeslee et al. |
| 5,722,946 A | 3/1998 | Mudloff et al. |
| 5,728,060 A | 3/1998 | Kingsley et al. |
| 5,730,883 A | 3/1998 | Brown |
| 5,733,253 A | 3/1998 | Headley et al. |
| 5,738,644 A | 4/1998 | Holmes et al. |
| 5,738,796 A | 4/1998 | Bormann et al. |
| 5,741,428 A | 4/1998 | Holm |
| 5,746,708 A | 5/1998 | Giesler et al. |
| 5,750,025 A | 5/1998 | Holmes et al. |
| 5,759,147 A | 6/1998 | Bacehowski et al. |
| 5,769,811 A | 6/1998 | Stacey et al. |
| 5,769,839 A | 6/1998 | Carmen et al. |
| 5,779,660 A | 7/1998 | Kingsley et al. |
| 5,783,085 A | 7/1998 | Fischel |
| 5,785,869 A | 7/1998 | Martinson et al. |
| 5,792,038 A | 8/1998 | Hlavinka |
| 5,792,372 A | 8/1998 | Brown et al. |
| 5,795,317 A | 8/1998 | Brierton et al. |
| 5,807,492 A | 9/1998 | Brown et al. |
| 5,817,042 A | 10/1998 | Langley et al. |
| 5,837,150 A | 11/1998 | Langley et al. |
| 5,849,203 A | 12/1998 | Brown et al. |
| 5,853,382 A | 12/1998 | Kingsley et al. |
| 5,865,785 A | 2/1999 | Bischof |
| 5,870,805 A | 2/1999 | Kandler et al. |
| 5,876,321 A | 3/1999 | Hlavinka et al. |
| 5,879,280 A | 3/1999 | Hlavinka et al. |
| 5,882,289 A | 3/1999 | Sakota et al. |
| 5,891,080 A | 4/1999 | Skinkle et al. |
| 5,904,645 A | 5/1999 | Hlavinka |
| 5,906,570 A | 5/1999 | Langley et al. |
| 5,913,768 A | 6/1999 | Langley et al. |
| 5,919,154 A | 7/1999 | Toavs et al. |
| 5,921,950 A | 7/1999 | Toavs et al. |
| 5,941,842 A | 8/1999 | Steele et al. |
| 5,956,023 A | 9/1999 | Lyle et al. |
| 5,961,842 A | 10/1999 | Min et al. |
| 5,980,757 A | 11/1999 | Brown et al. |
| 5,980,760 A | 11/1999 | Min et al. |
| 5,989,177 A | 11/1999 | West et al. |

| | | |
|---|---|---|
| 5,996,634 A | 12/1999 | Dennehey et al. |
| 6,007,509 A | 12/1999 | Kingsley et al. |
| 6,022,306 A | 2/2000 | Dumont et al. |
| 6,027,657 A | 2/2000 | Min et al. |
| 6,051,147 A | 4/2000 | Bischof |
| 6,059,979 A | 5/2000 | Brown |
| 6,068,970 A | 5/2000 | Hosono et al. |
| 6,071,421 A | 6/2000 | Brown |
| 6,071,423 A | 6/2000 | Brown et al. |
| 6,099,491 A | 8/2000 | Headley et al. |
| 6,102,883 A | 8/2000 | Kingsley et al. |
| 6,113,554 A | 9/2000 | Gilcher et al. |
| 6,129,656 A | 10/2000 | Blakeslee et al. |
| 6,135,940 A | 10/2000 | Walters |
| 6,179,801 B1 | 1/2001 | Holmes et al. |
| 6,186,752 B1 | 2/2001 | Deniega et al. |
| 6,196,987 B1 | 3/2001 | Holmes et al. |
| 6,197,579 B1 | 3/2001 | Van Vlasselaer et al. |
| 6,200,287 B1 | 3/2001 | Keller et al. |
| 6,228,017 B1 | 5/2001 | Brown |
| 6,231,537 B1 | 5/2001 | Holmes et al. |
| 6,241,649 B1 | 6/2001 | Zanella et al. |
| 6,254,784 B1 | 7/2001 | Nayak et al. |
| 6,270,673 B1 | 8/2001 | Belt et al. |
| 6,277,060 B1 | 8/2001 | Neumann |
| 6,280,375 B1 | 8/2001 | Meisberger et al. |
| 6,280,406 B1 | 8/2001 | Dolecek et al. |
| 6,309,606 B1 | 10/2001 | Sitar |
| 6,315,707 B1 | 11/2001 | Smith et al. |
| 6,322,488 B1 | 11/2001 | Westberg et al. |
| 6,325,775 B1 | 12/2001 | Thom et al. |
| 6,334,842 B1 | 1/2002 | Hlavinka et al. |
| 6,344,020 B1 | 2/2002 | Reitz et al. |
| 6,348,156 B1 | 2/2002 | Vishnoi et al. |
| 6,379,322 B1 | 4/2002 | Kingsley et al. |
| 6,387,263 B1 | 5/2002 | Bhaskar et al. |
| 6,409,696 B1 | 6/2002 | Toavs et al. |
| 6,419,822 B2 | 7/2002 | Muller et al. |
| 6,440,372 B1 | 8/2002 | Pages |
| 6,451,203 B2 | 9/2002 | Brown |
| 6,464,624 B2 | 10/2002 | Pages |
| 6,475,175 B1 | 11/2002 | Rivera et al. |
| 6,481,980 B1 | 11/2002 | Vandlik et al. |
| 6,524,231 B1 | 2/2003 | Westberg et al. |
| 7,008,393 B2 * | 3/2006 | Robinson et al. ............ 604/6.01 |
| 2001/0000185 A1 | 4/2001 | Keller et al. |
| 2001/0037078 A1 | 11/2001 | Lynn et al. |
| 2002/0028155 A1 | 3/2002 | Dolecek et al. |
| 2002/0032398 A1 | 3/2002 | Steele et al. |
| 2002/0033370 A1 | 3/2002 | Bainbridge et al. |
| 2002/0062100 A1 | 5/2002 | Pierce et al. |
| 2002/0077241 A1 | 6/2002 | Odak et al. |
| 2002/0090319 A1 | 7/2002 | Vandlik et al. |
| 2002/0099319 A1 | 7/2002 | Saito et al. |
| 2002/0128582 A1 | 9/2002 | Farrell et al. |
| 2002/0128583 A1 | 9/2002 | Min et al. |
| 2002/0128584 A1 | 9/2002 | Brown et al. |
| 2002/0131891 A1 | 9/2002 | Smith et al. |
| 2002/0142909 A1 | 10/2002 | Sakota |
| 2003/0106861 A1 | 6/2003 | Gibbs et al. |

FOREIGN PATENT DOCUMENTS

| | | |
|---|---|---|
| EP | 0987039 A2 | 3/2000 |
| GB | 1 451 859 | 12/1974 |
| GB | 1 509 667 | 10/1976 |
| GB | 1 511 819 | 10/1976 |
| WO | WO 88/05691 | 8/1988 |
| WO | WO 89/00084 | 1/1989 |
| WO | WO 93/12888 | 7/1993 |
| WO | WO 94/08691 | 4/1994 |
| WO | WO 98/22165 | 5/1998 |
| WO | 00/23140 | 4/2000 |

OTHER PUBLICATIONS

Valeri, R.C. et al., "A multicenter study of in vitro and in vivo values in human RBCs frozen with 40-percent (wt/vol) glycerol and stored after deglycerolization for 15 days at 4oC in AS-3: assessment of RBC processing in the ACP 215," *Transfusion*, 41:933-39 (2001).

* cited by examiner

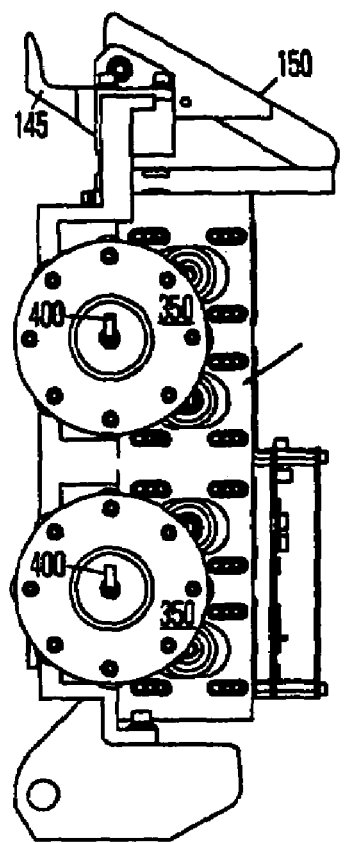
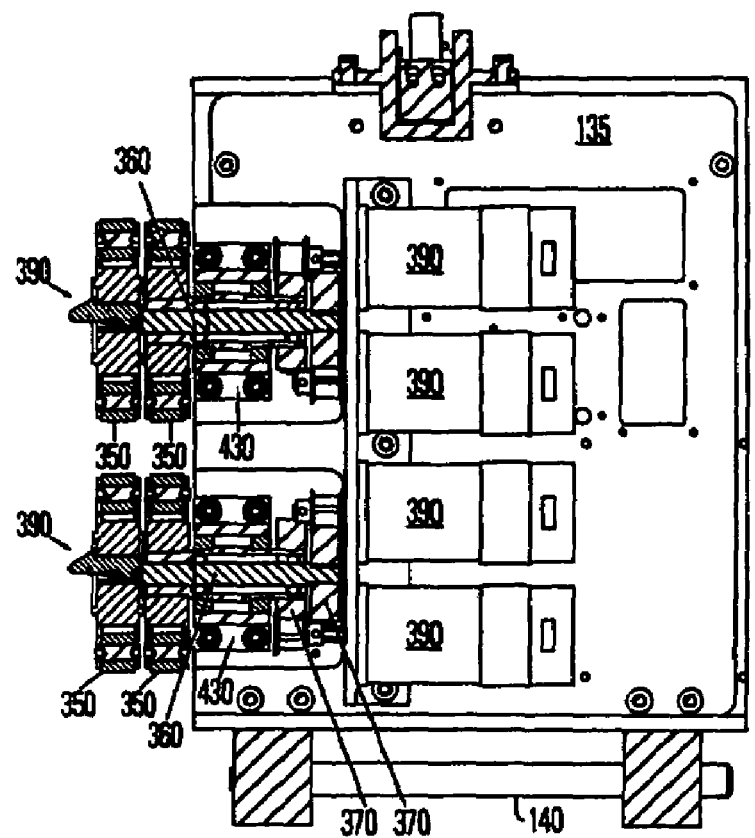
FIG. 9A  FIG. 9B

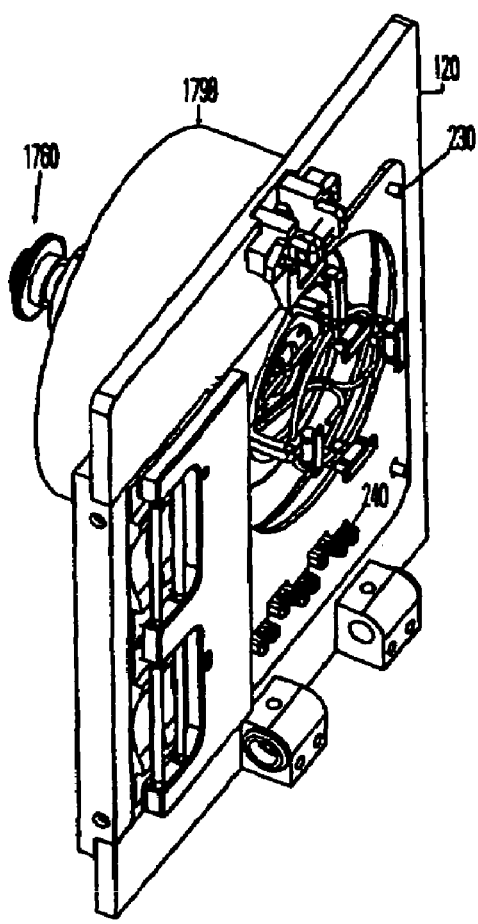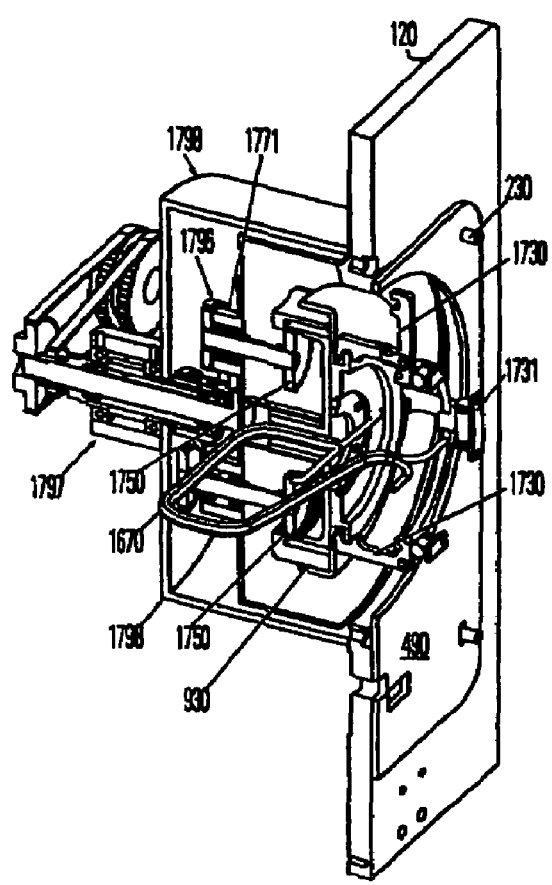
FIG. 28A  FIG. 28B

INTEGRATED AUTOMATIC BLOOD PROCESSING UNIT

RELATED APPLICATIONS

This application claims the benefit of priority under 35 U.S.C. § 121 as a divisional application of U.S. patent application Ser. No. 10/418,490, filed Apr. 18, 2003, entitled "Integrated Automated Blood Processing Unit" and issued as U.S. Pat. No. 7,037,428, which is a continuation-in-part of U.S. patent application Ser. No. 10/179,920, filed Jun. 24, 2002, entitled "Integrated Automatic Blood Collection and Processing Unit" and issued as U.S. Pat. No. 6,890,291, which claims the benefit of priority under 35 U.S.C. § 110 of provisional U.S. Patent Application Ser. No. 60/374,141, filed Apr. 19, 2002, entitled "Integrated Blood Collection and Processing Unit," the contents of each of which are hereby incorporated by reference.

FIELD OF THE INVENTION

This invention relates generally to devices and methods for the automated processing of blood or blood components already collected from a donor or patient.

BACKGROUND OF THE INVENTION

Conventional methods and equipment for preserving red blood cells (RBCs) in the frozen state have been available for many years. The U.S. military has stockpiled several thousand units of frozen group O RBCs for emergency use and may expand these reserves. The civilian blood bank uses for frozen blood include the long-term storage of rare blood types and the storage of RBCs by donors for anticipated future elective surgery. Current standard methods for preservation of RBCs by glycerolizing and deglycerolizing are in use by the military and civilian blood banks (e.g., the American Red Cross and the Naval Blood Research Laboratory Standard Operating Procedures).

In general, the steps involved in the conventional glycerolization/deglycerolization process are as follows: (1) whole blood collection from a donor (e.g., using an anticoagulant); (2) preparation of RBCs from whole blood by removal of plasma (RBCs may be separated, concentrated and stored in additive solution such as AS-1 or AS-3); (3) addition of glycerol cryopreservative to the RBCs prior to freezing; (4) freezing of the glycerolized RBCs for long-term storage (up to about 10 years); and (5) thawing and deglycerolizing of the RBCs (up to about 24 hours of refrigerated storage after deglycerolization, and before centrifugation and administration).

At present, RBCs are glycerolized using a manual procedure involving a bag shaker, centrifuge and plasma extractor (see, e.g., the American Red Cross and the Naval Blood Research Laboratory Standard Operating Procedures). To deglycerolize RBCs, a manual procedure is also used (see, e.g., the Naval Blood Research Laboratory Standard Operating Procedures) involving a centrifugal cell washer (e.g., Model 115; available from Haemonetics Corp., Braintree, Mass.). The Haemonetics system requires one, nearly full-time user to produce about one unit per hour of deglycerolized RBCs. The Haemonetics centrifugal system is not regarded as closed and sterile because it has a rotating centrifuge bowl seal that is open to room air. Therefore, the deglycerolized RBC product from this system must be used within 24 hours or discarded. An additional centrifugation step may be required just before RBC administration to a patient to concentrate the RBCs and remove free plasma hemoglobin.

There is a need in the art for a device that can provide automatic, rapid, sterile, low-cost glycerolization and deglycerolization and long-term storage of deglycerolized RBCs for both military and commercial applications. Such a device would greatly increase the practicality and usefulness of frozen RBCs.

Additionally, current methods for intra-operative autotransfusion utilize a centrifuge to process blood in batches. The methods and applications involve processes which are automatic (e.g., the processing of a full centrifuge bowl), while other processes are manual (e.g., the filling of the bowl and the processing of a less than full bowl). Additionally, the processing parameters for a partially-full centrifuge bowl must be manually set if substantial saline dilution and inadequate waste removal are to be avoided. Conventional, disposable autotransfusion sets are also quite expensive, since most current systems use batch processing of blood in relatively large centrifuge bowls. System set-up is also burdensome, and takes about five minutes. Finally, a trained perfusionist is usually required to operate a conventional autotransfusion system in open heart surgery, when a heart-lung bypass is being used. A technician operates the system for vascular surgery or orthopedic surgery, also adding to the cost of the procedure.

There is therefore a need in the art for a fully automatic, safe, easy to set up and use intra-operative autotransfusion system. Such an apparatus may allow a nurse or anesthesiologist to set up and monitor the system operation during use, saving substantial time and cost.

SUMMARY OF THE INVENTION

The present invention includes a console or electromechanical instrument that may be used to perform several different blood processing procedures. The console is a small, compact apparatus that has the various actuation pumps, valves, pressure-sensing transducers, ultrasonic detectors and other devices needed to implement the process using a closed, sterile disposable set. The invention further includes different disposable sets for each process that is specifically designed to implement that process and to contain all associated blood and fluids. As many functions and devices as possible are placed in the console, allowing simplification and reduction in size of the disposable set.

The disposable system includes a cassette to integrate, locate, and support all disposable set components that interact with the console actuation and sensing components. The disposable set components interact automatically with their interactive console components without significant influence by or dependence on the user.

The console uses microprocessor-based electronics and software to select and control a variety of different processes. The console may identify the cassette installed in it by reading a bar code on the cassette. The microprocessor may then initiate the process appropriate for that cassette, with user verification. Automated data collection by the console plus bar code scanning by the user eliminates manual entries and allows error-free data to be provided to a blood center computer.

Other features of the invention include a low-cost manifold as part of the disposable set that contains the actuation and sensing components, and a simple, low-cost, continuous-flow centrifuge assembly with unique features that increase its efficiency. Additionally, in particular embodiments of the present invention, additional components such as optical sensors, a free plasma hemoglobin sensor and a recirculation bag shaker may be included to implement or enhance the function of the present invention.

BRIEF DESCRIPTION OF THE DRAWINGS

FIGS. 9A and 9B are views of a door showing the attachment of rotors, in accordance with an embodiment of the present invention.

FIGS. 28A and 28B are views of a continuous centrifuge disk with an umbilical with a cassette mounted to the front panel of a console, in accordance with an embodiment of the present invention.

DETAILED DESCRIPTION OF THE INVENTION

Console

Figure 1:
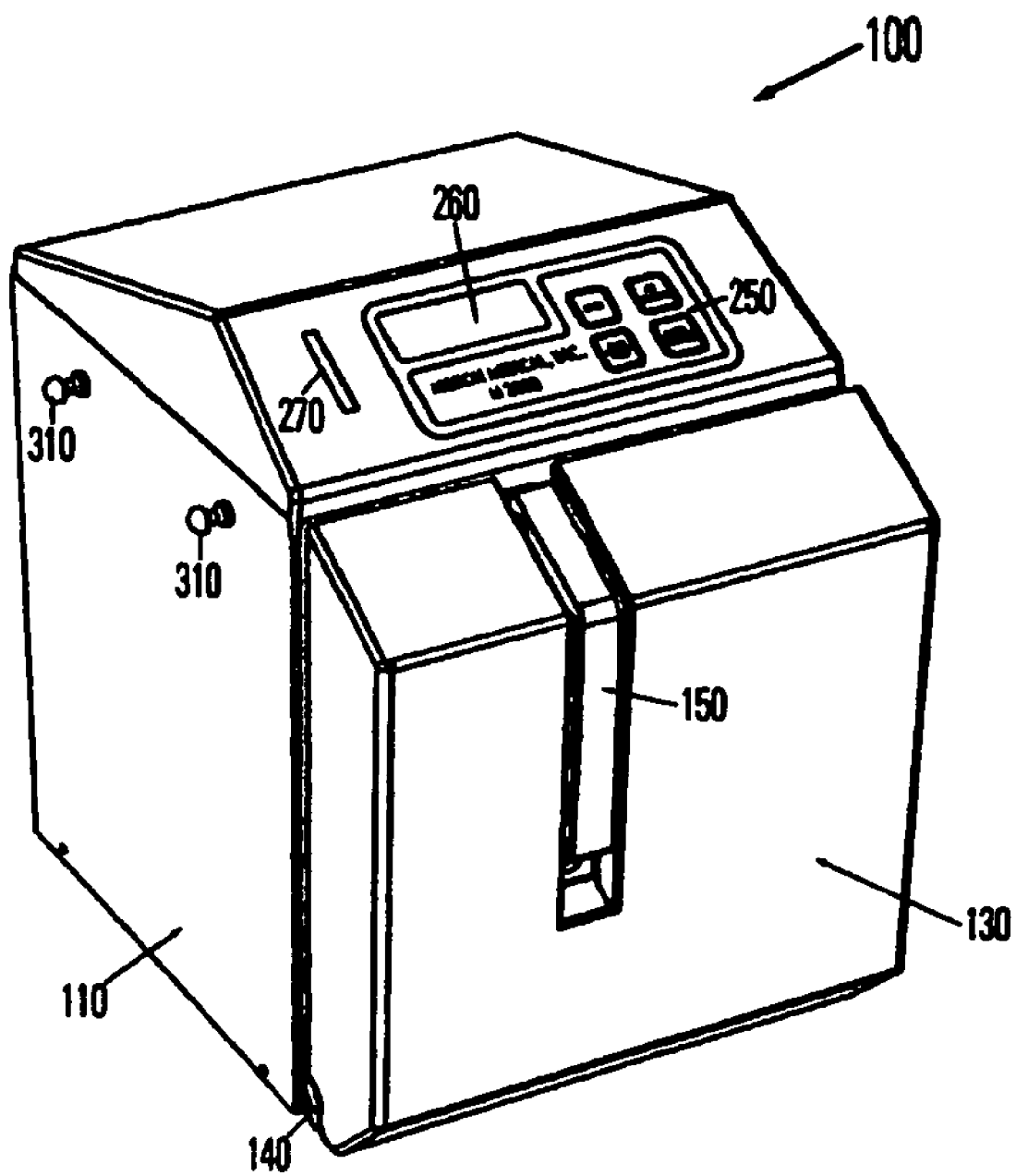
FIG. 1 is a perspective view of a console, in accordance with an embodiment of the present invention.
Figure 2:
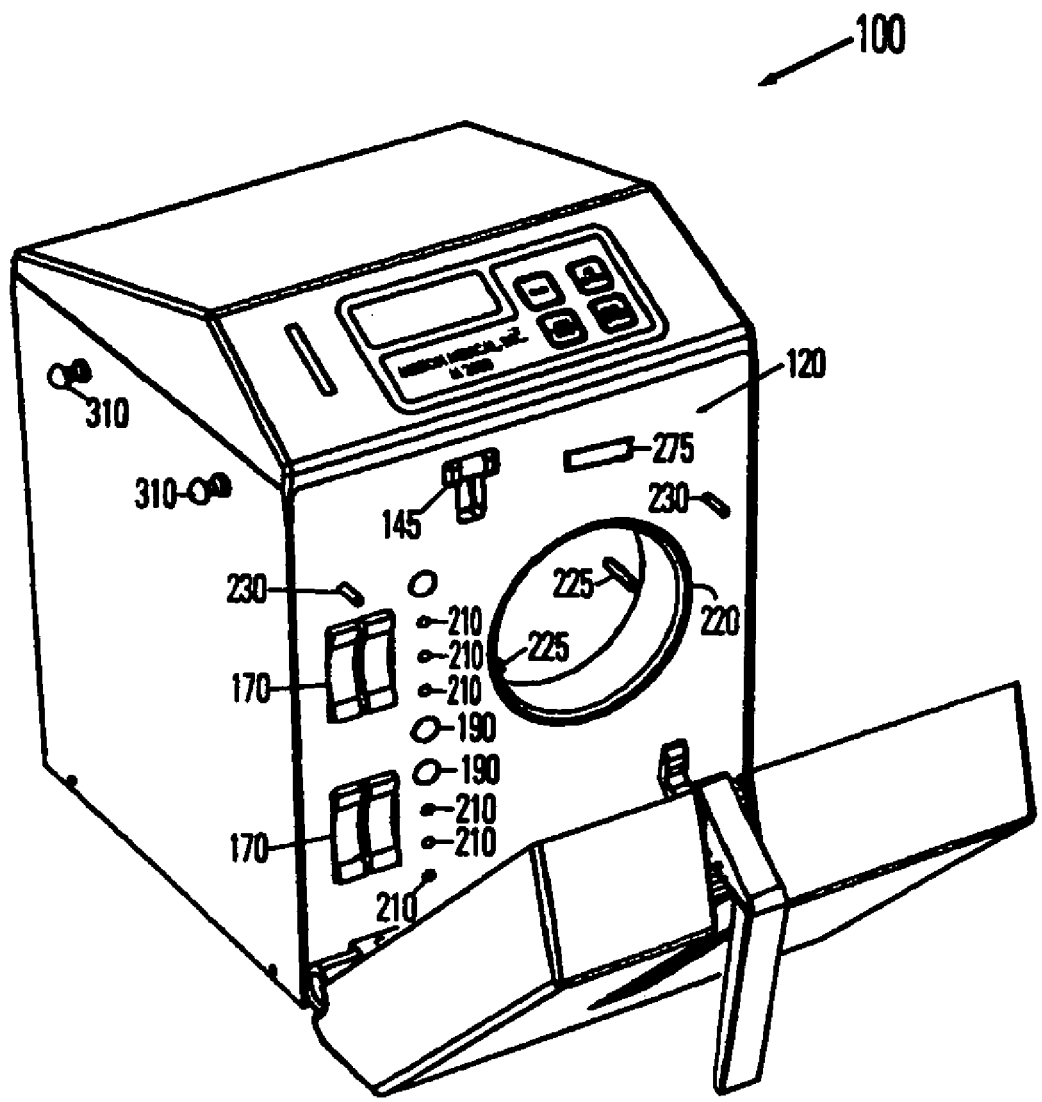
FIG. 2 is a perspective view of a console with the door open, in accordance with an embodiment of the present invention.
Figure 3:
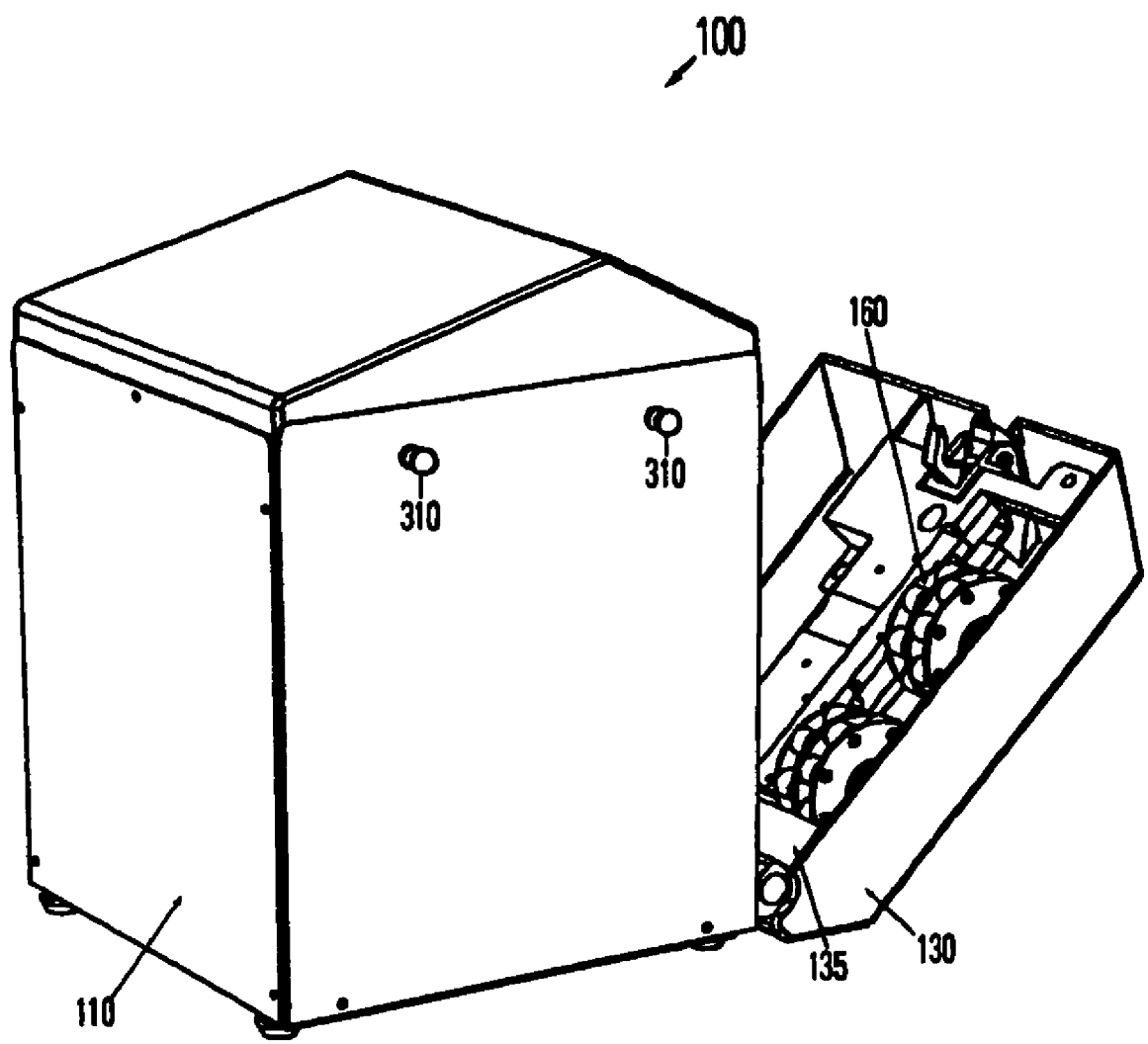
FIG. 3 is a perspective view of a console from the rear showing an interior of the open console door, in accordance with an embodiment of the present invention.
Figure 4:
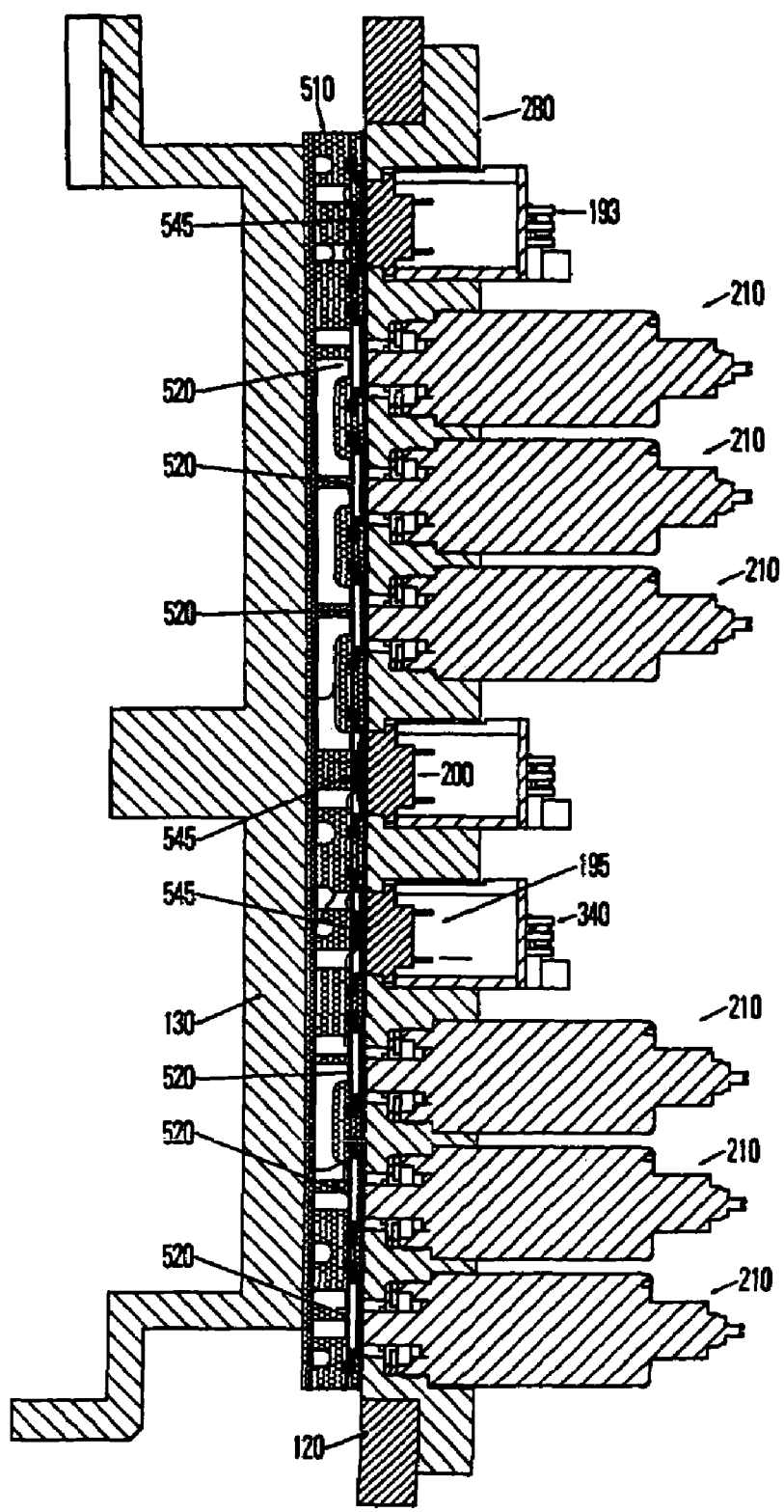
FIG. 4 is a cutaway view of a valve plate assembly, in accordance with an embodiment of the present invention.
Figure 21A:
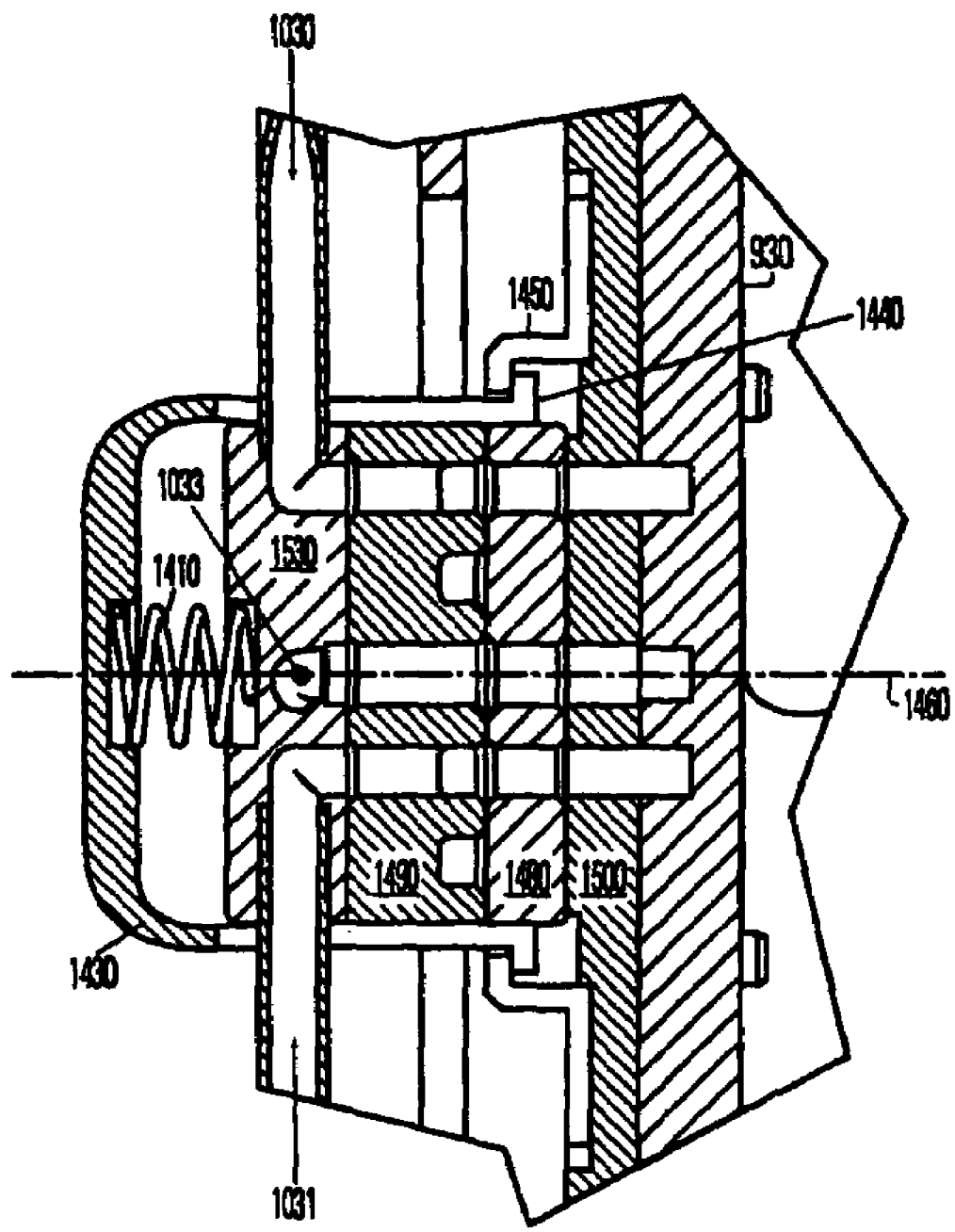
FIGS. 21A and 21B depict a conceptual design and operation of a continuous flow centrifuge that uses a face seal, in accordance with an embodiment of the present invention.
Figure 21B:
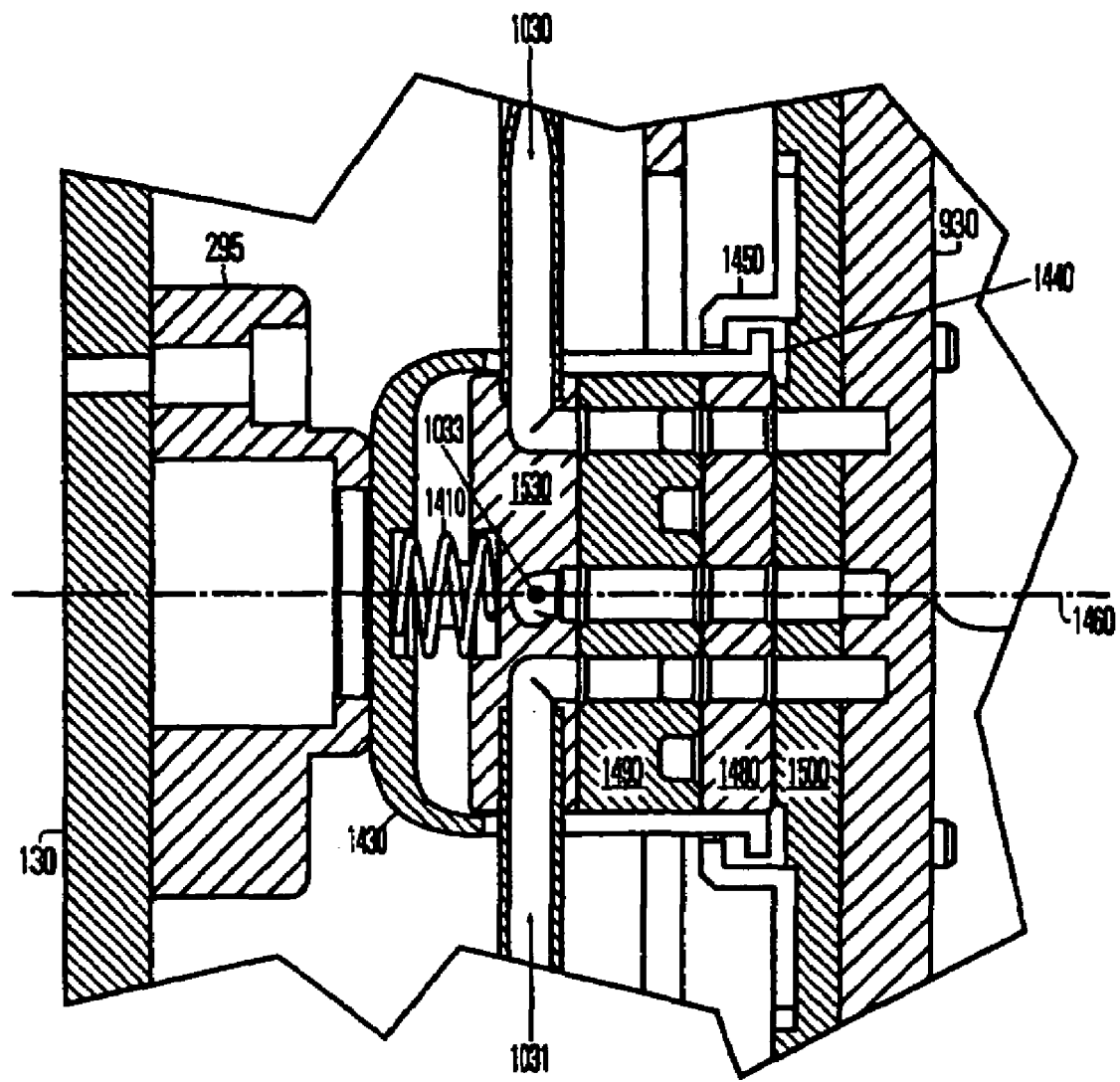
Figure 23:
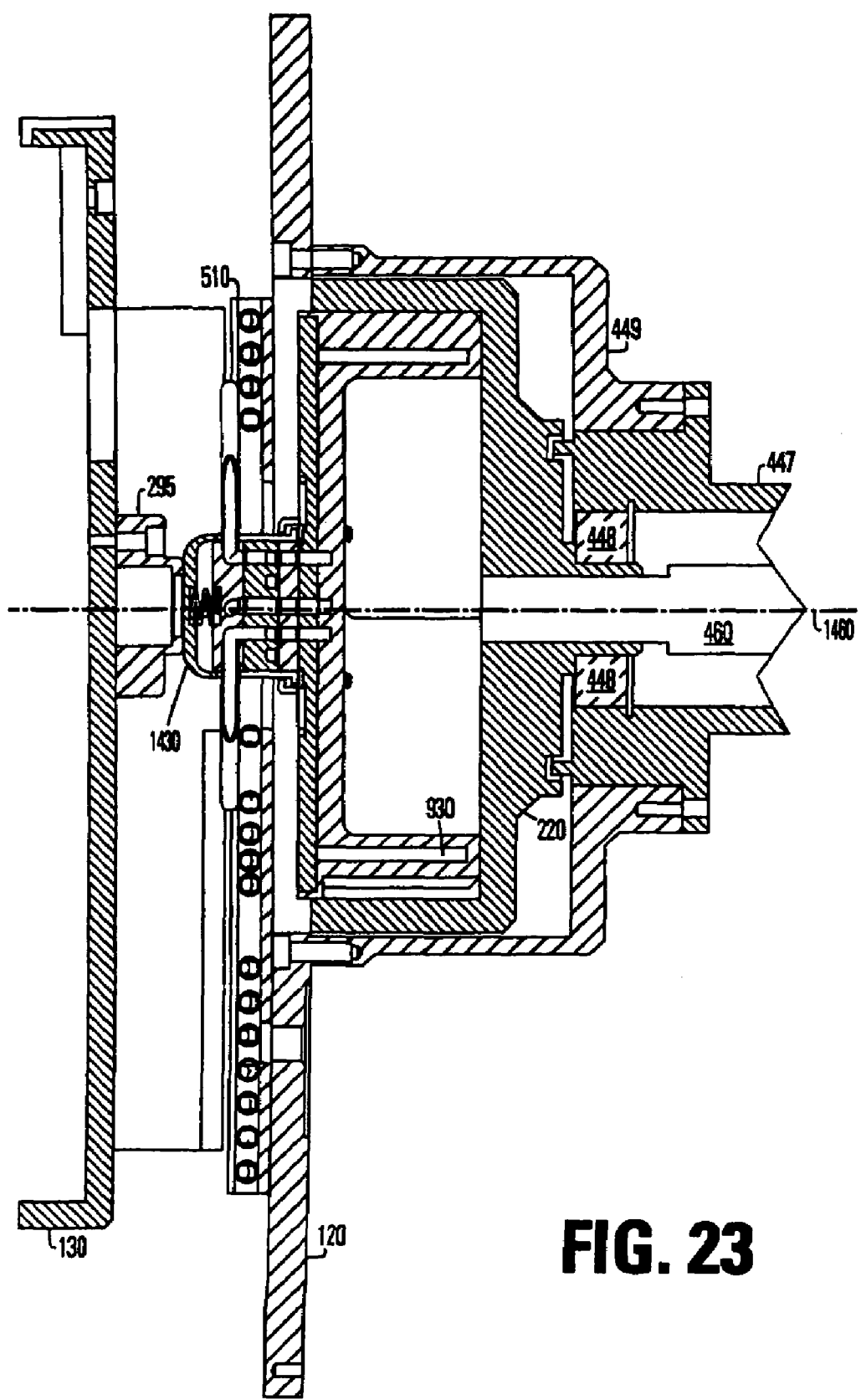
FIG. 23 depicts a continuous flow centrifuge that uses a face seal as mounted for operation in a centrifuge cup in a console, in accordance with an embodiment of the present invention.

With reference to FIGS. 1-3, the system includes a console 100, having a console body 110 enclosing electronic, electromechanical and mechanical components. A console door 130 is connected to the front panel 120 of the console body 110 using a hinge 140 along the front horizontal bottom of the front panel 120. The door 130 may also include a door plunger 295 (shown in FIGS. 21B and 23), which interacts with certain designs of a centrifuge element on the disposable set as further described below. A latch 145 secures and positions the console door to the front panel 120 at the top and may be operated through the use of a handle 150 on the door. Hangers 310 on the outside of the console 100 may be used to hold solution and blood product bags 580, 590 (which are part of a disposable set 480 illustratively depicted in FIGS. 15 and 16). Four roller pumps 160 and their drive mechanisms are shown as mounted on the inside of the door 130; although different numbers of roller pumps 160 and their drive mechanisms may be included in alternate embodiments of the present invention. Power may be provided to the system from alternating current sources and/or direct current sources such as batteries (not shown) to allow for portability.

Figure 15:
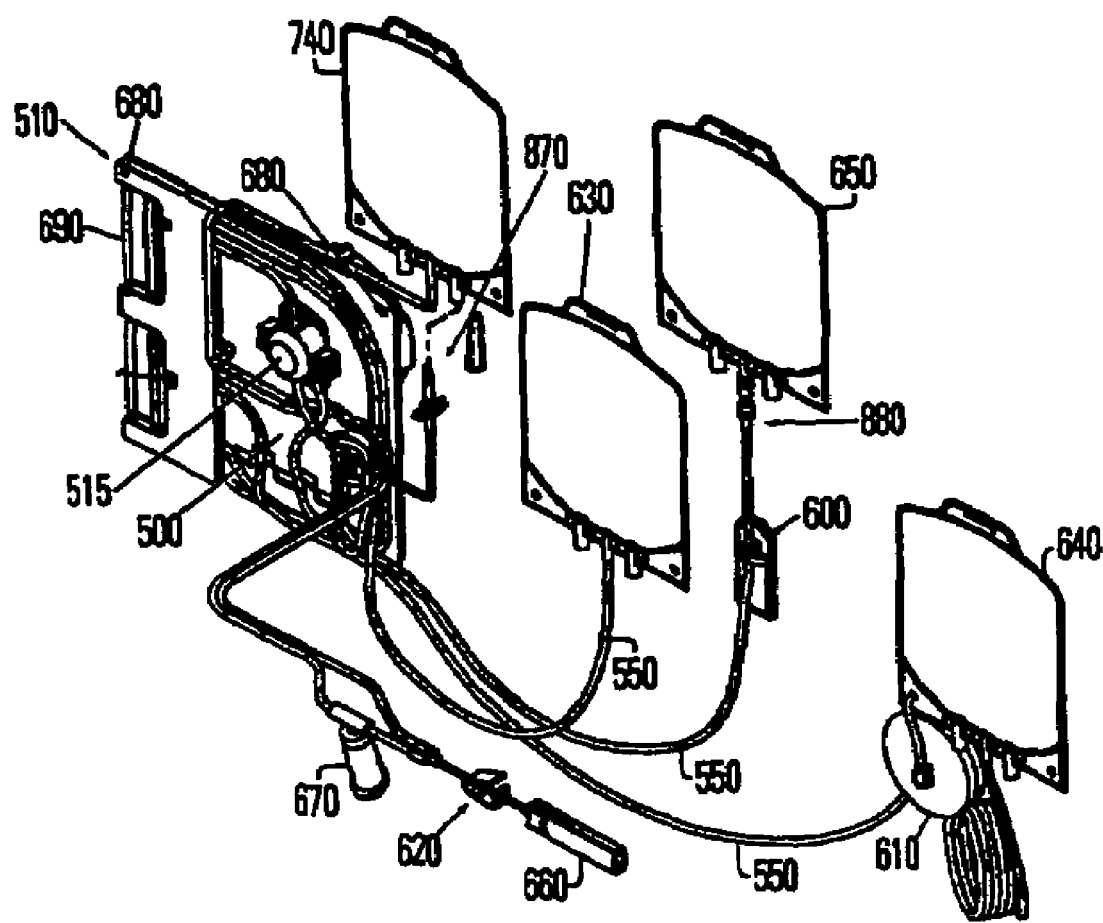
FIG. 15 is a second view of a disposable set, in accordance with an embodiment of the present invention.
Figure 16:
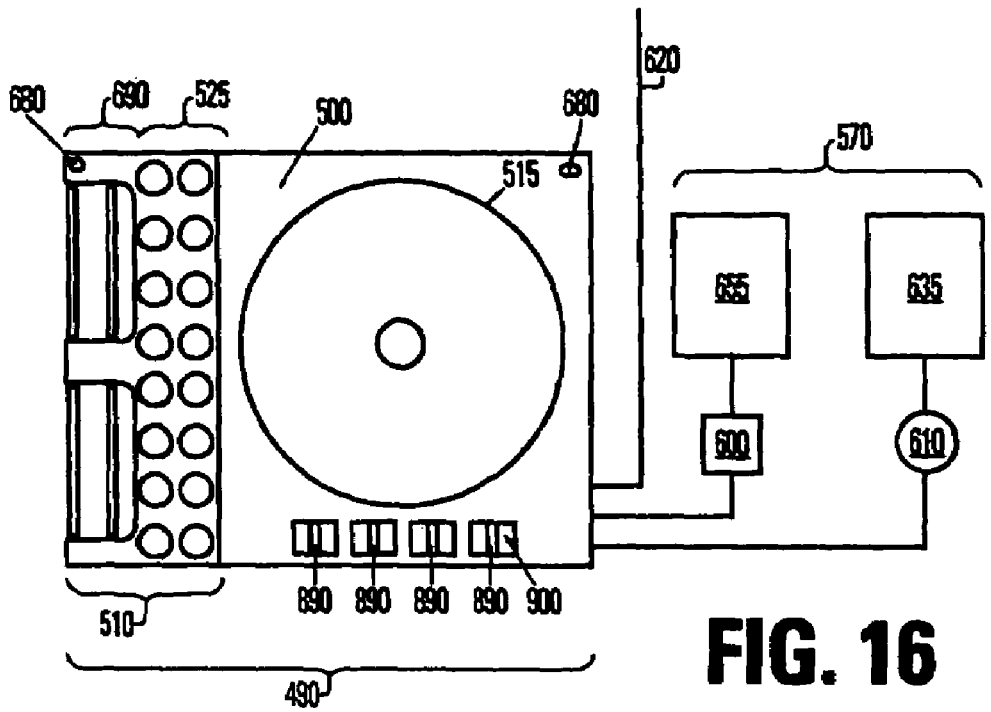
FIG. 16 is a conceptual view of a cassette, in accordance with an embodiment of the present invention.

With reference to FIGS. 2, 4, 5 and 6 the substantially vertical front panel 120 of the console locates and positions roller pump tracks 170, pressure transducers 190, valves (which may be solenoid valve actuators 210, as shown), a centrifuge drive cup 220, ultrasonic sensors 240 and pins 230 (from which to hang a disposable cassette 490, which is further described below in connection with FIGS. 15 and 16). The valve actuators 210 and positive pressure transducers 193, 195, and negative pressure transducer 200 are mounted to a valve plate 280 that is part of and attached to the console front panel 120. Valve actuators 210, including a washer 320 and seal 330, are mounted on the valve plate 280 and front panel 120 so as to be opposite valve components 520 in the cassette 490 of the disposable set 480.

Placement of the roller pump and drive mechanisms on the door with valves and sensors in the console body may allow for a more compact cassette design as the roller pump and drive mechanisms do not compete for space on the console front panel with the valves, sensors and other elements. However, as alternatives to the design shown and described, the roller pumps and drive mechanisms may be placed in the console on the front panel 120, and/or the valves 210 and pressure transducers 190 and/or other components may be placed on the interior of the door, with appropriate modifications to the design of the disposable set.

Figure 6:
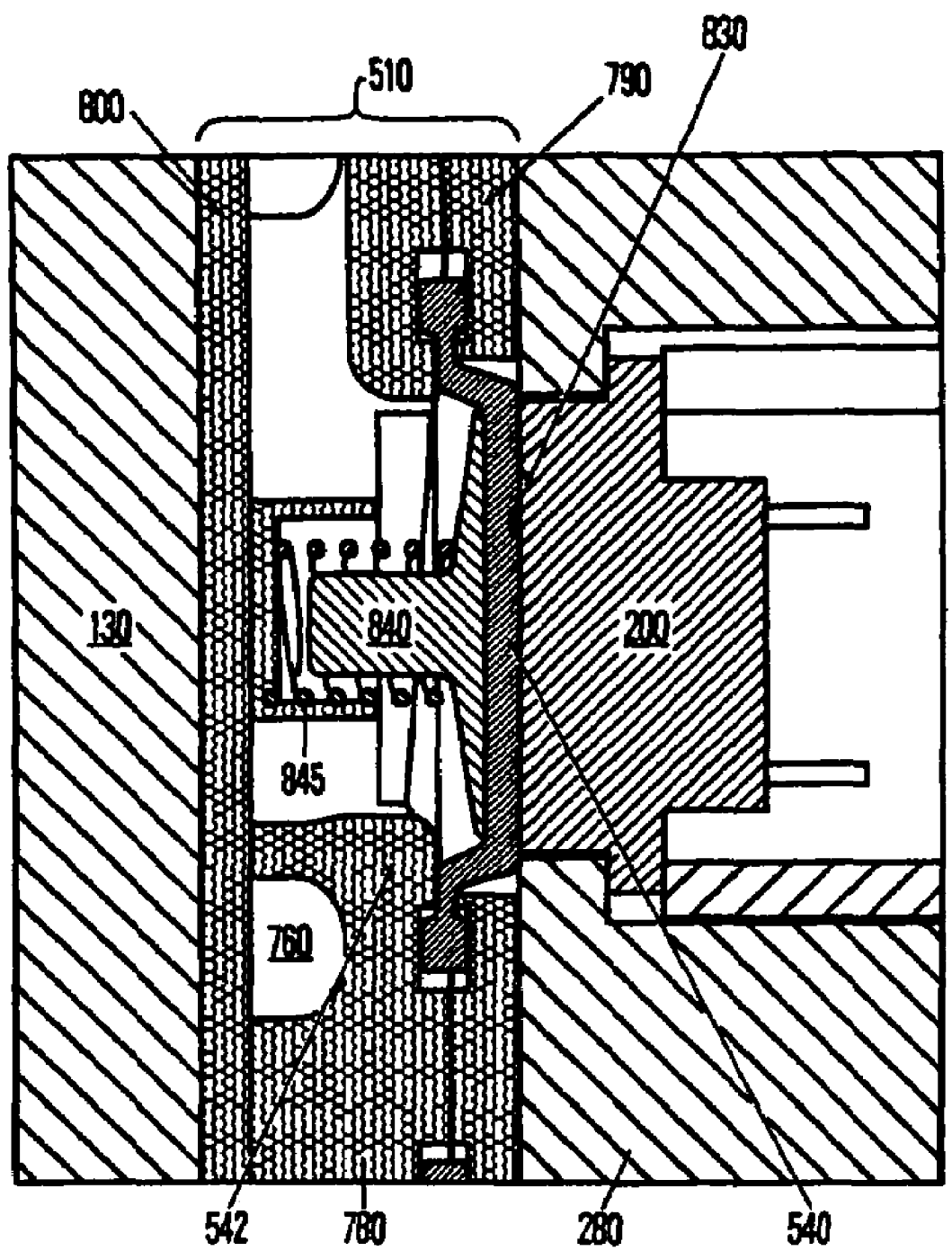
FIG. 6 depicts a negative pressure sensing transducer and associated pressure component, in accordance with an embodiment of the present invention.
Figure 8:
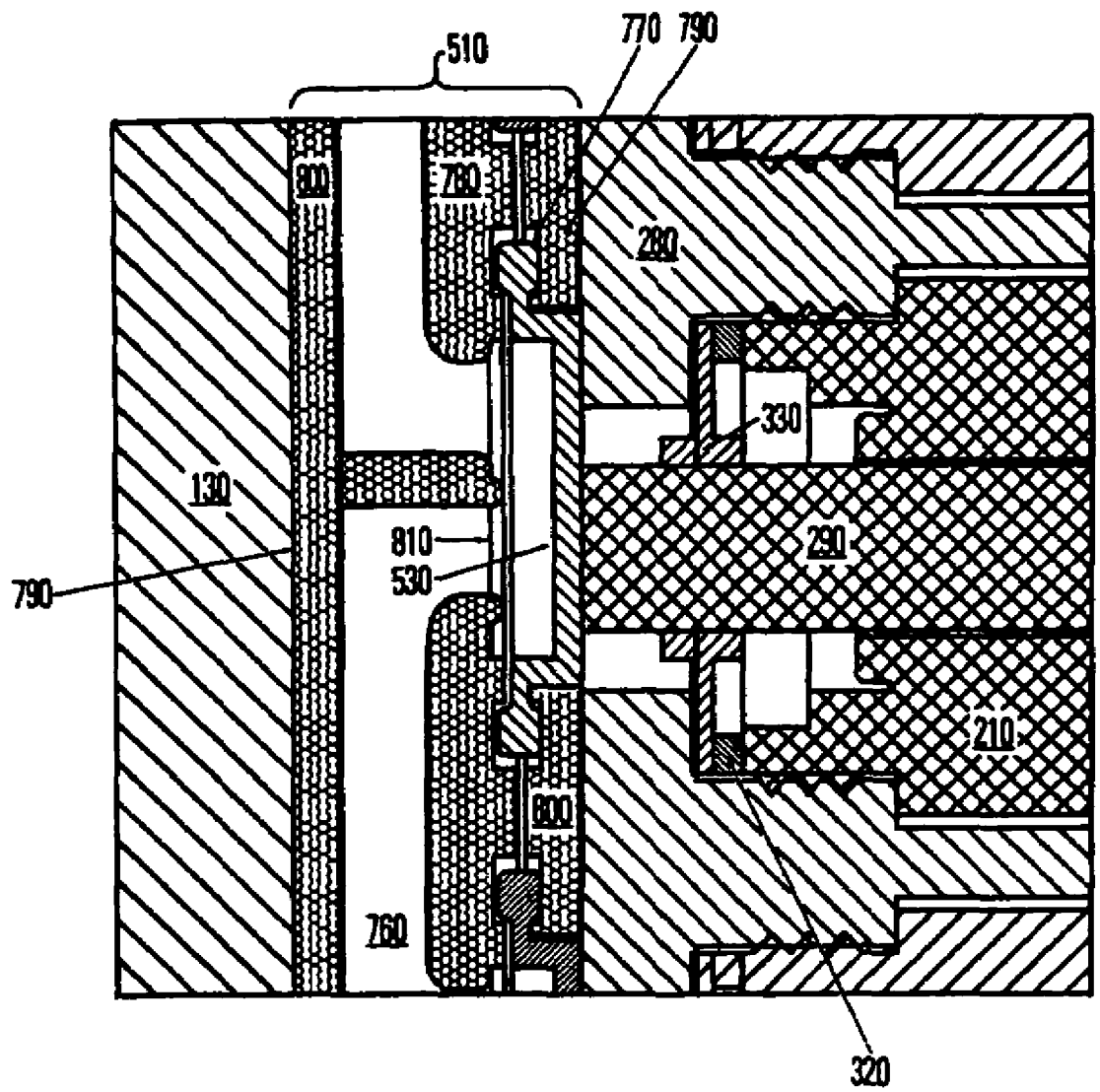
FIG. 8 depicts a detailed view of a valve actuator and valve component, in accordance with an embodiment of the present invention.

Each valve actuator 210, shown in detail in FIG. 8, has a solenoid-operated plunger that moves the valve diaphragm 530 of a disposable valve component 520 to open or occlude a fluid path orifice. The valve actuator 210 shown maybe biased closed by a spring (not shown). A low power level would be needed to keep the valve in an open position, as shown in FIG. 6. The spring-loaded feature is a fail-safe advantage; ensuring that no fluid flow can occur with a system or power failure. The motion of the plunger may be independently monitored with a Hall effect or optical sensor (not shown) to provide confirmation of proper valve function and a warning of solenoid failure.

With reference to FIGS. 4-7 the pressure transducers 190, both positive and negative 193, 195, 200, may be flat-faced standard devices that couple directly to the pressure diaphragm 540 on pressure measurement components 545 in the cassette. Negative pressure is sensed as shown in FIG. 10, as the diaphragm 540 is deformed. Positive pressure is sensed as shown in FIG. 11, when the diaphragm 540 is not deformed.

The console front panel also includes ultrasonic sensors with interfacing fingers mounted in the door. The operation of these devices is described below in connection with the cassette.

Figure 10A:
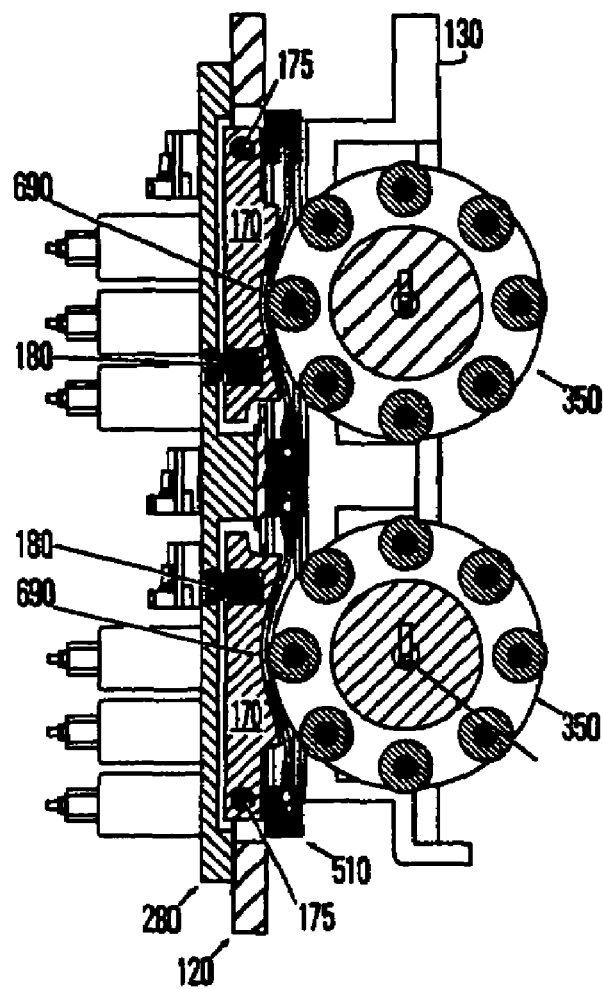
FIGS. 10A and 10B are views of pump rotors, manifold pump tubing and rotor tracks, in accordance with an embodiment of the present invention.
Figure 10B:
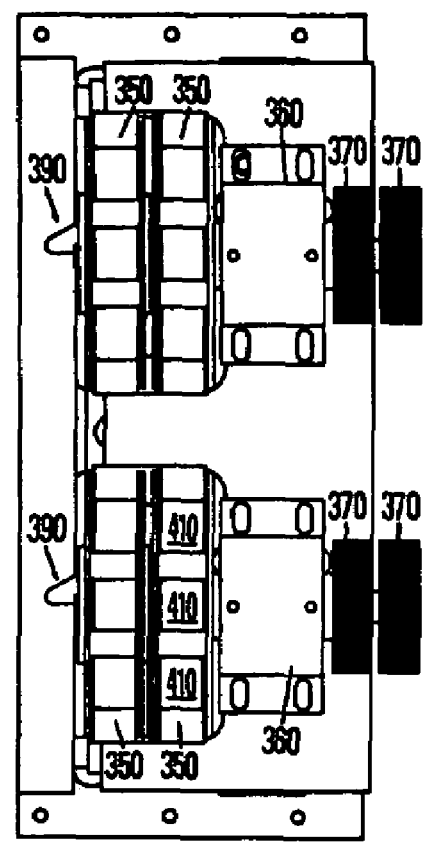
Figure 11:
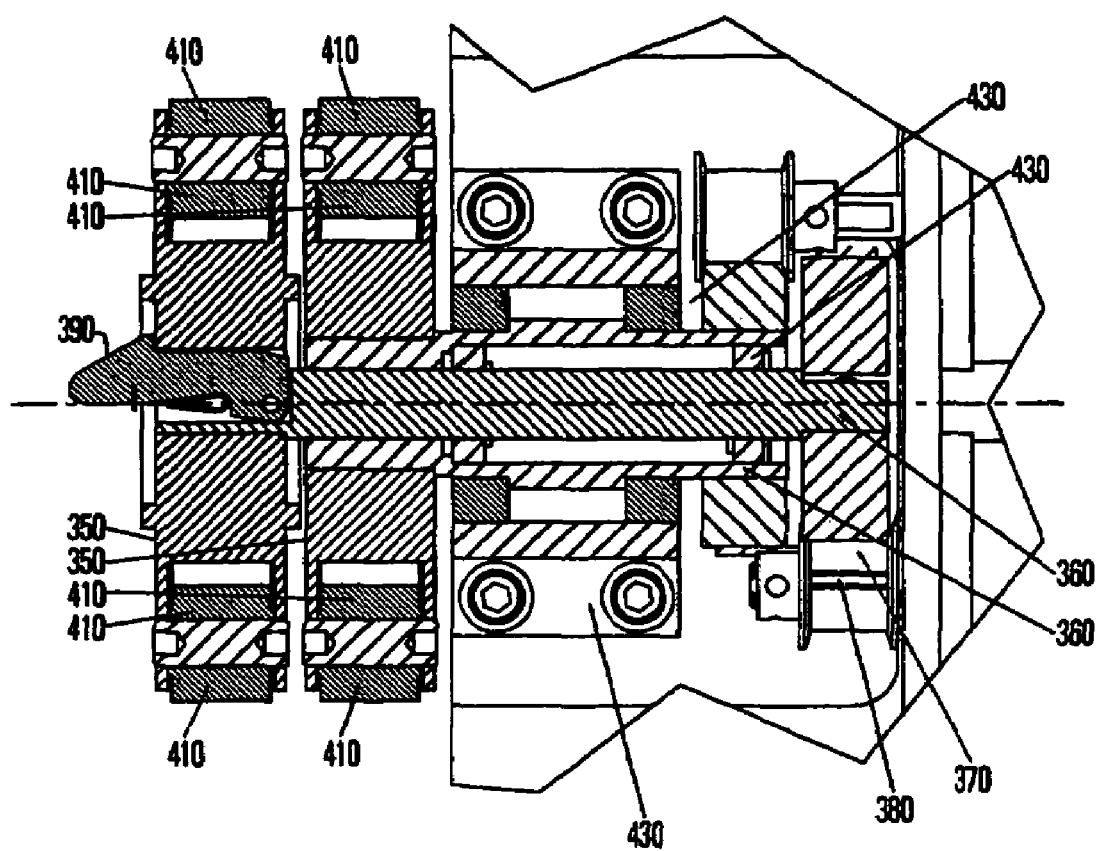
FIG. 11 is a cutaway of electric motors and rotors, in accordance with an embodiment of the present invention.

With reference to FIGS. 9-11, the roller pump and drive mechanism 160 include a number of components. Two roller pump rotors 350 are mounted on concentric shafts 360, supported by bearings 420 within bearing blocks 430, and driven, through belt drives 370, including sprockets 380, from two motors 390, which may be brushless D.C. motors, on a mounting bracket 440 attached to the door 130. The rotors 350 may be designed to be easily removed from the shafts 360 for cleaning by using a mechanism such as a spring-loaded key 400 that is manually activated. Two such assemblies are mounted in the console door. Four independent tracks 170 are mounted to the console front panel 120. These tracks 170 are spring-loaded 180 against roller pump tubing sections 690 which are located between the tracks 170 and rotors 350 when the cassette is mounted on the console 100. In alternate embodiments, different numbers of these components may be included in the system of the present invention.

Each rotor has six to eight rollers 410 equally spaced on its periphery. The small spacing between rollers 410 and the relatively large rotor diameter allow a short track length and short tubing segment on the disposable. This tubing segment is deformed into a short, shallow arc by the rotor and track. As the rotor turns during operation of the system, the rollers 410 force the movement of any liquid, blood, for example, contained in the tubing. Short pump tube segments are desirable in order to minimize overall manifold 510 and cassette size and cost. Additionally, the combination of features allows for a cassette design that automatically places the appropriate pump tube segments in operable connection with the correct pumps and tracks when the cassette is mounted on the front panel and the door is close, thus eliminating the need for an operator to make such connections and the potential for error.

With reference to FIGS. 2, 12, 13 and 23, a centrifuge drive cup 220 is located in the console front panel 120 in order to accept and support a continuous flow centrifuge (CFC) disk 930 on the disposable, which is further described below. The drive cup 220 may have a shield 450 around it inside the console 100. The drive cup 220 is supported on a centrifuge drive shaft 460, which has bearings 448 spaced at each end, with a stationary housing 449 and motor mount 447 supporting these bearings 448. A shield (not shown) may optionally be attached to that portion of the back of the front panel 120 to which the stationary housing 449 is bolted. This achieves a leak-tight assembly preventing fluids from entering the console 100. As one alternative, the drive cup 220 may optionally include locking ears 222 and associated stop pins 223 for locking the centrifuge into the cup 220. As another alternative element in the design, pins 225 may extend from the bottom of the cup to interface with holes 226 in the centrifuge so as to hold the centrifuge 515 in place in the cup and correctly orient the cup and CFC disk 930. As yet another alternative, a slot 227 on one side of the drive cup accepts a tab 228 on the centrifuge, to further hold the centrifuge in place in the cup during operation and orient the centrifuge. The shaft 460 is driven by a brushless D.C. motor (not shown), preferably with a position encoder, located in the console 100. The motor drive electronics (not shown), mounted in the console 100, may use this encoder to achieve the necessary very smooth, vibration-free, constant-speed rotation of the centrifuge and also allows for the pins 225, slot 227 or other orientation element to be properly positioned when the cup is stopped so as to allow for proper placement of the centrifuge 515 and the CFC disk 930.

With reference to FIG. 28B, to interface with certain centrifuge designs including an umbilical 1670, the cup includes dual gears 1750 to drive the centrifuge disk while the umbilical 1670 is rotated by the cup 1761. In another alternative, concentric cups may be used, the first cup 1761 for rotating the umbilical, and within that cup 1761 a second cup 1762 for rotating the CFC disk 930 at twice the rotational velocity of the first cup 1761. The second cup 1762 includes a slot to allow the umbilical to be properly placed in the first cup. These embodiments are further described in detail below in connection with the umbilical design.

A user interface 250 is located on the outside of the top of the console 100. Preferably, the interface provides sealed push-button or diaphragm switch controls for implementing user control of the specific functions of the processes implemented by the console 100 to a limited and well-defined extent. The user interface 250 includes a display 260, which may be an alphanumeric illuminated monitor, for displaying the state of the process, for display and selection of process parameters, and for warnings or alarm conditions. The interface may include a donor line pressure indicator 270.

A bar code reader 275 may be provided in order to take bar code data such as identifiers, lot numbers and expiration dates from bags, the user, the donor and other sources. The console 100 provides date, time, and process and blood product information. All process and system data, process parameters, warnings, failures and a process validation may thus be automatically provided to a central blood bank computer.

All processes within the system are controlled by electronic controls (not shown) contained within the console 100 in a conventional manner utilizing a microprocessor-based controller with a watchdog microprocessor, or dual microprocessors, that meet medical device electronic system requirements. Electronic PC boards or similar structures, shown for example, at 340, provide electronic interfaces to various motors, actuators, transducers, and sensors. Although not shown, it will be understood that all operations of components are controlled and/or monitored by the microprocessor or other controller utilizing standard techniques known in the art, in response to inputs from the sensors, such as the pressure transducers, and to set process procedures programmed into software, stored in a ROM or other storage device, which is used to implement the process identified using a bar code 276 or other identifier on the cassette 490 that may be read by the bar code reader 275 or the like mounted in the console. It will be understood that all components will be electronically coupled to such controller via control circuits such as the transducer printed circuit board. Control software to control the microprocessor may be written in C+ or another suitable programming language, and should follow FDA and ISO guidelines for medical device software. As an alternative to a microprocessor and control software instructions, a state machine, which could be implemented using an FPGA, could be used.

Disposable Set

The disposable sets 480 for processes implemented by the system have several components as well as the overall design approach in common. This overall design is illustratively depicted in FIGS. 14 and 15 (with respect to a related system of blood collection and processing) with the structure of the cassette shown conceptually in FIGS. 16 and 17. The disposable set 480 consists of a cassette 490, including a manifold 510, a CFC 515 and a cassette frame 500 that supports the manifold 510 and the CFC 515. The frame may be formed of injection-molded plastic disposable component or similar material with sufficient rigidity to support the manifold 510 and CFC 515, and to allow the valve and sensor components 525 to be located opposite the actuators and sensors mounted on the console front panel 120 and console door 130. The manifold, frame and portions of the CFC are preferably made of clear plastic so as to allow for the use of optical sensors mounted in the console, as further described below. The cassette also has a bar code 276 that may be read by the bar code reader 275 in the console 100. This provides identification to the console 100 of the process to be implemented. It may also provide cassette calibration valves to allow for more efficient pump operation, cassette lot number and expiration date.

The disposable set 480 also includes various components 570 that are attached to the manifold 510 by tubing 550. These components 570 may include one or more solution bags or bottles, such as a glycerolizing solution bag, saline solution bag or a platelet additive solution (PAS) bag, or a glycerol bottle; blood product bags, such as a bag of packed RBCs in storage solution, a frozen red cell product bag, a glycerolized RBC bag, a deglycerolized RBC bag, a platelet product bag, buffy coat product bags, a white cell product bag or a washed RBC bag; a recirculation bag; a satellite bag; and a waste bag. Various combinations of these bags and bottles may be utilized, according to different embodiments of the present invention.

Figure 18:
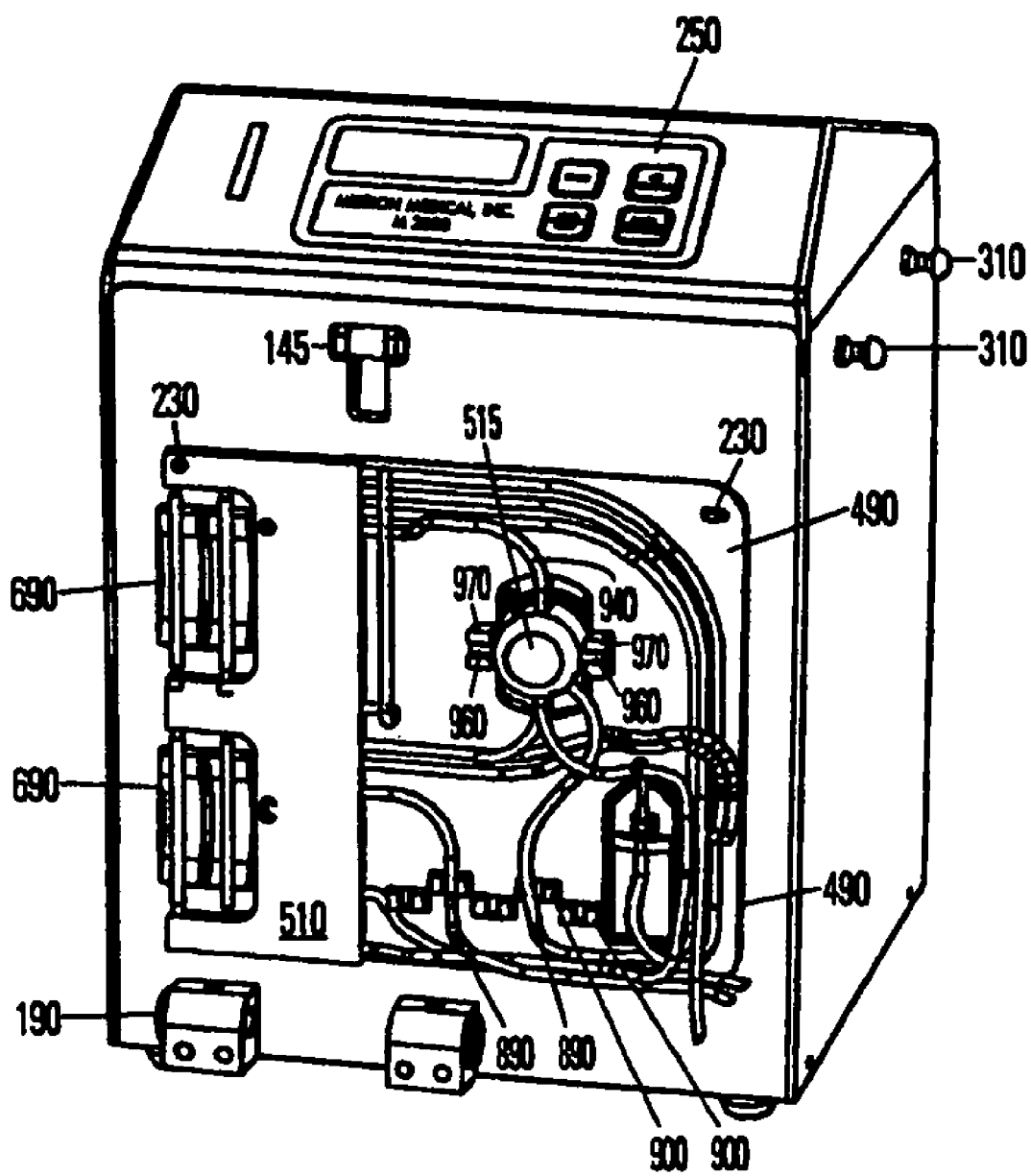
FIG. 18 is a view of a console with a cassette mounted therein, in accordance with an embodiment of the present invention.

The cassette 490 may be mounted on the vertical front panel 120 of the console, as shown in FIG. 18. The cassette 490 is held by the user vertically and is lowered into the space between the open door and the vertical console front panel 120. It is lowered until the support and alignment holes 680 in the top of the cassette 490 as shown in FIG. 18 are opposite the horizontal locating pins 230 on the front panel 120. The holes 680 and pins 230 may be placed strategically to permit only one possible placement of the cassette 490 within the console 100. With reference to FIGS. 35A and B, the cassette 490 is then pushed horizontally toward the front panel 120. The CFC 515 will first engage and slip easily into its console drive cup 220 mechanism. In a rotating cup design, pins 225 in the cup, and/or slots if an umbilical design is used, will have been properly oriented using the position locator in the drive motor. Then the locating pins 230 on the console front panel 120 will engage the support and alignment holes 680 in the cassette 490. The process of mounting the cassette 490 takes no appreciable force and is completed when the cassette 490 is mounted on the pins 230 and is contacting the console front panel components. Then the console door is closed and latched, securing the cassette 490 between the door and the console front panel 120. This cassette mounting process takes a few seconds. Then components 570, such as solution bags and blood product bags, are hung and/or connected, and the system is ready for use.

The cassette 490 is hung vertically on the console front panel 120 to allow easy, direct, close visual observation of mounting of cassette 490 to the console 100. Vertically-mounted cassettes may be easier to insert into the console 100 than horizontally-mounted cassettes. Vertical mounting also allows for a vertical door design that does not require lifting the entire weight of the door as with a horizontal door and a vertical front panel 120, which may be more easily cleaned than a horizontal front panel. Additionally, substantial vertical positioning of the cassette may allow gravity to aid in separating air from liquid in the disposable set 480 components 570; air removal, including air removal during the initial priming or filling of the centrifuge (usually including a slow rotation or clocking of the rotor) may be easier since the centrifuge can be positioned to allow air to move upward along vertical fluid pathways. Furthermore, as a safety feature, fluid leaks may be seen more easily and quickly when they occur since the fluid is not contained on a horizontal surface but flows downwards along vertical surfaces for collection at the bottom of the cassette 490. Finally, the vertically-mounted cassette 490 allows for a substantially horizontal rotor on the centrifuge drive which permits fluids to drain from and not accumulate in the drive and allows air to be more easily removed.

The manifold 510, which may be bonded or ultrasonically welded to the cassette frame 500, is shown in more detail in FIG. 19, and incorporates several components, including roller pump tubing sections 690 for liquid flow control, fluid flow pathways to the sensor and valve actuation components 546, 520, which are more specifically identified below in the discussion of the various system procedures; valve diaphragm 530 components to turn on or off fluid flow in selected fluid pathways 750; and pressure diaphragm 540 components to measure selected fluid pathway 750 pressures.

The manifold 510 includes molded-in fluid pathways 760 and may include interfaces for valves and sensors. In the embodiment illustratively depicted in FIGS. 18 and 19, four roller pump tubes 690 are connected to various fluid pathways 760. The fluid pathways 760 end in tubing receptacles 934-939 and 941-950 for receiving tubing 550 that attaches selected components 570 appropriate for the process the cassette 490 is intended to perform. It will be appreciated by those of ordinary skill in the art that a primary feature of the system is flexibility, in that it may perform different process by utilizing different cassettes and software. For this reason, not all of the fluid pathways and/or roller pump tubes would be used in every process, and, depending on the process, some could be selectively eliminated without affecting the performance of the cassette. Furthermore, the exact position of the various tubing, valves and pressure sensors could be altered, providing the associated elements of the console 100 were modified accordingly, without affecting the basic concepts of the manifold design. For ease of explanation of the structure of the manifold 510, however, the figures include fluid pathways and tubing that would not be used in all processes. Additionally, including all possible fluid pathways and tubing for multiple processes could assist in the manufacturing process by allowing for a consistent basic manifold structure that could be used with more than one process. Ideally, a single manifold structure could be used with all processes.

As depicted in FIGS. 5-8, the manifold 510 consists of three parts: a mid-body 780 into which channels, including fluid pathways 760 are molded from one side; a back cover 790, adjacent to the console front panel 120 when in operation, which seals the valves, pressure sensors and any other component interfaces; and a front cover 800, adjacent to the console door when in operation, that covers and seals each fluid pathway. The back cover 790 traps the elastomeric valve diaphragms 530 and pressure diaphragms 540, which are part of the valve and sensor components 520, 546, and which may be two-part molded to the front cover 800 at the location shown at 770, between the front cover 800 and the mid-body 780. The elastomeric diaphragms provide the deformable surfaces for valve and pressure sensor interfaces. It may also be appropriate to mold fluid pathways 760 in both sides of the mid-body, allowing for more channels and potentially simplified arrangement of elements on the cassette.

Figure 12A:
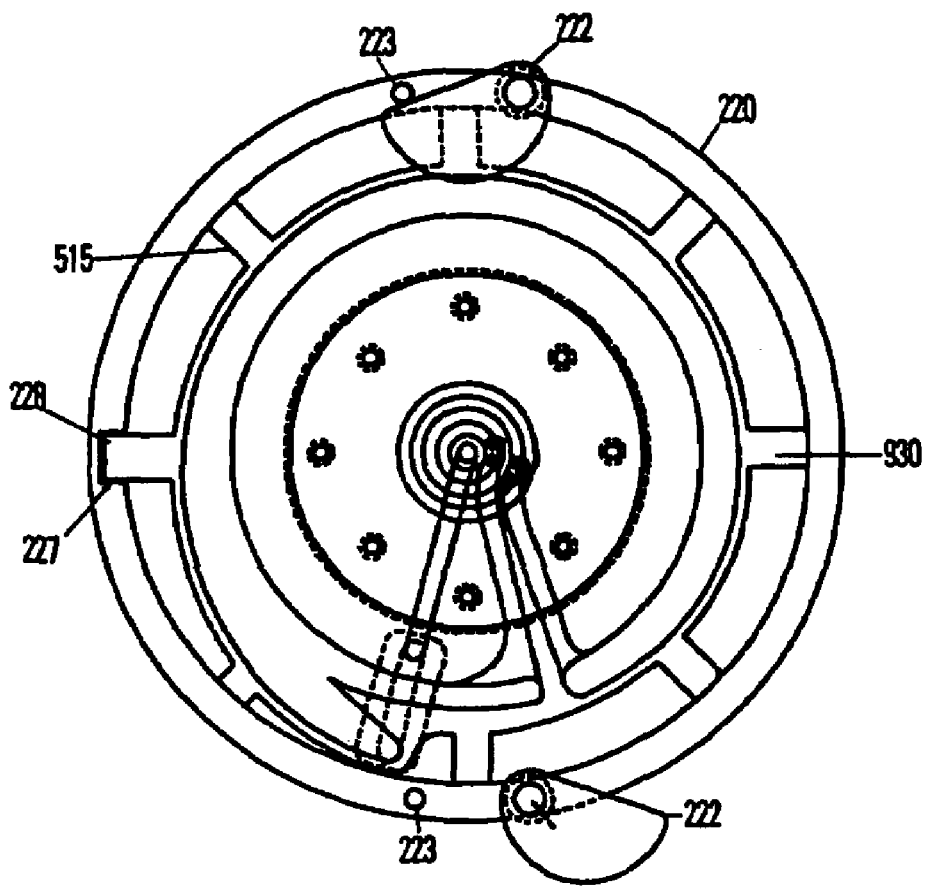
FIGS. 12A and 12B depict a drive cup, in accordance with an embodiment of the present invention.
Figure 12B:
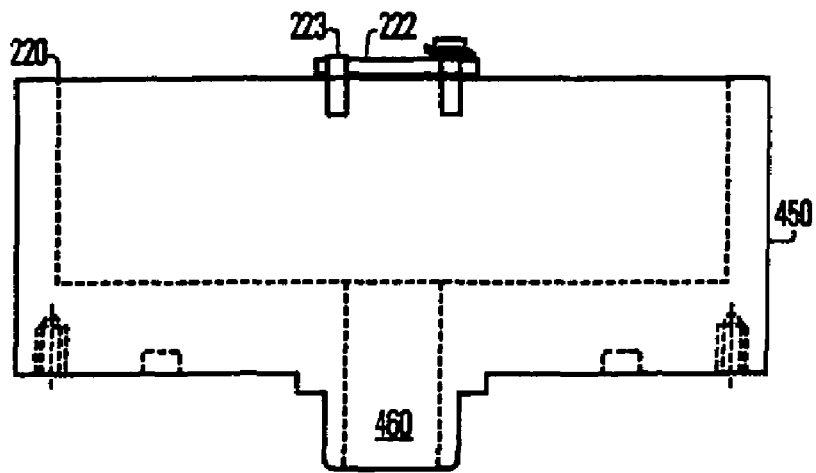
Figure 13:
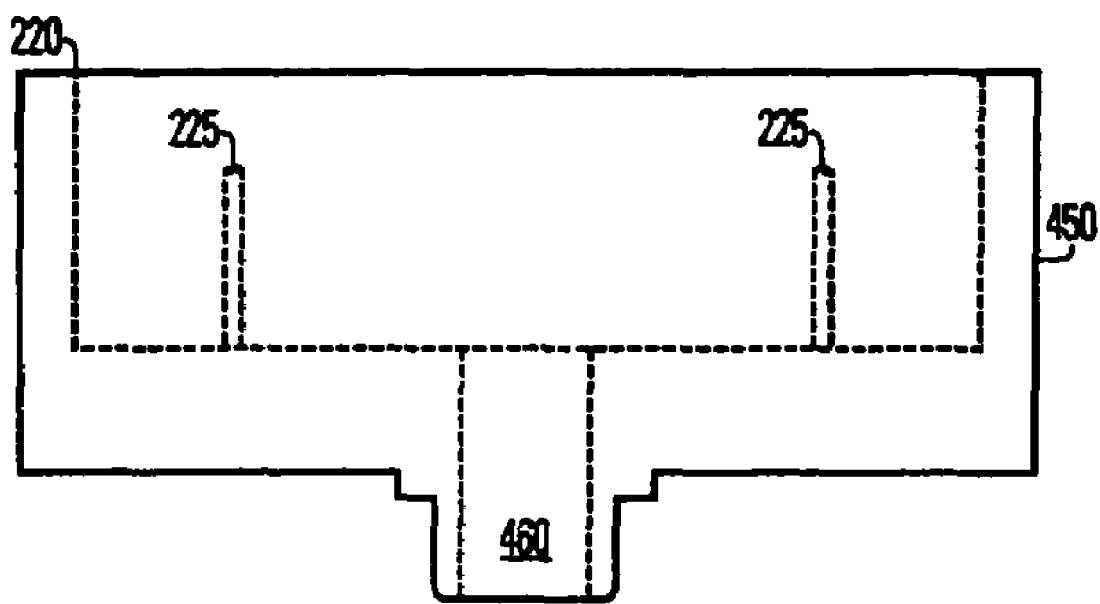
FIG. 13 depicts alternative features for a drive cup, in accordance with an embodiment of the present invention.

The operation of the valve components 520 will now be described. When the cassette 490 is mounted on the front panel 120, the valve diaphragms 530 are each located opposite the valve actuators 210, shown as solenoids with plungers 290, secured to the front panel 120. The elastomeric valve diaphragm 530 is in a normally open position when not deformed by the plunger 290, and resists deformation by the plunger 290 to close the valve. The valve diaphragm 530 also resists negative pressures and does not close when exposed to such pressures within the fluid path. When the console door is closed, the cassette 490 is moved by the door up against the console front panel 120 and the spring-loaded plunger 290 is thereby forced against the diaphragm 530. The valve diaphragms 530 are deformed by the spring-loaded plungers 290 on the console 100 to contact and occlude a tubular port 810 molded into the mid-body 780 and thereby close a fluid pathway. The tubular port 810 has a raised annulus 820 around it against which the plunger 290 pushes, creating a seal and closing the port and fluid flow path. When the solenoid is energized, the plunger 290 pulls away from the manifold 510, allowing the diaphragm 530 to pull away from the port due to its elastomeric bias, and the fluid path is open. With reference to FIGS. 11 and 12, the pressure diaphragms 540 contact pressure transducer 190 faces to expose the transducer face 830 to the fluid pressure. The front and back covers 790, 800 are ultrasonically welded to the mid-body 780 along each side of each valve, pressure or other components and the fluid pathways 760 to prevent fluid leaks between pathways or to the outside.

Figure 5:
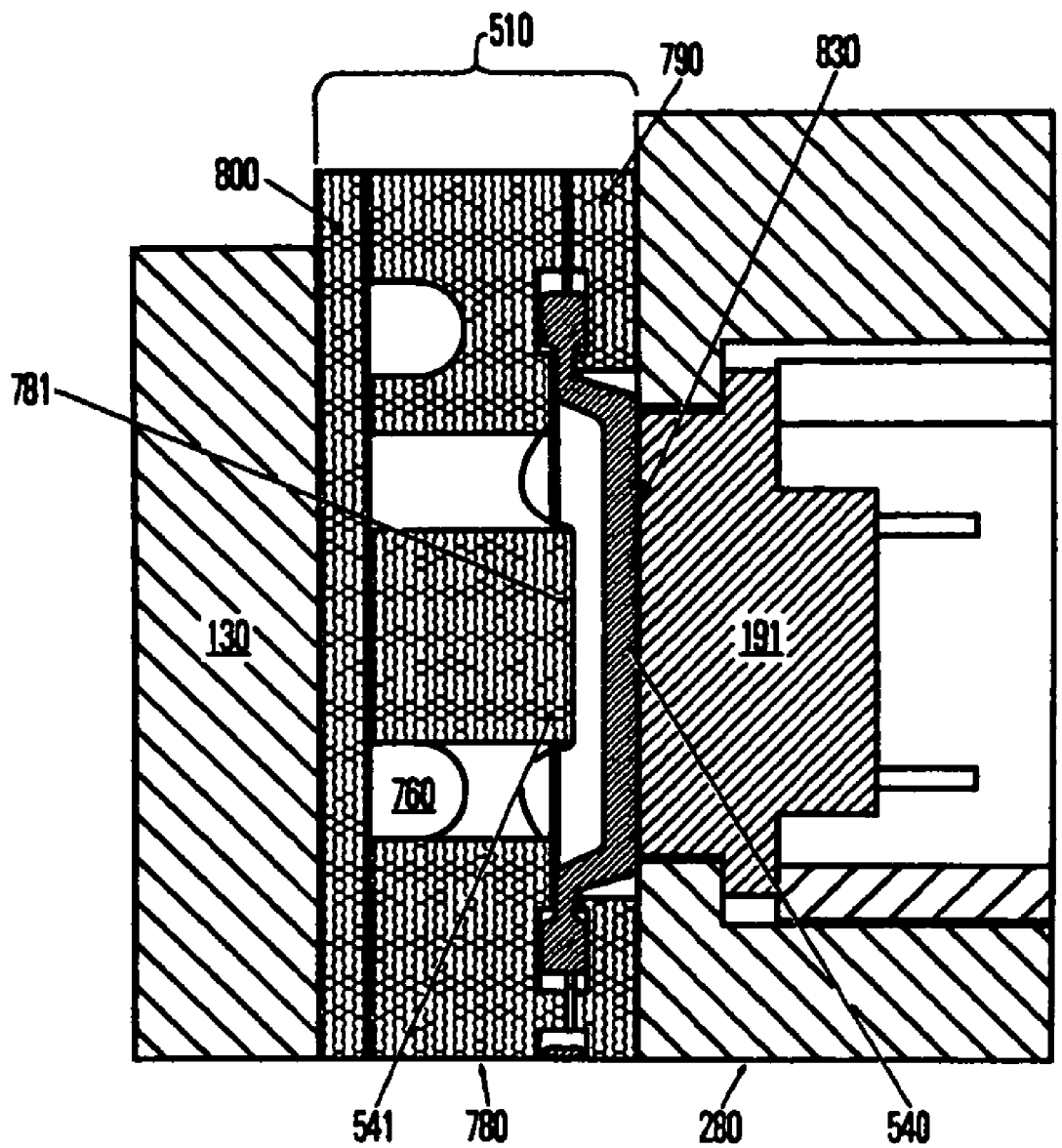
FIG. 5 depicts a positive pressure sensing transducer and associated pressure component, in accordance with an embodiment of the present invention.

The sensor components 546 will now be described in more detail. The design of the positive pressure components, which are integrated and molded into the cassette 490, are shown in FIG. 5. A flexible elastomeric pressure diaphragm 540, of material similar to the valve diaphragm 530, is sealed between the back cover 790 and the mid-body 780 of the manifold 510. Fluid pathways 760 bring fluid into and out of the mid-body 780 space 781 adjacent to the diaphragm 540. When the console door is closed, the outer surface of the pressure diaphragm 540 contacts the face of a pressure transducer 191 which is mounted to the console front panel 120. The fluid in the fluid pathway 760 exerts pressure across the highly flexible diaphragm 540 to the transducer face 830. The transducer output may be reset to zero every time a new cassette 490 is installed and before the process is begun, using ambient air pressure inside the manifold 510.

One possible design of the negative pressure component is shown in FIG. 6. It is much like the positive pressure interface design, except a spring 845 causes the piston 840 to exert a fixed force equivalent, in the example shown, to a pressure of about 250 mm Hg on the diaphragm 540 and on the negative pressure transducer or sensor 200. The function of the spring-loaded piston 840 is to keep the pressure diaphragm 540 in contact with the sensor face 830 during negative fluid pressures and provide a fixed pressure offset. Consequently, in the example shown, when the pressure reading is zeroed at ambient pressure before the process begins, the transducer in reality is seeing the pressure of the spring-loaded piston 840, but reading zero. Thus, a negative fluid pressure can be measured down to the negative of the fixed force equivalent, in this case −250 mm Hg, before the pressure diaphragm 540 pulls away from the transducer face 830. However, no pressure less than the negative value of the equivalent fixed force, or −250 mm Hg in the example shown, can be read.

Figure 7:
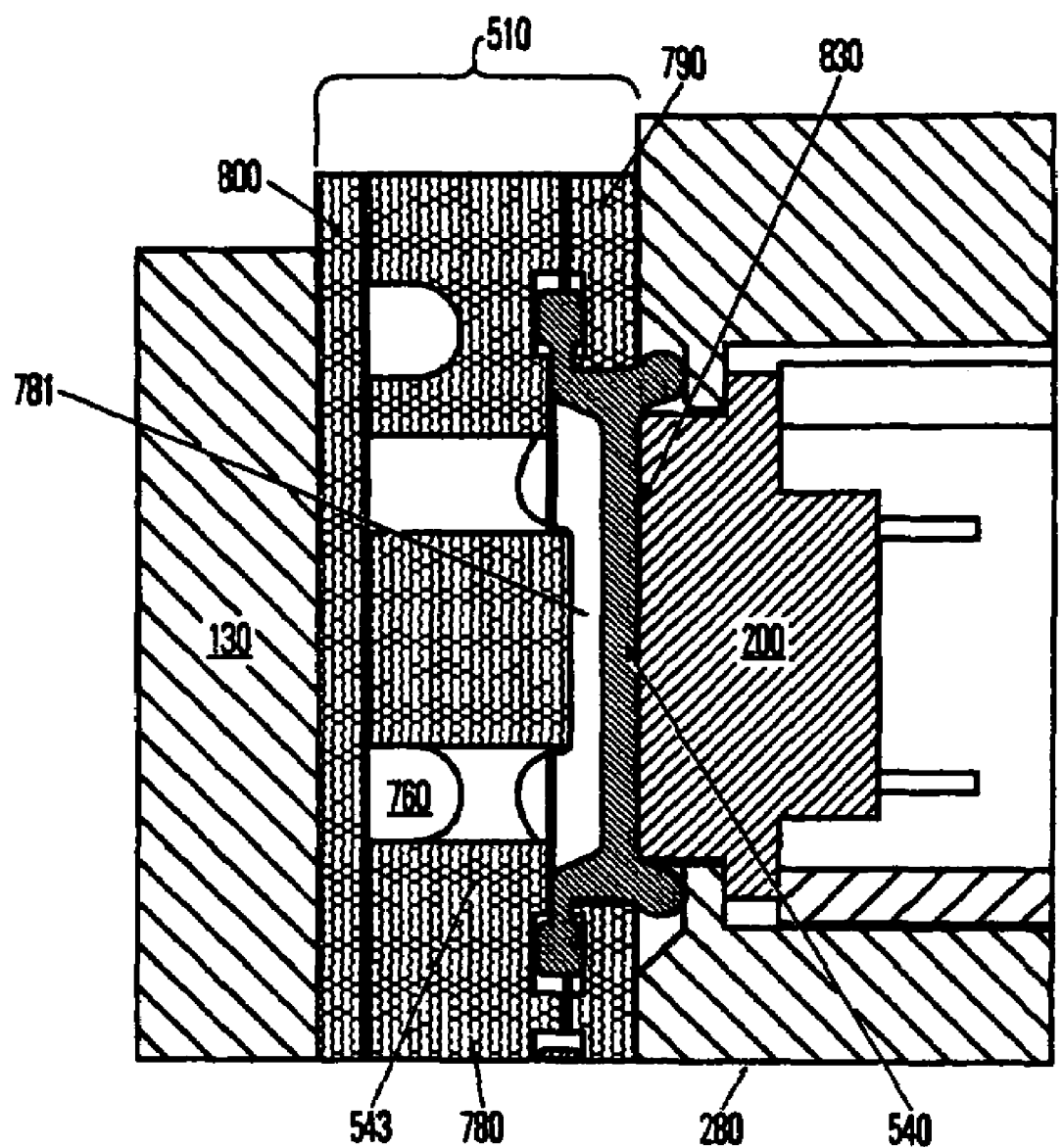
FIG. 7 depicts an alternate embodiment for a negative pressure transducer and associated pressure component, in accordance with an embodiment of the present invention.

An alternative negative pressure design is shown in FIG. 7. In this design, the elastomeric pressure diaphragm 540 has a peripheral seal member 850 that seals the pressure diaphragm 540 to the console front panel 120. Air is trapped in the space 781 between the pressure diaphragm 540 and transducer face 830. This permits positive and negative pressures to be read by the transducer via the trapped air volume. This transducer or sensor is also zeroed by ambient pressure before the process begins.

Figure 19:
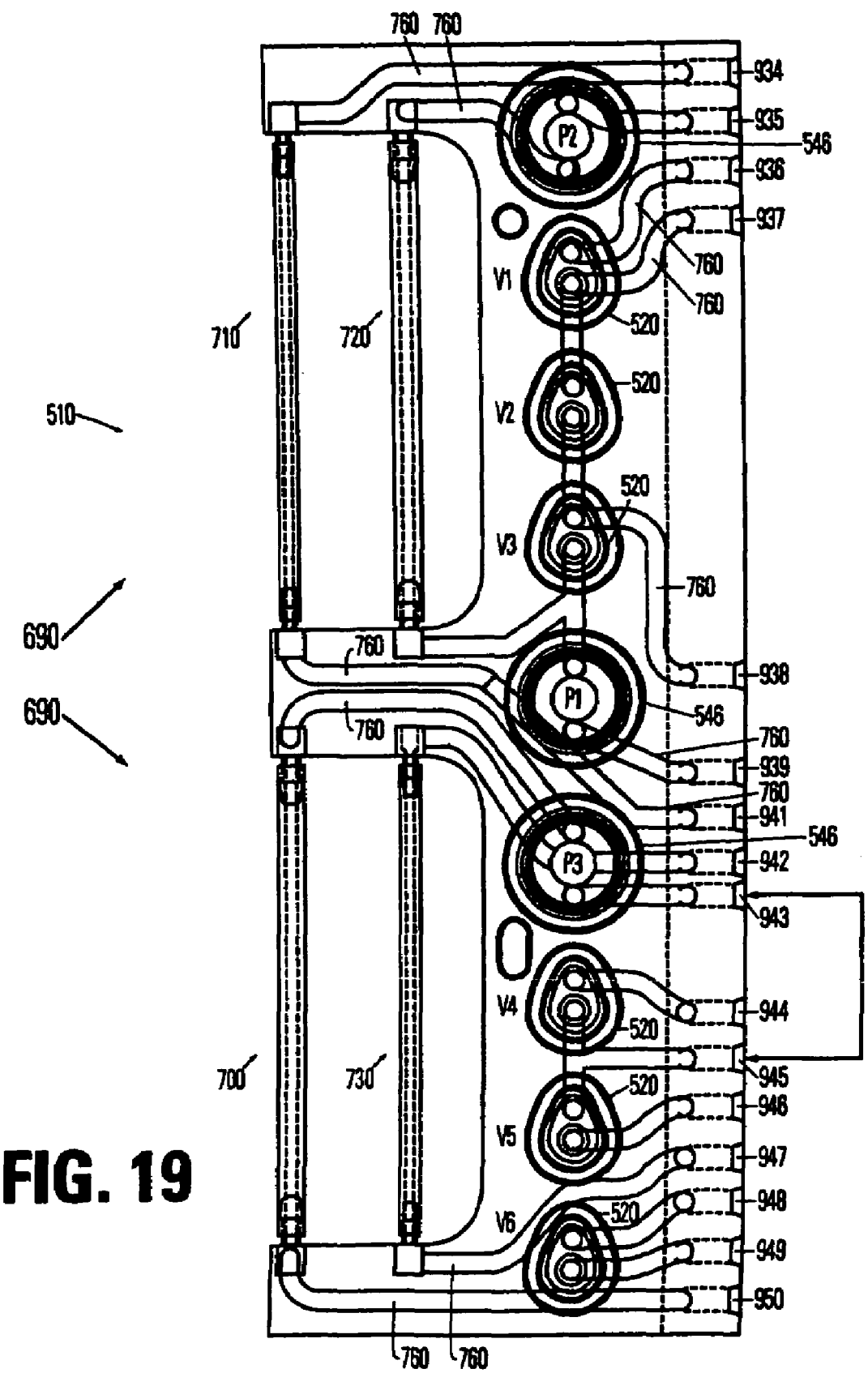
FIG. 19 is a detailed schematic of a manifold portion of a cassette, in accordance with an embodiment of the present invention.
Figure 20:
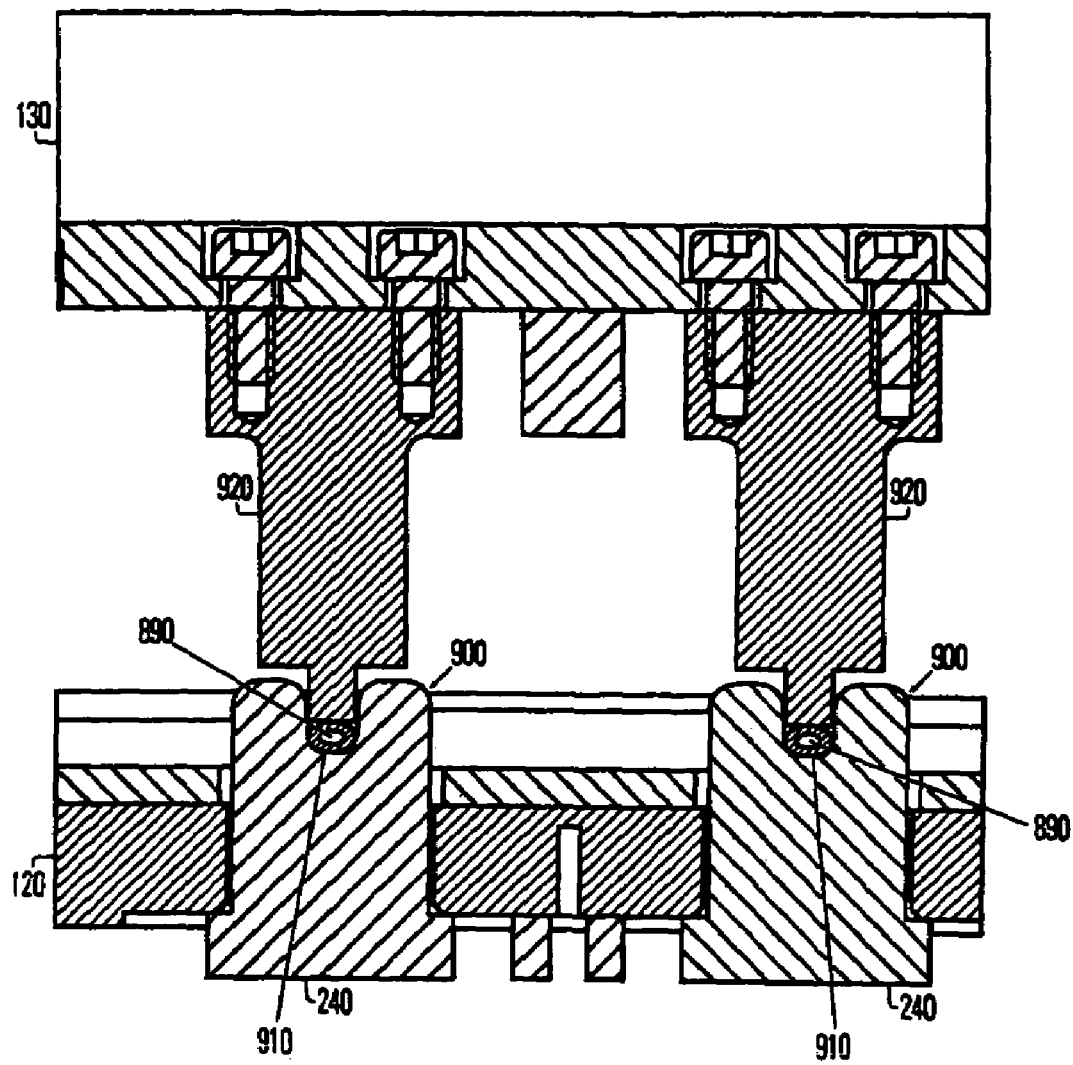
FIG. 20 is a cutaway view of ultrasonic sensors, in accordance with an embodiment of the present invention.

With reference to FIG. 19, the four roller pump tubing segments 690 can be constructed of segments of extruded PVC tubing formulated and dimensioned to have properties optimized for use with the roller pump 160. In the embodiment shown, these roller pump tube segments 690 are in two sets of two; allowing interface with the roller pump rotors mounted in two sets of two on concentric bearings. This design creates a more compact cassette design. They include four tubing segments 700, 710, 720, 730. In each set the tubes are adjacent to one other, parallel, and closely spaced. This tubing is slightly stretched onto and bonded to barbed fittings 860 molded to and part of the cassette mid-body 780.

With reference to FIGS. 3 and 10A, the roller pump and drive mechanism 160 with motors are located in the console door. The roller pump tubes are unengaged when the console door is open. When the door is closed and locked in place, the roller pump rotors 350 engage the roller pump tubing 690. The rollers 410 on each rotor compress and occlude the tubing against a curved block or track that is mounted to the console front panel 120. No action on the part of the user is needed except to close the door. This eliminates the manual step of inserting tubing into each pump assembly required by many blood processing systems and eliminates the possibility of operator error.

The track may be spring-loaded 180 against the rollers 410 to ensure adequate occlusion while avoiding excessive force. The track 170 is pivoted on a track pivot pin 175 parallel to the console front panel 120 at some distance from the center of the track 170. The track is provided with a stop 177 that limits its motion in the direction of the spring force, which is biased towards the rotors 350. The control of spring force and tubing compression by pump rollers 410 to the lowest level necessary to ensure occlusion minimizes hemolysis in this pump design. The roller pump tube segment inside diameter is selected for the flow rates of fluid desired, the degree of "pulsatility" of the fluid that can be allowed, and the speed range capability of the pump rotors 350. This inside diameter is controlled precisely, with tolerances preferably of less than plus or minus 3 mils, in order to achieve accurate flow control in operation as the rotors 350 force the rollers 410 over the roller tubing segments to pump the various liquids through the system.

Figure 14:
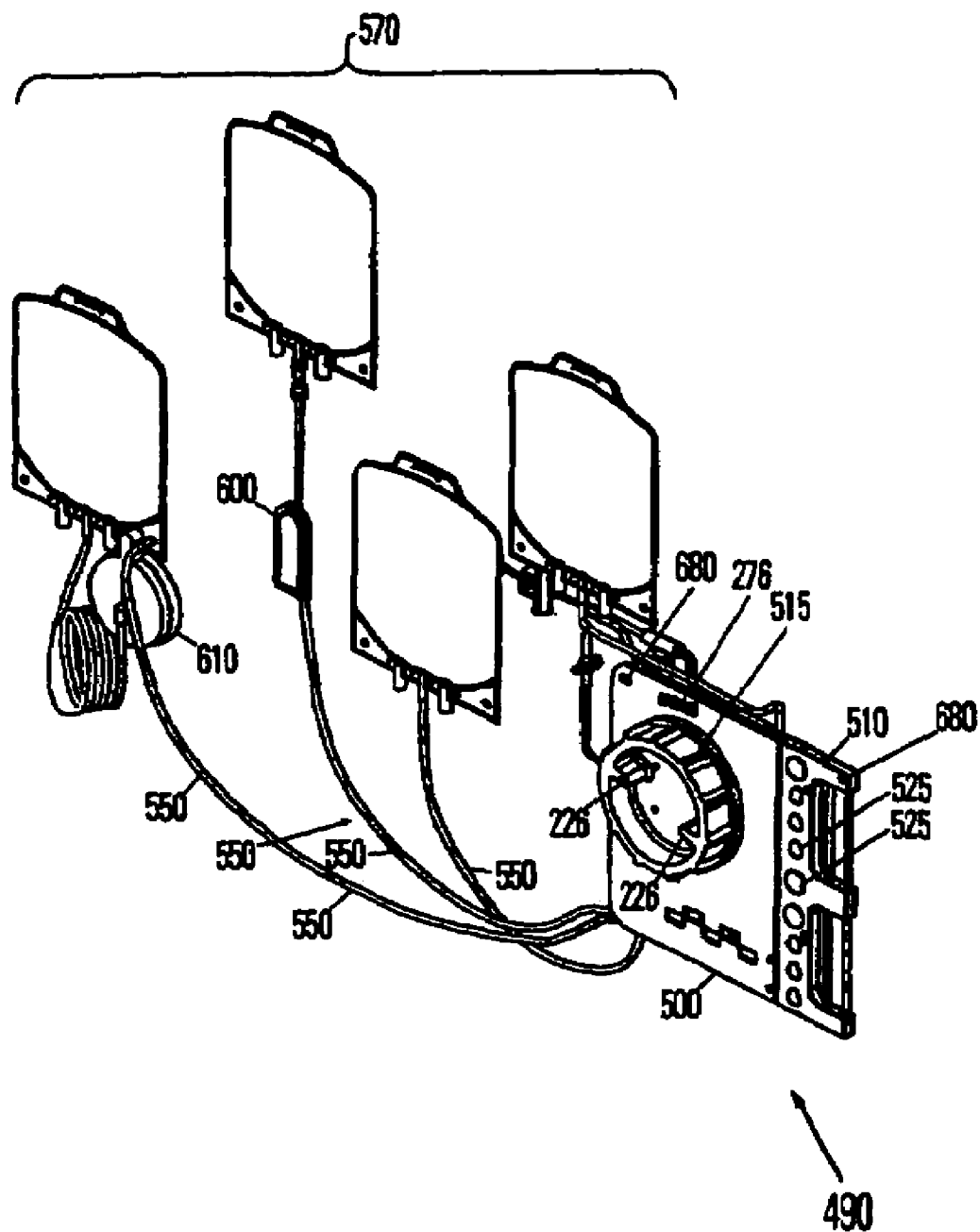
FIG. 14 is a first view of a disposable set, in accordance with an embodiment of the present invention.

The manifold 510 also supports tubing 550 that is routed from the manifold 510 to bags and/or other components 570. The tubing 550 provides a path for fluids moving to and from components 570. Tubing 550 is bonded to or captured onto the frame at the tubing receptacles, as shown in FIG. 19. With reference to FIGS. 14-16, the components 570 vary for each process, but can include such items as a leukofilter 610 for red cells; bacterial filters 600 for anticoagulant, red cell additive, glycerolizing solution, PAS, glycerol or other solution bags or bottles attached to the set by the use of spikes 870 or by Luer connectors 880; possible air or bubble traps (not shown); bags for blood products 590, including, for example, red blood cell bags, buffy coat bags, plasma bags, packed RBCs in storage solution, frozen red cell product bags, glycerolized RBCs bag, deglycerolized RBCs bag, platelet product bag, white cell product bags or washed RBCs bags; a recirculation bag; a satellite bag; a waste bag; and other various fittings, elbows, Y-connectors, and manual clamps as appropriate. Some of these components 570 may be attached to the cassette frame 500. Preferably, all tubing 550 is bonded into selected tubing receptacles 934-939 and 941-950 on one side of the manifold 510, as shown in the embodiment illustratively depicted, to simplify and shorten tubing runs to components 570 or bags. The specific components 570 for various processes are indicated in the process descriptions and schematics that are described in more detail below.

With reference to FIGS. 16, 17, 18 and 20, portions of the tubing 890 from the components 570 are bonded or captured to the frame on each side of access holes 900 in the cassette frame 500 and engage ultrasonic sensors 240 mounted in the console front panel 120. The tubing 550 can be standard PVC tubing used for fluid flow from the cassette 490 to various external components 570, bags, and the like. The access hole in the cassette frame 500 bridged by the tubing 550 permits the yoke-shaped sensor to surround the tubing segment on three sides. When the cassette 490 is hung on the front panel 120, the air detection tubing is adjacent to and partially within the slot 910 in the sensor. When the door 130 is closed, a finger 920 on the door pushes the tubing into the slot 910 and compresses it to ensure good contact with the parallel sides of the slot 910 achieving good acoustic coupling. An ultrasonic transducer sends ultrasonic waves through the tube across these parallel sides to a receiving transducer on the opposite side of the slot 910. The differences in acoustic properties between liquids, air and air bubbles in liquids are determined by the ultrasonic sensor and its electronics. This is used to monitor air in the system, for ensuring the process is occurring without air bubbles and for detecting empty liquid-containing bags.

Figure 17:
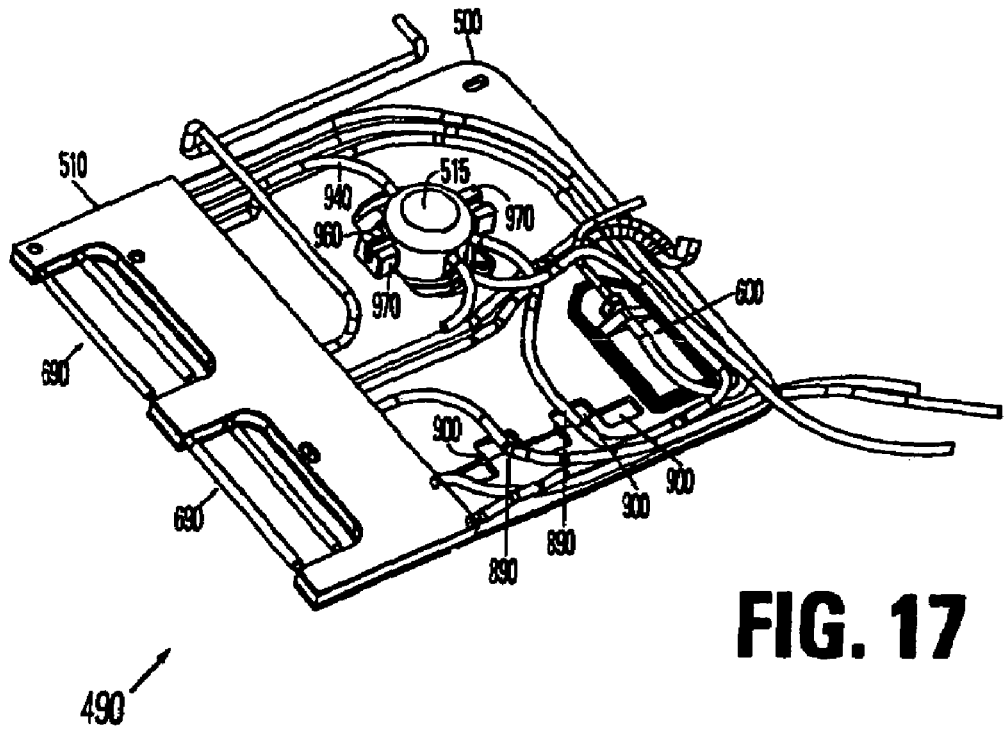
FIG. 17 is a detailed view of a cassette, in accordance with an embodiment of the present invention.

With reference to FIGS. 17 and 18, the CFC 515, including the CFC disk 930, is also connected to the manifold 510 by tubing 940. The cassette frame 500 supports the CFC disk 930 loosely and allows direct, easy insertion of the centrifuge into the centrifuge drive cup 220 simultaneous with hanging the cassette 490 on the console front panel 120, without complicating cassette mounting. Details of the CFC 515 are further described below.

Continuous Flow Centrifuge

The CFC 515 is "flexibly" supported on the cassette frame 500 such that it is easily inserted into a centrifuge drive cup 220, 1762 during cassette installation. This "flexible" support structure is decoupled from the disk 930 when the door is closed, permitting the CFC disk 930 to rotate freely. The attachment of the CFC disk 930 to the cassette frame 500 is shown in FIGS. 17 and 18. The CFC disk 930 is attached to the cassette 490 in such a way that it can readily move approximately ±0.040 inch in any direction parallel to the front panel 120 and approximately 0.1 inch toward the front panel 120. Two pins 960 at 180° from one another on the disk static seal housing 1430 fit loosely in two yokes 970 that are part of the cassette frame 500. In the embodiments depicted, the CFC disk 930 is approximately 6 inches in outside diameter and 1.75 inches thick, although other dimensions are possible.

Figure 24:
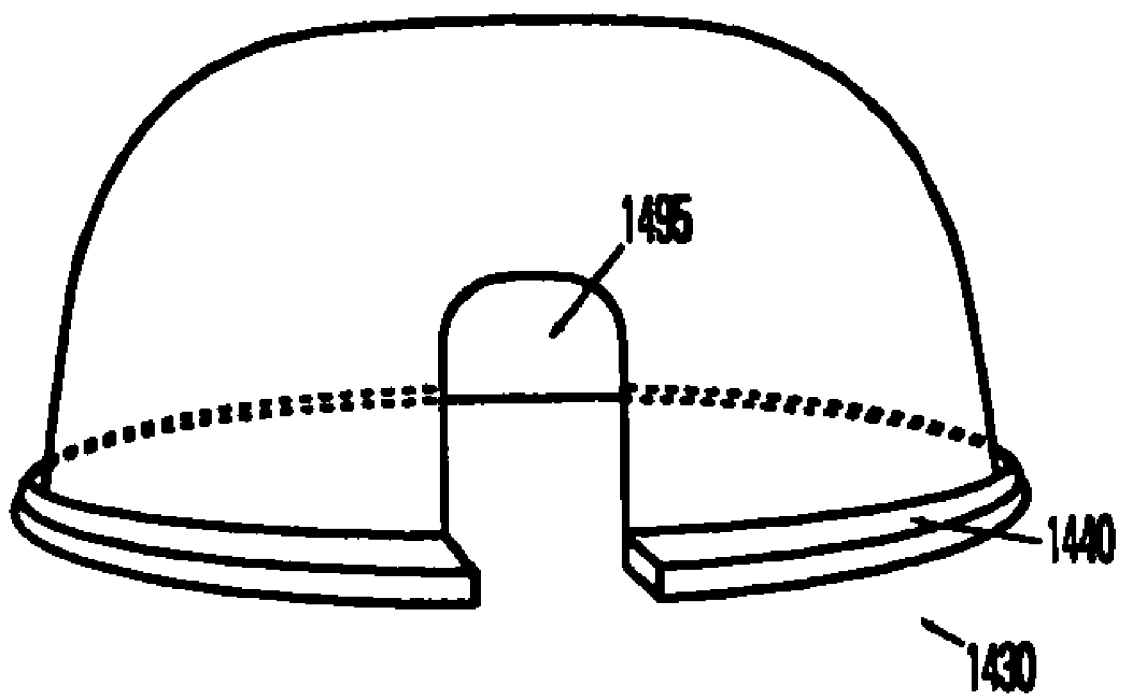
FIG. 24 depicts a detail of a housing for the centrifuge, in accordance with an embodiment of the present invention.

Two possible approaches to the design of the CFC 515 are described below. In the first approach, with reference to FIGS. 21-24, the CFC apparatus includes several elements that are able to rotate around a central spin axis 1460. These elements include a housing mounting ring 1450, a rotating face seal, a disk cap 1500 and a disk body 1150. The rotating face seal 1480 is supported adjacent to the disk cap 1500, which is mounted on a housing mounting ring 1450 that is rotatably connected to rotate around the opening of a bucket-like stationary housing 1430. Contained within the housing 1430 and adjacent to the rotating face seal 1480 is a stationary face seal 1490, which is bonded to a distributor 1530. The stationary face seal 1490 is slidably mounted in the housing 1430, and is also attached to a spring or other spring-loading element 1410 mounted at the top of the housing 1430. With reference to FIG. 24 the housing forms slot or slots 1495 that allow tubing to be connected to the distributor 1530, while permitting movement of the housing 1430 as described below.

The CFC disk 930 is supported on the cassette 490 but must be free to rotate after the cassette 490 is in place, mounted to the console body 110 front panel 120, with the console door closed. The console door closure is used to disengage the CFC disk 930 from the cassette 490 such that the disk 930 can rotate freely and is positioned and supported correctly and safely within the centrifuge drive cup 220.

To accomplish this, the housing 1430 includes an engagement lip around the opening. The spring-loading element 1410 in the housing 1430 forces the engagement lip 1440 against the housing mounting ring 1450. The centrifuge assembly of FIG. 24A shows the engagement lip on the static seal housing 1430 contacting a disk housing mounting ring 1450, preventing disk rotation. The door of the console in this embodiment includes a plunger 295 or similar structure, as shown in FIG. 24B, that will, when the door 130 is closed, engage the housing 1430; compressing this housing against the spring-loading element 1410, and moving the housing 1430 a fixed distance. This separates the engagement lip 1440 from the mounting ring 1450; permitting rotation of the elements mounted, directly or indirectly, on the housing mounting ring 1450. In practice, it may be preferable to include additional elements to improve performance of the device. For example, with reference to FIG. 22, guide 1505 may be mounted on the rotating disk cap 1500, to maintain the rotating and stationary face seals 1480, 1490 in alignment, as the spring-loading element 1410 is compressed against the housing. The guide 1505 may also act as a shield to prevent spattering of liquid in the event the seal is compromised.

Figure 22:
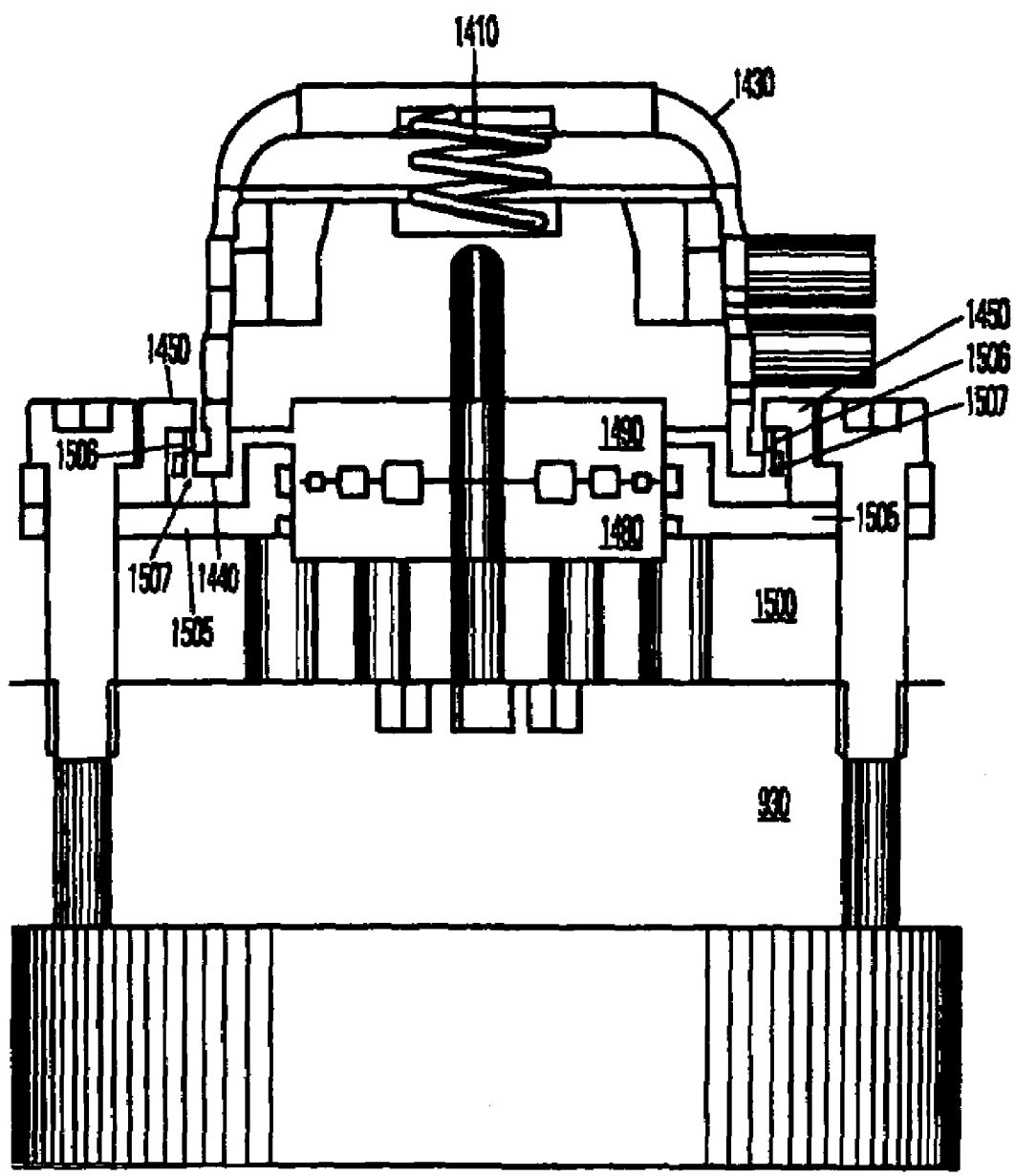
FIG. 22 depicts a detailed design of a continuous flow centrifuge that uses a face seal, in accordance with an embodiment of the present invention.

The CFC disk 930 is preferably keyed in angular location to the cassette 490 when the centrifuge is not mounted in the console. This may be accomplished using a tongue-in-groove that is disengaged when the rotor is pushed toward the front panel 120 by the door, or alternatively, as shown in FIG. 22, using pins 1506 on the housing mounting ring 1450, and holes 1507 in the lip 1440 of the housing 1430. This alignment of the CFC disk 930 allows appropriate positioning of the CFC disk 930 relative to the console, and permits precise control of disk location during priming and other elements of the processes performed by the system as further described below.

Other variations are possible. For example, a stationary sleeve could be attached to a flexing annular part that attaches to the stationary face seal or the distributor 1530. The stationary sleeve could have an annular lip extending radially inward that engages an annular lip on a sleeve that rotates with and is attached to the rotor. The flexing annular part provides sufficient elastic force to make the gap zero between these engaged lips and provides a force that keeps the seal faces firmly pressed together. A projection on the sleeve engages a slot or hole on the stationary sleeve to maintain angular orientation between the rotor, stationary seal and the cassette. The stationary seal and its distributor are attached to the cassette by a cassette structure that provides angular alignment of the stationary seal.

Figure 25:
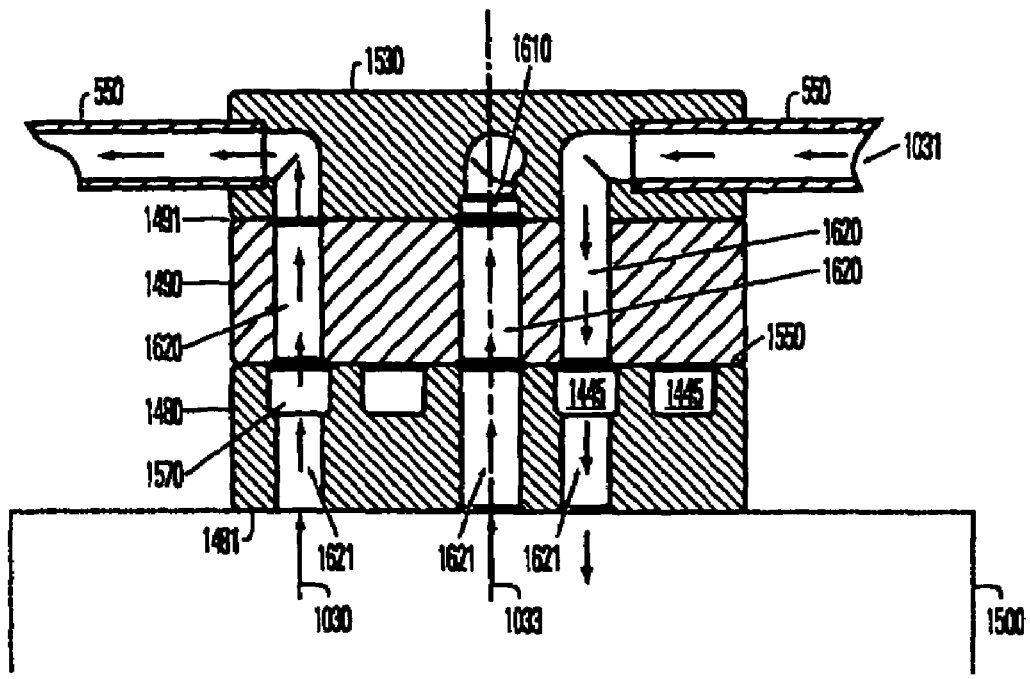
FIG. 25 depicts a face seal with three fluid paths, in accordance with an embodiment of the present invention.

With reference to FIG. 25, the face seal structure will be described in more detail. The face seal is used for the sealing of fluid paths or ducts that act as the means for transporting fluids from the cassette 490 into the rotating CFC disk 930, and transporting other fluids from the rotating disk 930 to the stationary cassette 490.

The face seal assembly comprises a rotating ceramic (e.g., aluminum oxide) face seal and a stationary face seal 1490. The stationary face seal 1490 may be made of carbon (e.g., carbon-graphite) or of ceramic. Although carbon has better lubricating capacities and is preferred for that reason, the use of this material may produce an unacceptable amount of particulates. Further, ceramic wears better and may more easily be manufactured to the appropriate "flatness." As noted above, the spring-loading element 1410 provides sufficient force at all times that keep the rotating and stationary seal faces 1480, 1490 in contact with each other. The face seal components each have a central hole 1610 and two or three annular channels 1445 with access holes 1620, 1621 to provide three or four fluid paths. The rotating face seal 1480 is adhesive-bonded 1481 to the molded plastic centrifuge disk cap 1500. The disk cap 1500 provides fluid channel access to the ceramic fluid path holes. The annular channels 1445 in the rotating face seal 1480 collect flow from localized holes 1620 in the stationary face seal 1490. The mating surfaces of the face seals are made extremely flat, to less than three helium wavelengths. This ensures sealing of all of the flat lands between the grooves. The outer face seal land 1550 is the only seal to the outside or to ambient air and is the only face seal that could allow bacterial contamination of the fluids in the system from ambient air. Therefore, this outer face seal must not leak. However, the internal face seals can leak slightly without compromising blood component quality or sterility.

A plastic molded distributor 1530 is adhesive-bonded 1491 to the stationary face seal part 1490. Flexible tubes 550 attach to the fluid ducts of this distributor 1530 and connect to the manifold 510 thus connecting stationary face seal 1490 and its fluid pathways 750 to the stationary disposable components 570 that are part of the disposable cassette 490.

This face seal assembly is made from materials used in similar blood applications and with similar dimensions and compressive forces. This is done to ensure proper function and also to more easily obtain FDA approvals, but other designs and modifications may be possible.

Figure 26:
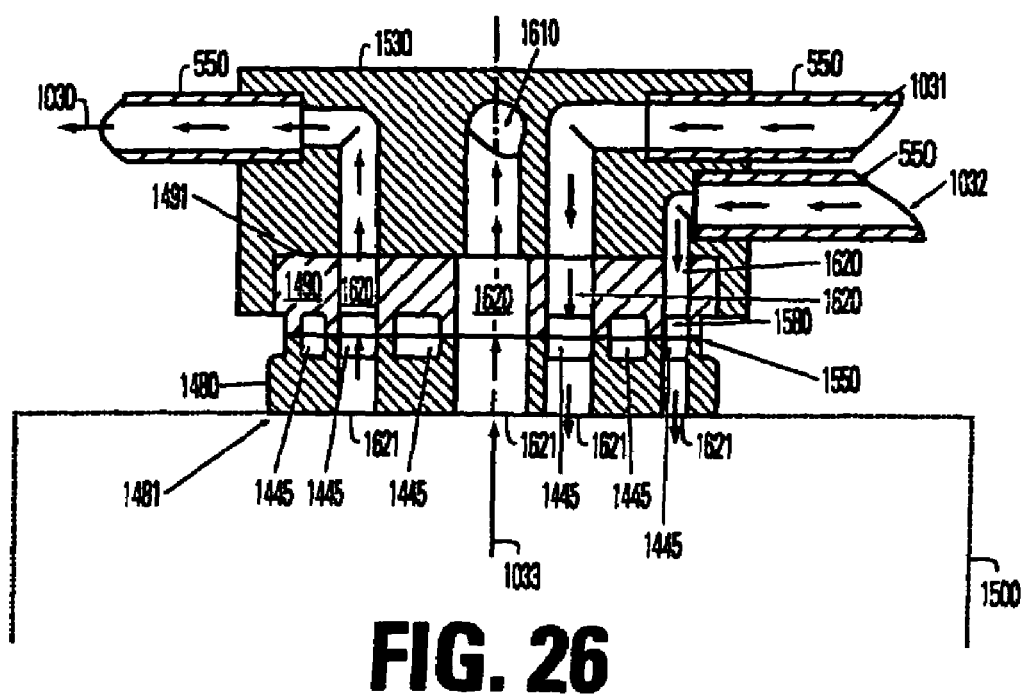
FIG. 26 depicts a face seal with four fluid paths, in accordance with an embodiment of the present invention.

An alternative face seal design is shown in FIG. 26. This is very much like the design in the embodiment of FIG. 25, except that it has four fluid pathways rather than three. The additional outer annular channel 1580 provides a fluid path for an additional fluid 1032. This fluid may be pumped into the CFC disk 930 through the face seal. The fluid 1032 flow in its annular channel within the seal may also cool seal surfaces and provide some lubrication to the sealing faces or lands. The fluid 1032 pressure may be maintained near ambient to prevent air leaks into the storage solution from the non-sterile ambient air (if the fluid 1032 pressure were very negative); and to prevent leaks out into the ambient environment (if the fluid 1032 pressure were very positive). Such leaks out of the seal (if only of particular fluids, such as storage solution) would not be a biohazard, or any hazard, to the user.

Figure 27:
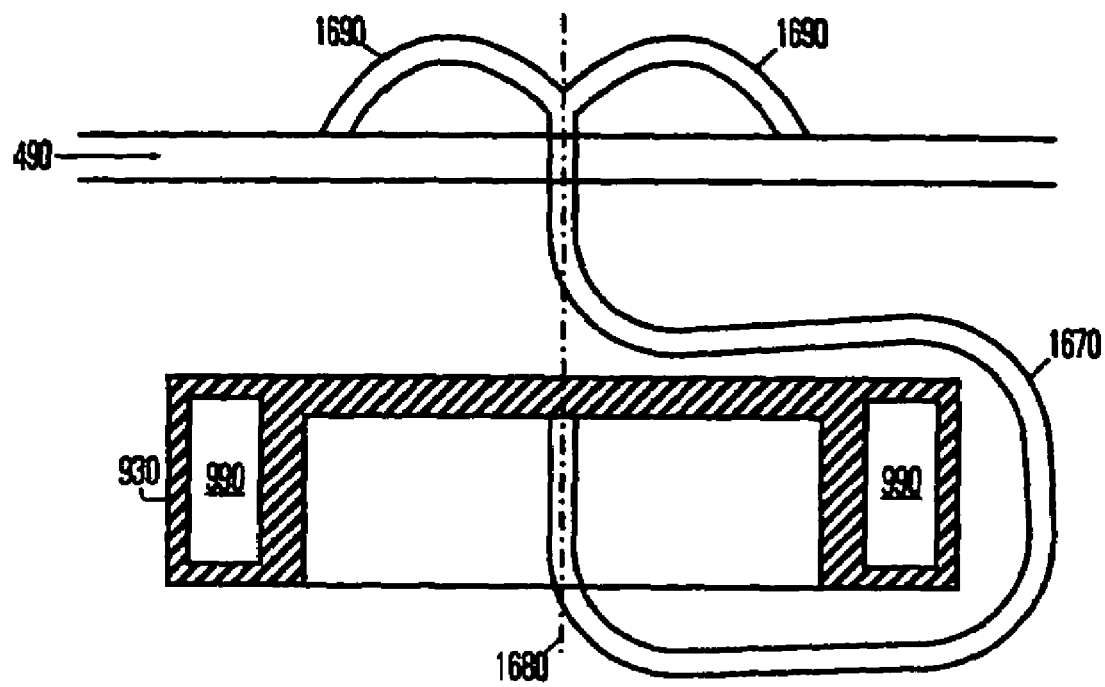
FIG. 27 is a conceptual representation of an umbilical or skiprope design for a continuous flow centrifuge, in accordance with an embodiment of the present invention.
Figure 29:
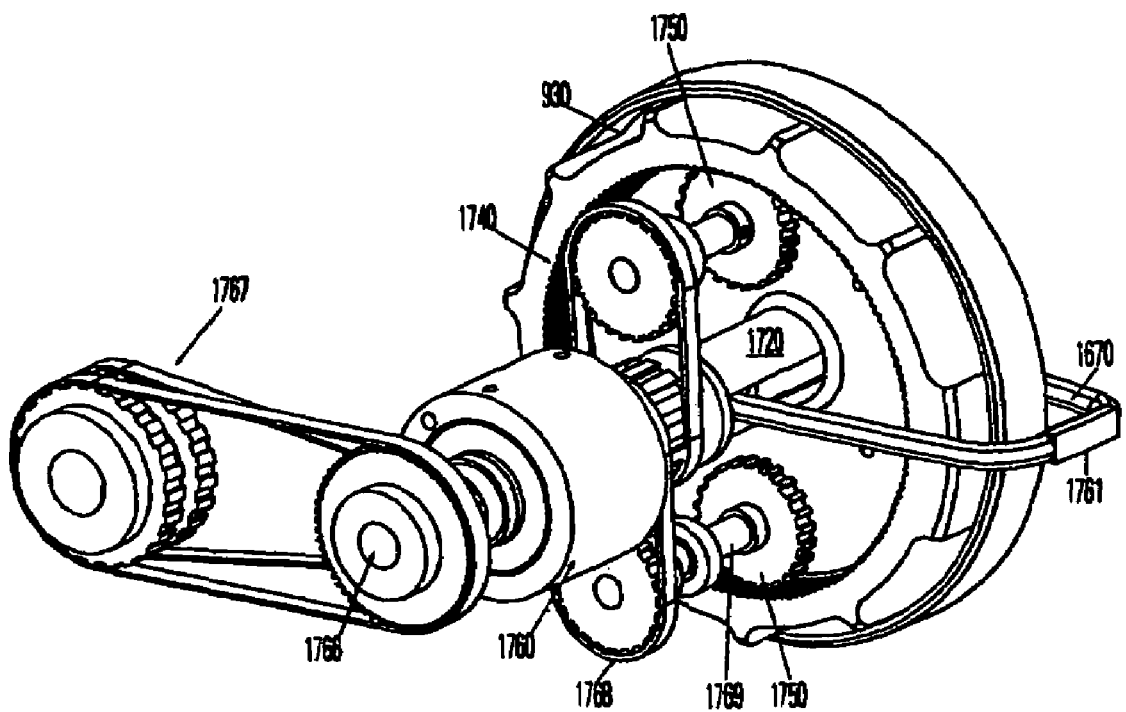
FIG. 29 is a view of drive mechanisms for an umbilical continuous flow centrifuge, in accordance with an embodiment of the present invention.
Figure 30A:
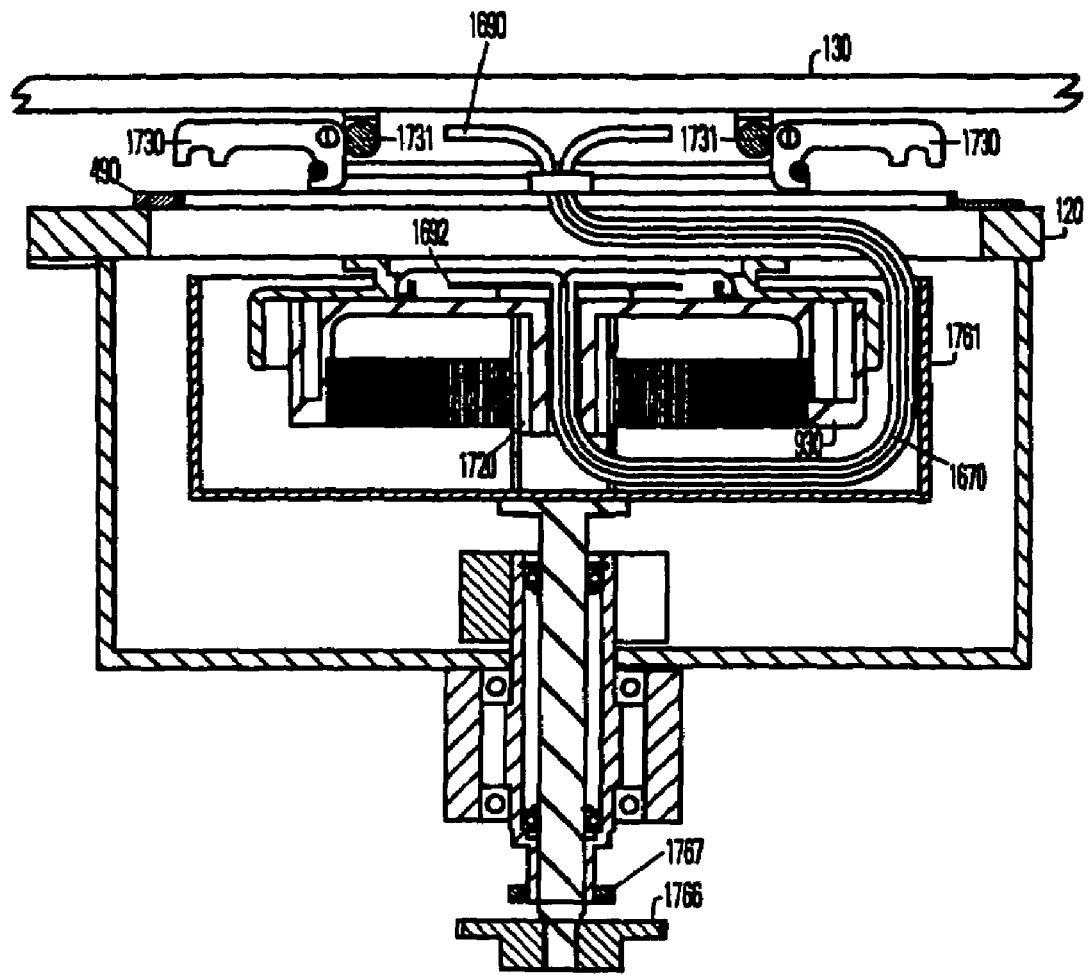
FIGS. 30A and 30B are cutaway views of an umbilical continuous flow centrifuge, in accordance with an embodiment of the present invention.
Figure 30B:
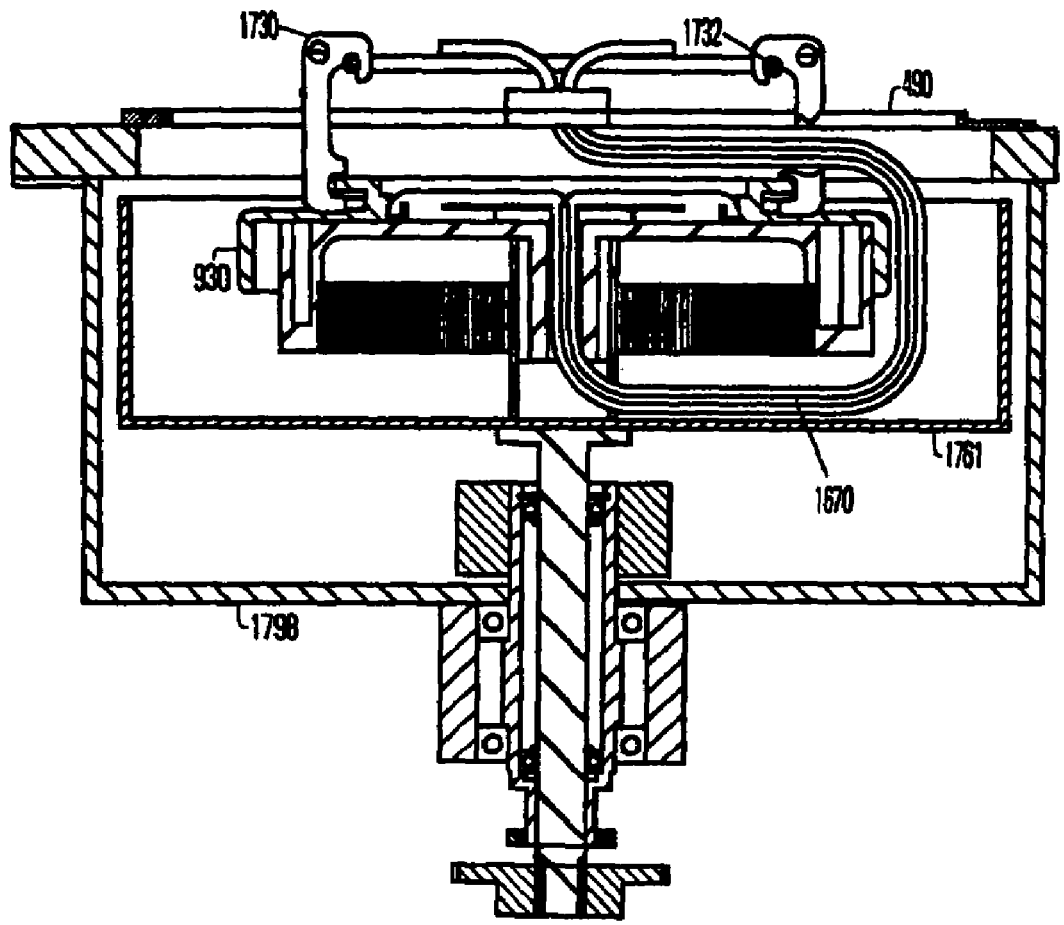
Figure 31:
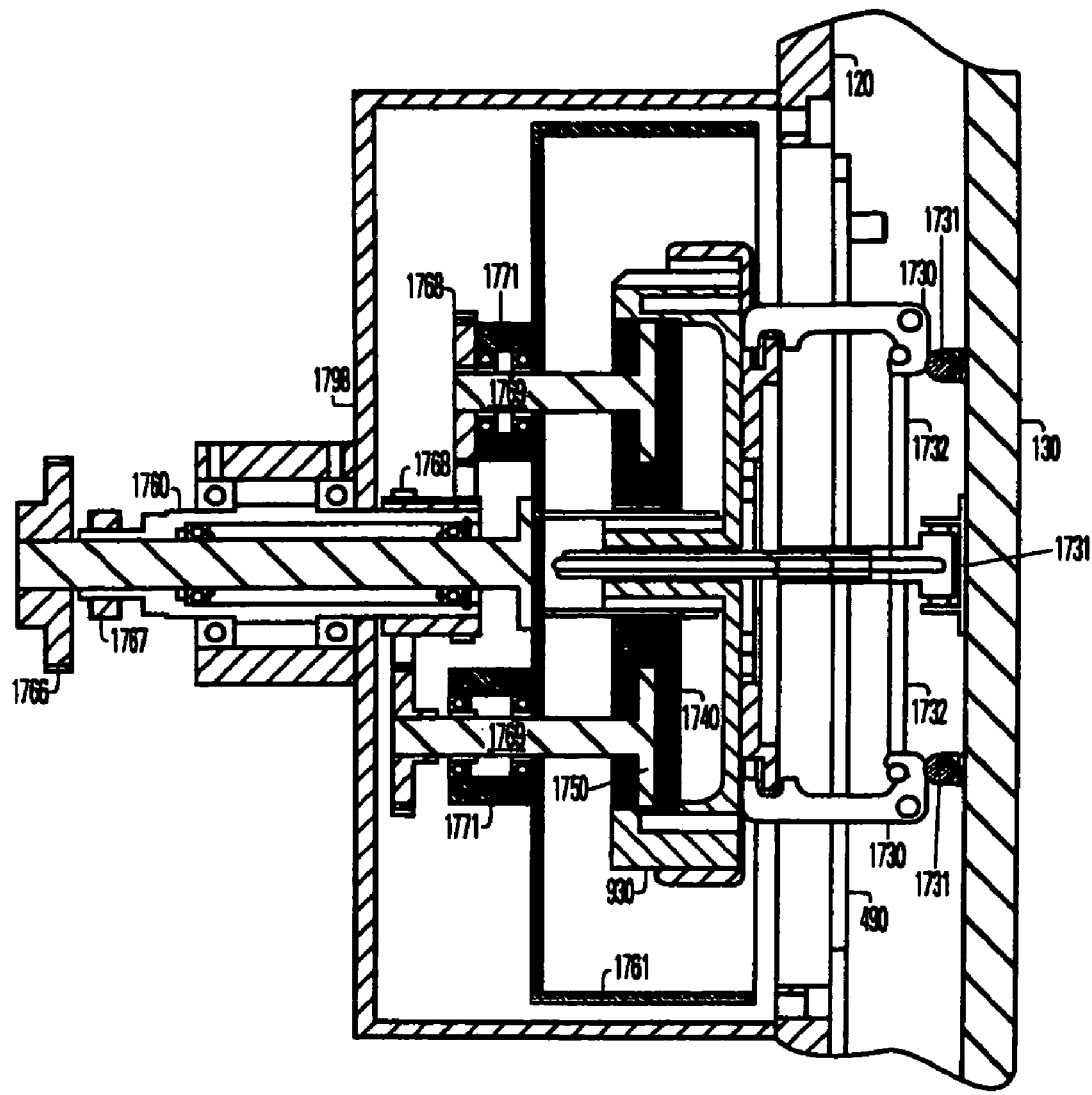
FIG. 31 is a view of an umbilical continuous flow centrifuge mounted to a console front panel, in accordance with an embodiment of the present invention.

The skiprope, also known as the umbilical, jump-rope or seal-less, approach, is the alternative to the face seal. Various apheresis systems currently use the skip-rope approach. This approach is shown conceptually in FIG. 27. The CFC disk 930, with separation channel 990, and cassette 490 are shown. The CFC disk 930 may be identical to that used in the face seal embodiment. However, in this embodiment, the means for transporting the fluid flows to and from the separation channel 990 are not ducts, as in the previous embodiment, but a flexible plastic or elastomeric umbilical 1670 connected from the rotating CFC disk 930 to the stationary cassette 490. This umbilical consists of a number of small tubes 1690, usually three to five, depending on the function to be performed, bonded or twisted together, or an extended multi-lumen tube. These tubes or lumens 1690 carry blood and fluids between the input and output ports 1692 on the disk and the cassette 490. This umbilical or skip rope 1670 is rotated about the axis or rotation 1680 of the disk at one-half the speed (RPM) of the disk itself. This keeps the umbilical from twisting or winding up. The skip-rope umbilical 1670 should be as short as possible with an outermost radius of motion around the centrifuge disk 930 of about 3 inches or as small a radius as possible. Additionally, the length of the umbilical in the direction along the axis 1680 of the centrifuge disk should be as short as possible.

As with the face seal embodiment, there is an inlet for (1) glycerolized RBCs, (2) buffy coat (with PAS), or (3) unwashed RBCs (depending on the particular embodiment of the present invention) into the CFC disk 930, and outlets for (1) deglycerolized RBCs and waste, (2) white cell product and platelet product, or (3) washed RBCs and waste, respectively, out of the CFC disk 930, along with inlet to provide other inputs, as needed (i.e., additional fluid 1032). The umbilical 1670 may use low-cost extruded PVC tubing, the diameter of which may be selected appropriately for the particular fluid that will travel therethrough. Thin walls of 0.015 to 0.03 inch may be used depending on the manufacturer and materials. The tubes are twisted together and may be adhesive or solvent bonded together.

A mechanism is necessary to provide the speed control, speed ratio, and the mechanical support for the umbilical 1670 and CFC disk 930. A major advantage of this approach is that there is no sealing interface with a potential to leak. The umbilical provides a completely closed and, once sterilized, sterile disposable set. This eliminates the possible risks of face seal leakage, particulates entering the blood from the seal, shear at the seal face, elevating face seal temperatures, and possible blood damage. The umbilical, because of its bending, twisting, and untwisting during use, possibly can heat up with time and result in blood damage. However, the short expected operating time with a maximum of 5000 RPM and good design are expected to avoid excessive heating. It will be readily recognized by one of skill in the art that the use of different materials may allow for longer operating time or faster operation without affecting the basic concepts of the invention.

The centrifuge drive mechanism, shown in FIGS. 28-31, is mounted on the front panel 120 of the console. This entire mechanism is not much larger than the centrifuge drive for a face-seal disk. The overall centrifuge mechanism ideally should be within a cylinder of less than 7 inches diameter by less than 9 inches long. The centrifuge disk 930 fits, and is locked into the drive cup 220 on the console 100, which drive cup 220 drives the centrifuge disk 930 at its required speed.

The disk 930 is supported on the 1-omega apparatus by a bearing assembly 1720 that is part of the disposable disk 930. The disk 930 is mounted or coupled to the cassette 490 in its sterile package before installation of the cassette 490 in the console 100. This simplifies cassette and disk mounting by making these two parts a single assembly mounted in one simple operation. When the cassette 490 is placed on the console front panel 120 and the door is closed, roller actuators 1731 in the door engages levers or locks 1730, biased by elastomeric element 1732, that de-mount the CFC disk 930 and allow it to rotate freely. When the door is opened, the coupling between disk and cassette 490 recurs. This makes removal a single, simple operation by handling only the cassette 490 with the disk attached to it.

Two pinion gears 1750 mounted on support bearings 1771 in the 1-omega mechanism engage an internal gear 1740 on the CFC disk 930 and drive it at 2-omega. These gears are mounted on two short shafts 1769 that are secured at 180 degrees apart to the umbilical drive cup 1761. This cup 1761 is driven at 1-omega by the internal shaft of dual concentric drive shafts 1760.

The dual concentric drive shafts 1760 have attached pulleys that are belt driven from two pulleys 1766, 1767 mounted on an electric motor shaft. The internal shaft of the two concentric drive shafts 1760 drives the umbilical drive cup 1761, which couples with and drives the umbilical at 1-omega.

The external tubular concentric shaft has two pulleys mounted to it that belt drive 1768 the two short shafts 1769 secured to the umbilical drive cup 1761. These shafts are secured but rotate freely in bearing assemblies 1771 that are part of or attached to the umbilical drive cup. These shafts have pinion gears 1750 that engage an internal ring gear 1740 that is part of the CFC disk 930. One such shaft and gear is adequate to directly drive the CFC disk 930, but two at 180 degrees apart are used for balance and safety via redundancy.

The concentric drive shafts rotate within a bearing block 1797 that is mounted to stationary hollow cylinder 1798 with one flat end. This cylinder 1798 is attached to the console front plate 120 and supports thereby the entire mechanism.

Figure 32:
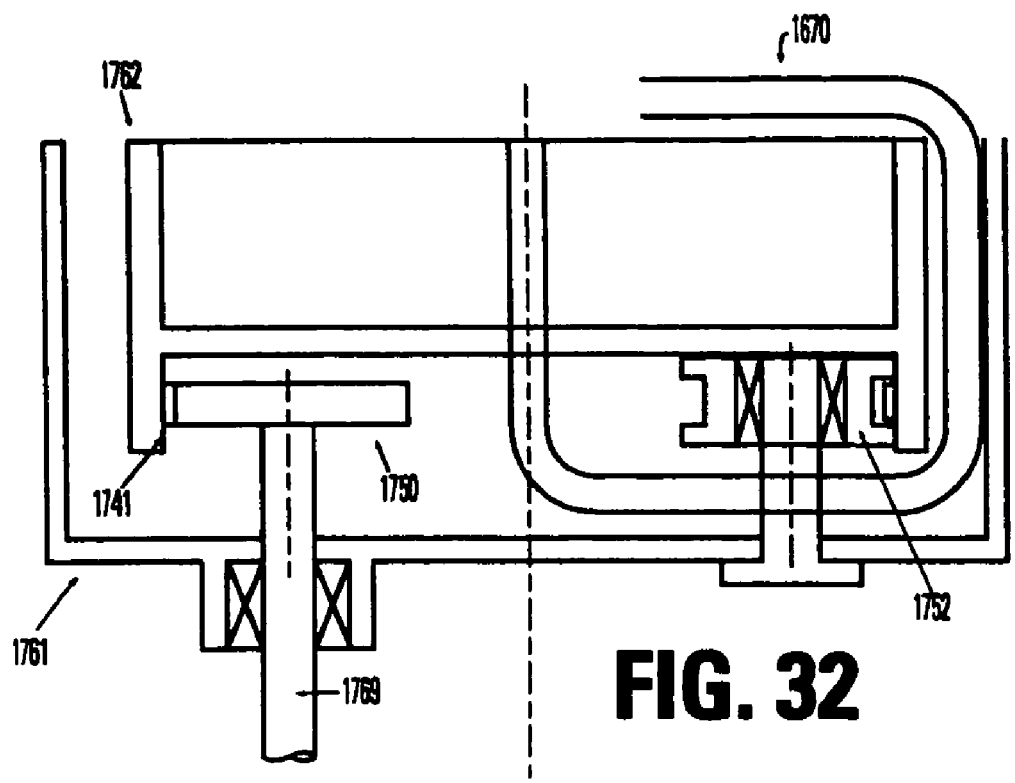
FIG. 32 is a conceptual representation of an alternative umbilical design, in accordance with an embodiment of the present invention.
Figure 33:
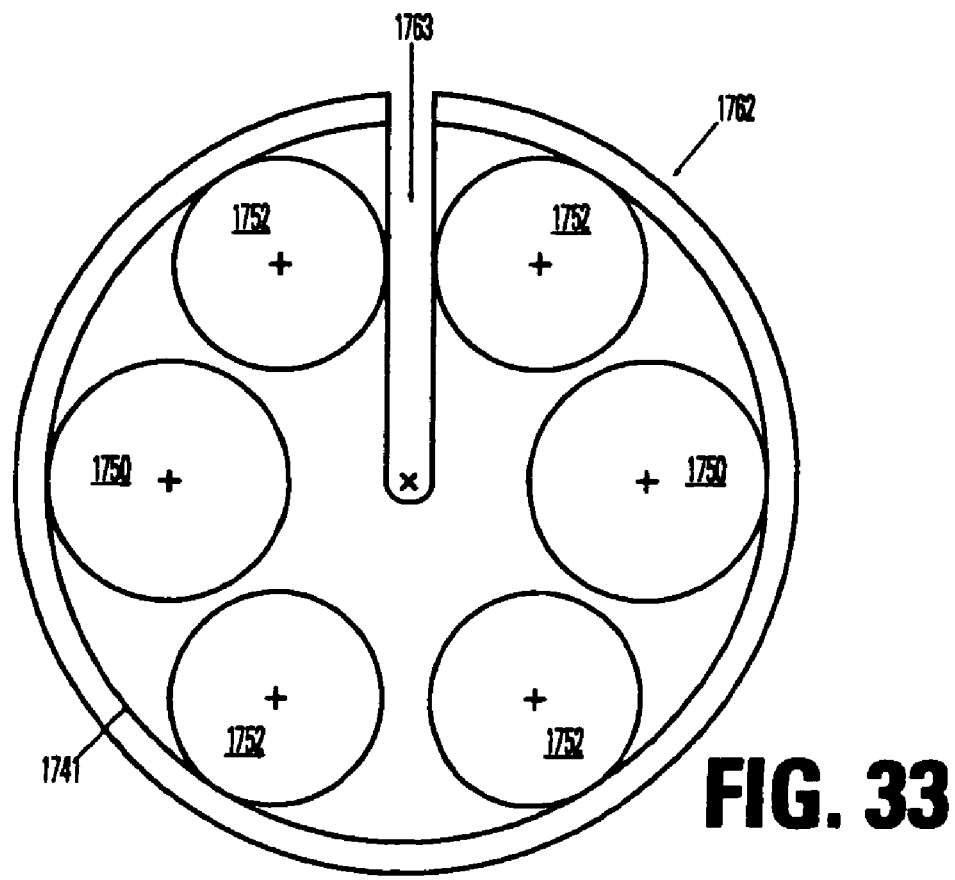
FIG. 33 is a conceptual representation of a gear and bearing arrangement of an embodiment of the umbilical continuous flow centrifuge depicted in FIG. 32, in accordance with an embodiment of the present invention.

As another alternative, shown conceptually in FIGS. 32 and 33, rather than engaging an internal gear 1740 on the CFC disk itself, the pinion gears 1750 engage a similar internal gear 1741 on a disk drive cup 1762, which is mounted in the umbilical drive cup 1761. Toothless rotor support bearings 1752 provide additional stability and centering of the disk drive cup 1762. The disk drive cup includes a slot 1763 to allow the umbilical to be placed into the umbilical drive cup. The disk drive cup may then include pins 225 as described in connection with the cup 220 to hold the centrifuge disk in the cup when in operation. Persons of ordinary skill in the art will appreciate that other design alternatives are possible, including an external gear on the disk drive cup (or the CFC disk) surrounded by the drive gears and/or support bearings.

To reduce noise, gears and support bearings may be plastic or elastomeric.

Operation of a Continuous Flow Centrifuge

In various embodiments of the instant invention, the CFC may be used to: (1) separate glycerolized RBCs into deglycerolized RBCs and waste product (i.e., a volume of glycerolizing solution plus some plasma and red cell storage solution), (2) separate buffy coat (with PAS) into white cell product and platelet product, and (3) separate unwashed RBCs into washed RBCs and waste product. The operation of the CFC is substantially similar in each embodiment; various blood products and/or liquids are separated by weight via centrifugation. It will thus be readily understood by those of skill in the art that the following description of the operation of the CFC with respect to the separation of a glycerolized RBCs into deglycerolized RBCs and waste product is substantially similar to the operation of the CFC with regard to the separation of alternate blood products.

Figure 34:
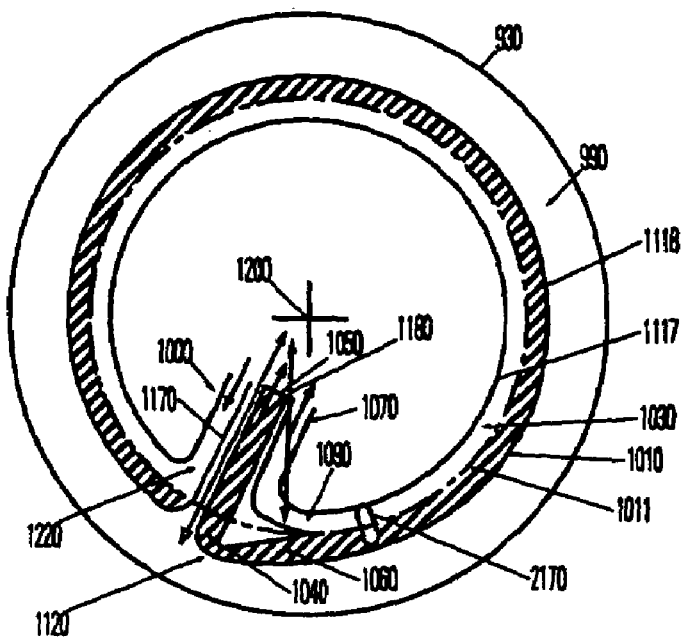
FIG. 34 depicts a conceptual design for a continuous centrifuge disk separation channel, in accordance with an embodiment of the present invention.

The separation of glycerolized RBCs into deglycerolized RBCs and waste product in a CFC will now be described. The compact, disposable CFC disk 930 is designed to provide blood product separation into various components within an annular separation channel 990 and to remove these components from the channel and disk, meeting the various requirements for flow rate, hematocrit, blood component damage, and the like. A conceptual design of the CFC disk 930 is shown in FIG. 34. Glycerolized RBCs are pumped into the CFC disk 930 via the entry duct 1000 and through an input port 1220 while the disk rotates around the axis 1200 at sufficient speed to rapidly separate incoming glycerolized RBCs into deglycerolized RBCs and waste product. The centrifuge disk 930 has an annular separation channel 990 near its outer periphery. Glycerolized RBCs flow continuously into this separation channel 990, separating into components as the glycerolized RBCs flow along the channel, and the components are removed at various ports along the channel. Deglycerolized RBCs 1010 are separated to the outer (larger diameter) wall of the separation channel 990, and waste product 1030 separates to the inner wall 1117 of the channel. The deglycerolized RBCs 1010 and waste product 1030 are removed continuously through ports and ducts to product bags.

The separation channel 990 is shaped to improve the separation and removal of deglycerolized RBCs 1010 and waste product 1030. The channel outer wall 1118 increases in radius (from the axis of rotation 1200) in one region to be at or near its maximum distance or radius 1170 from the axis of rotation 1200 and thus form a collection pocket portion 1060 for deglycerolized RBCs. The red cell pick-up port 1120 removes red cells at or near the bottom or largest radius 1170 of this pocket, at the greatest distance from the center of rotation. This increased radius increases the depth of the red cell layer (the radial distance from the red cell-waste product interface 1130 to the red cell pick-up port) and provides the maximum g-force and packing of red cells at this port. This maximizes the packed red cell hematocrit that can be achieved for cells removed through the red cell pick-up port at any given rotational speed of the disk. The deep red cell layer also minimizes the pulling of waste product 1030 through this layer to the red cell pick-up port.

Figure 35:
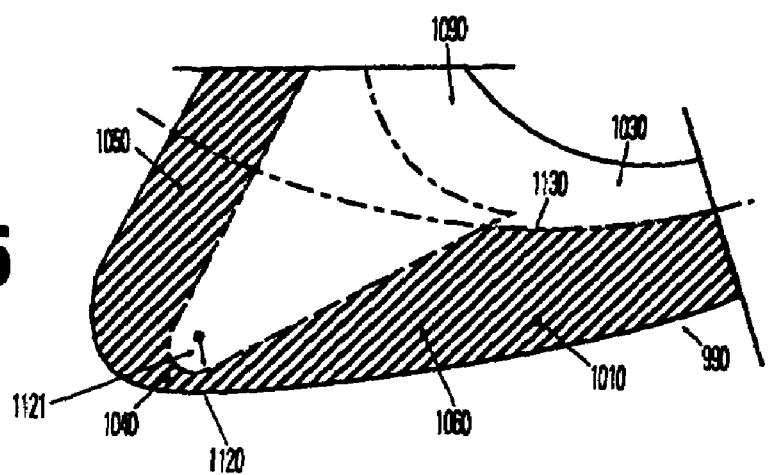
FIG. 35 depicts, conceptually, a detail of a separation channel, in accordance with an embodiment of the present invention.
Figure 36:
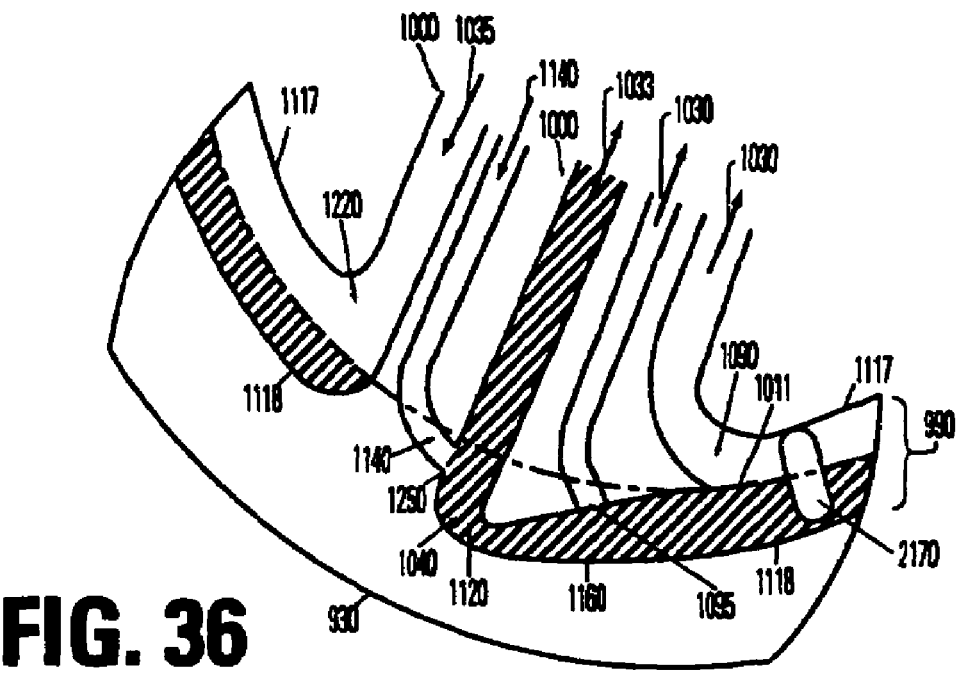
FIG. 36 depicts a detail of a continuous flow centrifuge separation channel with two plasma pickup ports, in accordance with an embodiment of the present invention.

FIGS. 35 and 36 show designs for the packed red cell removal region. A narrow gap 1120, of a width substantially less than the average radial width of the separation channel 990, and generally between 10 to 30 mils, is provided over part or all of the separation channel 990, at the deepest, that is the largest radius 1170 from the spin axis 1200, part of the channel and of the red cell collection pocket portion 1060. This gap 1120 is used to pull red cells from the deepest part of the pocket where they are most highly packed, to a high hematocrit (about 90%). This narrow gap 1120 ensures that red cells are removed from the highest hematocrit region of the concentrated red cells 1010. The gap is narrow enough to cause a slight restriction and ensure that lower-hematocrit red cells or waste product 1030 from near the red cell-waste product interface 1130 does not channel through the concentrated red cells 1010 and out this removal port. The radial distance from the red cell-waste product interface 1130 to the packed red cell removal port 1040 is made sufficiently great to prevent such channeling and maximize red cell hematocrit.

The length of this gap is maximized in the axial direction, that is, essentially parallel with the axis of rotation, so that the flow velocities are low, to avoid damage to the red cells. Further, the entrance to the gap may be defined by material having a radius 1121 that is greater than or equal to the width of the gap 1120 to prevent damage to the red cells and reduce the pressure drop.

The channel inner wall 1117 may decrease in radius 1180 from the axis of rotation 1200 to form a waste product pocket portion 1100 where waste product 1030 can flow through an output port 1090 into a substantially radial waste product removal duct 1070, which can include other fluid transportation means such as a tube, that transports the waste product toward the center of the disk 930 for removal to the cassette 490. The decreasing radius at an increasing cross-sectional area for waste product flow results in a reduced waste product flow rate and the final opportunity for stray cells to separate out of the plasma stream before waste product 1030 is removed.

Figure 38A:
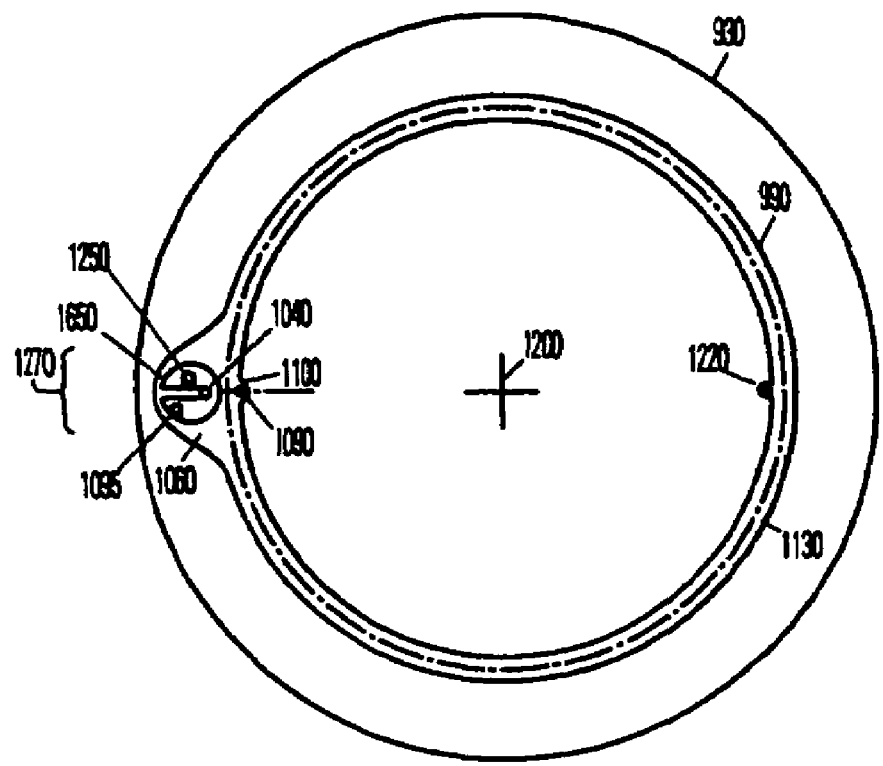
FIGS. 38A and 38B depict a continuous centrifuge disk with a second design for a separation channel, in accordance with an embodiment of the present invention.
Figure 39:
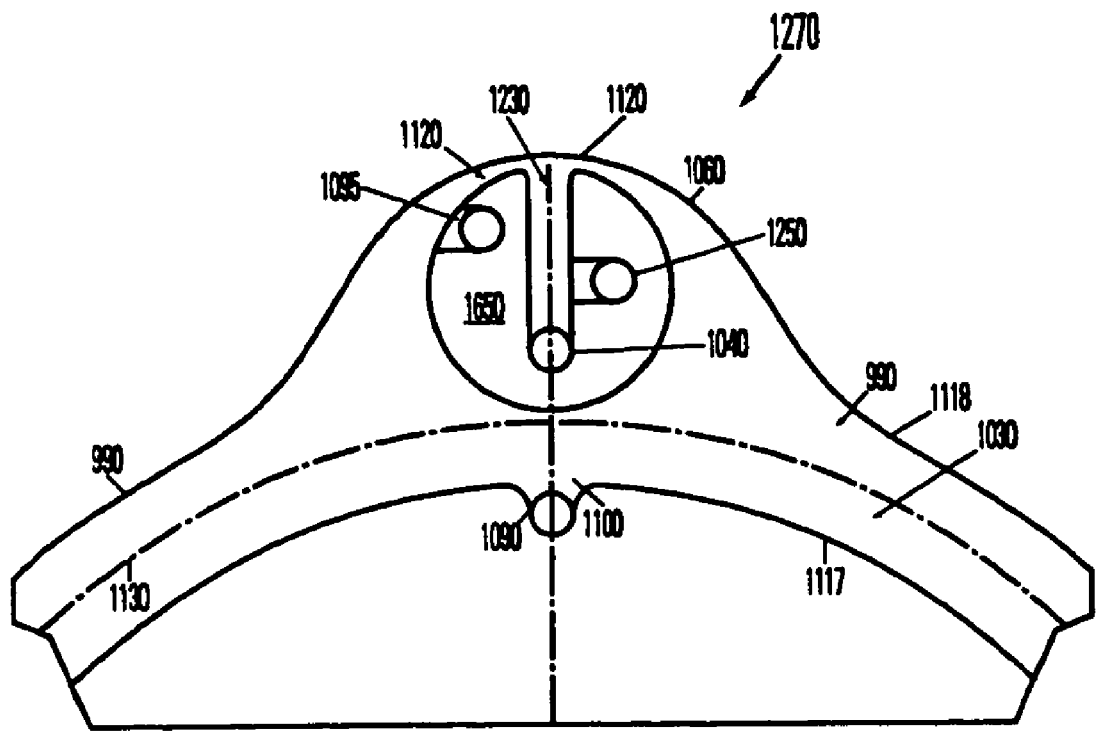
FIG. 39 depicts a conceptual detail for a third design for a separation channel, in accordance with an embodiment of the present invention.

Once the operation is complete, the system must be purged. There are several ways of performing this task. In the first method, plasma 1030 is removed from the plasma removal duct 1070 during steady-state continuous flow operation. When the blood processing operation is complete, the separation channel 990 is filled with separated blood. The red cell pump 701 continues to remove red cells from the red cell collection pocket portion 1060 until all red cells are removed while disk rotation continues at a high speed. Plasma 1030 is allowed to flow back from the plasma bag and fills the separation channel 990. The separation channel 990 is now filled with plasma 1030. However, there are residual red cells loosely adhering to the walls of the separation channel 990. This prevents draining the plasma 1030 out the plasma removal duct 1070 while slowly rotating the disk because the residual red cells will mix with this plasma and overly contaminate it. It is also not feasible to pump the plasma 1030 out of the concentrated red cell removal duct 1050 because this duct is filled with red cells. An excessive amount of plasma would be needed to clear out or purge the red cells sufficiently to avoid excessive red cell contamination of the plasma 1030. Therefore, as shown in FIGS. 38A and 39, a second plasma removal duct 1080 and port 1095 may be added to the disk 930 specifically to remove plasma 1030 during the purge process when the separation channel 990 is filled with plasma 1030. In the embodiment shown, the second plasma removal port is added in an "island" 1650 near the red blood cell "pocket" portion 1060 of the separation channel 990. The disk 930 is rotated at a moderate speed and sterile air, which was collected in an air bag 1110 during disk priming, is used to replace the plasma 1030 in the separation chamber as plasma 1030 is removed through the second plasma removal port 1095. The air pressure may be great enough to force the plasma 1030 out of the disk or a pump may be used to pull the plasma out of the disk.

The separation channel design, including the location of ducts, and disk rotational speed are key to achieving the desired separation requirements. FIGS. 37, 38, 42, 43, 44 and 45 show various alternative designs for the substantially circular separation channel, in that the axis of rotation 1200 is the center of a circle approximately defined by those portions of the separation channel that are not in the pocket portions 1060, 1100. It is not necessary, however, that the separation channel extend for a full 360 degrees, or that the channel be unbroken, although as noted below, such a design may have certain advantages.

In all the designs, the glycerolized RBCs enter the separation channel at a port 1220, concentrated (deglycerolized) red cells 1010 are picked up in port 1040 from a pocket portion 1060 positioned at the largest radius 1170 or point furthest from the axis of rotation 1200, and waste product removed at the port 1090 at the other end of the separation channel 990.

In all of the designs a variety of radial fluid conduits 1001 may be used. For example the ducts 1070, 1050, 1251 and 1000 may be machined in the disk body 1150 substantially extending toward the center of the disk 930. The ducts are sealed at 1151 by the disk cap 1500. These fluid ducts carry glycerolized RBCs to the separation channel 990 from the central face seal. Waste product and concentrated (deglycerolized) red cells are carried by these ducts from the separation channel 990 to the face seal. Alternatively, tubing is used in the skip rope CFC design, but tubing may also be used as a radial fluid conduit in the face seal design.

Figure 38B:
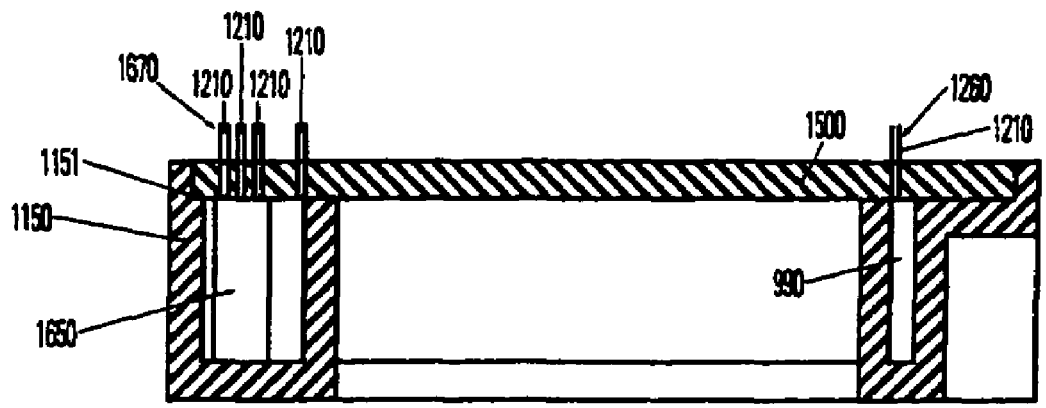

FIGS. 38A, 38B and 39 illustrate a CFC disk 930 specifically designed for umbilical tubing 1210 attachments. Glycerolized RBCs enter at the entry port 1220 through a tube 1260 which is connected to the separation channel 990 and which is 180° away from the component removal region 1270. Glycerolized RBCs are divided into two paths that are on either side of the tube 1260. This reduces (by half) the flow rate in each 180° channel segment and may improve red cell-waste product separation. Concentrated red blood cells 1033 are channeled through a pocket formed by an island 1650 in the separation channel 990 and through narrow gap 1120 into a slot 1230 formed in the island 1650 with an opening toward the outer wall 1118 of the separation channel 990. The slot entrance does not extend the entire axial length of the separation channel, that is, in the direction parallel to the axis of rotation. Generally, the slot represents 50% to 90% of the length. Alternatively, holes can be placed at the entrance rather than a slot. Waste product is removed through a removal port 1090 during steady-flow, which may be positioned on the inner wall 1117 of the separation channel 990 as shown, or alternatively (not shown) on that portion of the island 1650 closest to the inner wall. Umbilical tubing 1210 attaches to the ports at or near the entry port 1220 and the component removal region 1270. However, ducts to a face seal as described above can also be used instead of an umbilical, with the same separation channel and component removal design features.

Figure 42:
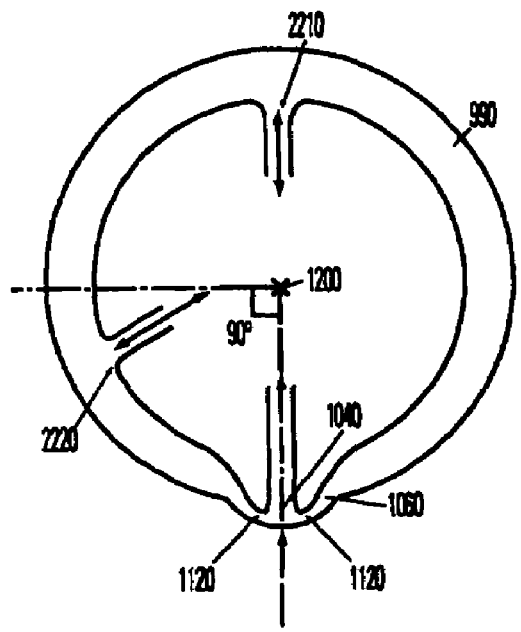
FIG. 42 depicts a continuous centrifuge disk with a fourth design for a separation channel, in accordance with an embodiment of the present invention.
Figure 43:
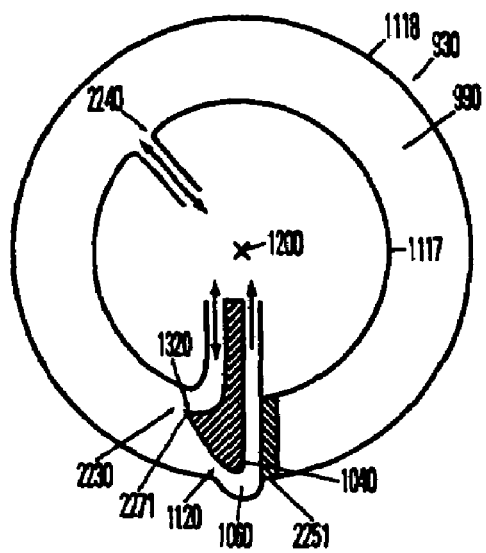
FIG. 43 depicts a continuous centrifuge disk with a fifth design for a separation channel, in accordance with an embodiment of the present invention.
Figure 44:
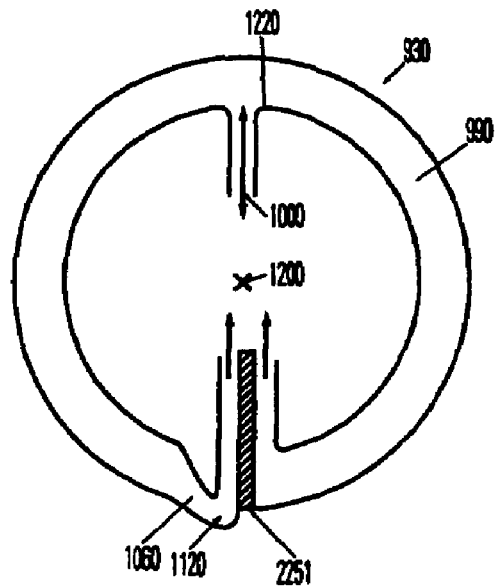
FIG. 44 depicts a continuous centrifuge disk with a sixth design for a separation channel, in accordance with an embodiment of the present invention.

FIGS. 42, 43 and 44 show alternative designs for a circular separation channel 990. Each of these embodiments has radial inlet and outlet ducts. FIG. 42 shows a CFC disk 930 with features such as a collection pocket portions 1060 and narrow gaps 1120. The system can be designed such that glycerolized RBCs enter at a port at point 2210, 180° from the removal port 1040 and waste product is removed at a port at point 2220 at an angle less than 90° from the glycerolized RBC removal port 1040, or alternatively, glycerolized RBCs can enter at point 2220 and waste product can be removed at point 2210.

The embodiment of FIG. 43 also includes two ports that may alternatively be used for waste product removal or glycerolized RBC introduction depending upon the connections made to the manifold. One port is positioned at point 2230 adjacent and parallel to a red blood cell removal port 1040, while the other port at point 2240 is positioned at an angle of from 90 to 270 degrees relative to the red blood cell removal port 1040. An internal barrier wall 2251 is positioned adjacent and parallel to the red blood cell removal port 1040, but on the opposite side of the red blood cell removal port 1040 from point 2230. The embodiment may also include a red blood cell collection pocket 1060 and gap 1120, and may also include a knife edge diverter 1320 which is further described below.

In FIG. 44, a glycerolized RBC entry port 1220 is positioned 180 degrees from the red blood cell removal port 1040. A waste product removal port 1090 is positioned adjacent and parallel to the red blood cell removal port 1040. The two ports are separated by an internal barrier wall 2251. As with the embodiment shown in FIG. 43, a narrow gap 1120 and pocket portion 1060 may be included to assist in the separation of the concentrated red blood cells 1033.

Figure 45A:
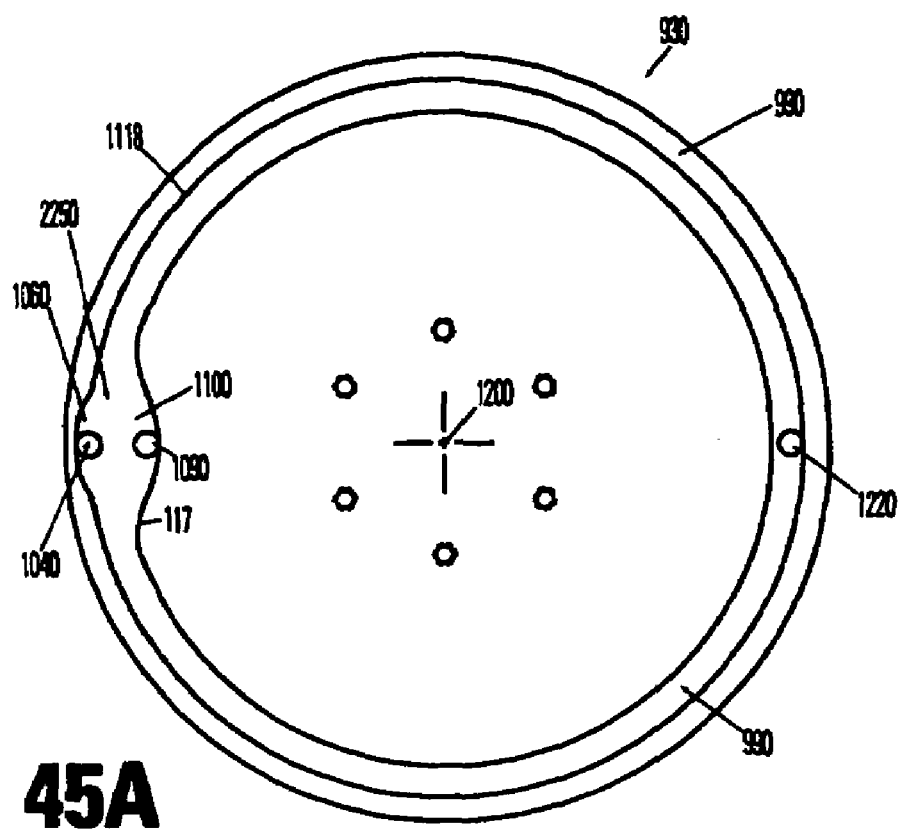
FIGS. 45A and 45B depict a continuous centrifuge disk with a seventh design for a separation channel, in accordance with an embodiment of the present invention.
Figure 45B:
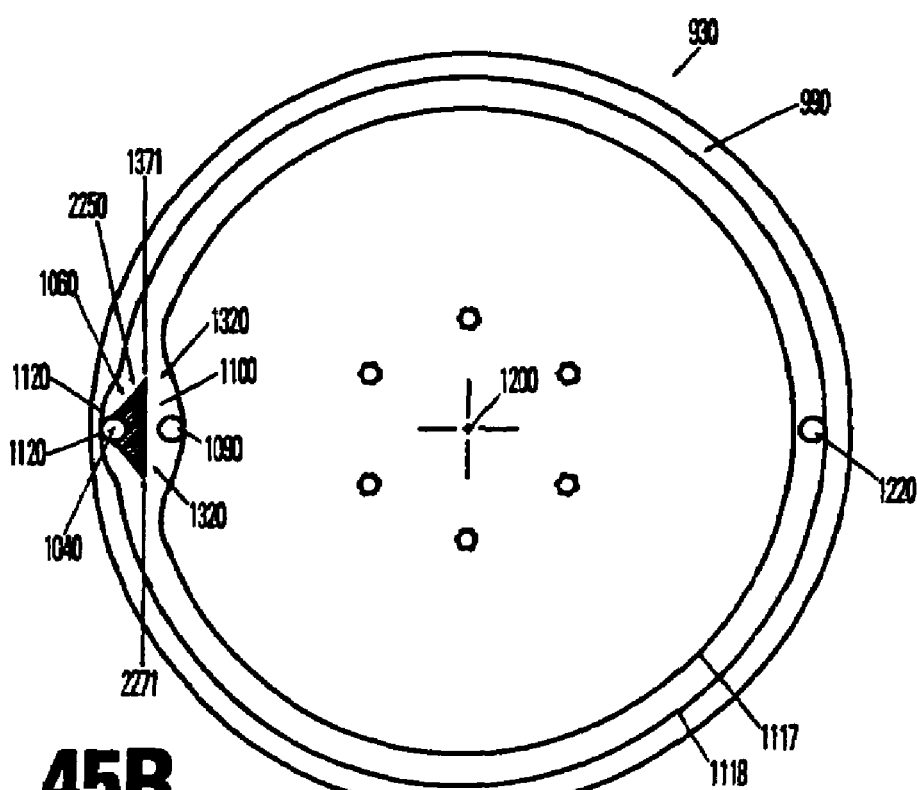

Finally, in FIGS. 45A and 45B, a circular separation channel 990 without a barrier is used. The red blood cell removal port 1040, in a pocket portion 1060 formed in the outer wall 1118 is positioned 180 degrees from the glycerolized RBC entry port 1220. Also at 180 degrees from the glycerolized RBC entry port 1220, but positioned in a pocket portion 1100 in the inner wall 1117, is the waste product removal port 1090. This design has similar advantages to the design shown in FIG. 38; for example, glycerolized RBCs are divided into two paths at the glycerolized RBC entry port 1220 reducing by half the flow rate in each 180° channel segment and potentially improving red cell-waste product separation. Optionally, as shown in FIG. 45B, an island structure 2250 may be used. The island structure 2250 allows the formation of narrow gaps 1120 near the entrance to the red blood cell removal port 1040.

Figure 37:
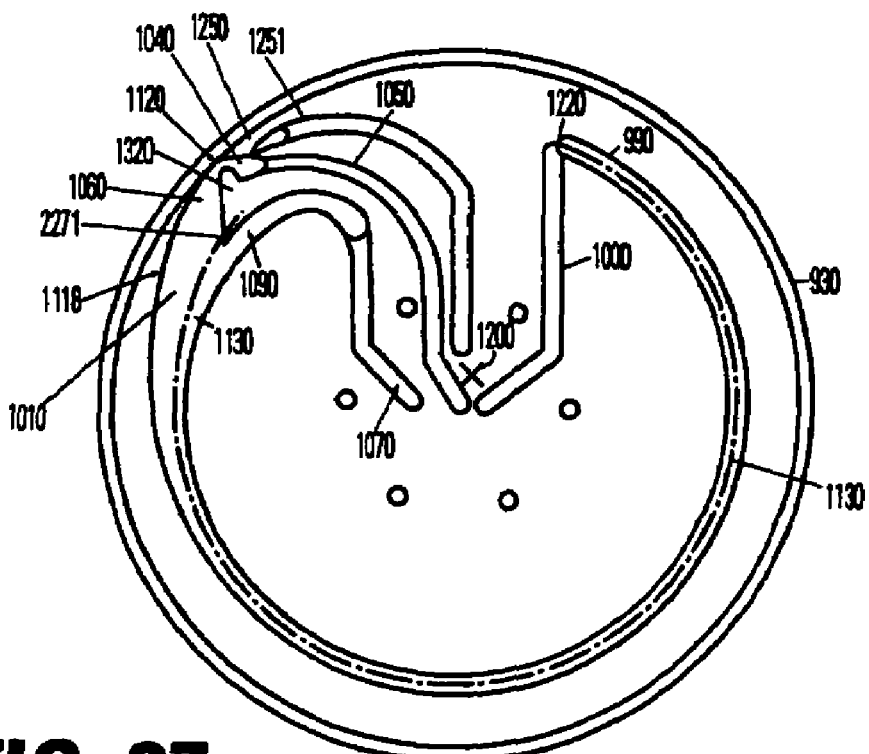
FIG. 37 depicts a continuous centrifuge disk with a first design for a separation channel, in accordance with an embodiment of the present invention.

In all designs in which an island structure 2250 or an extension from the inner wall 1117 is practical, a knife edge diverter 1320 may be used to separate waste product from the concentrated red cells 1010. The point 2271 of the knife edge diverter 1320 maybe at a slightly smaller radius from the center of rotation 1200 than the radius of the red cell-waste product interface 1130, as shown in FIG. 37. The waste product in the channel from this diverter 1320 to the waste product pick-up 1090 spirals or steps inward to ensure only waste product is in this channel; red cells will separate out from waste product in this channel segment and move upstream under centrifugal forces to return to the channel segment containing red cells.

Figure 46:
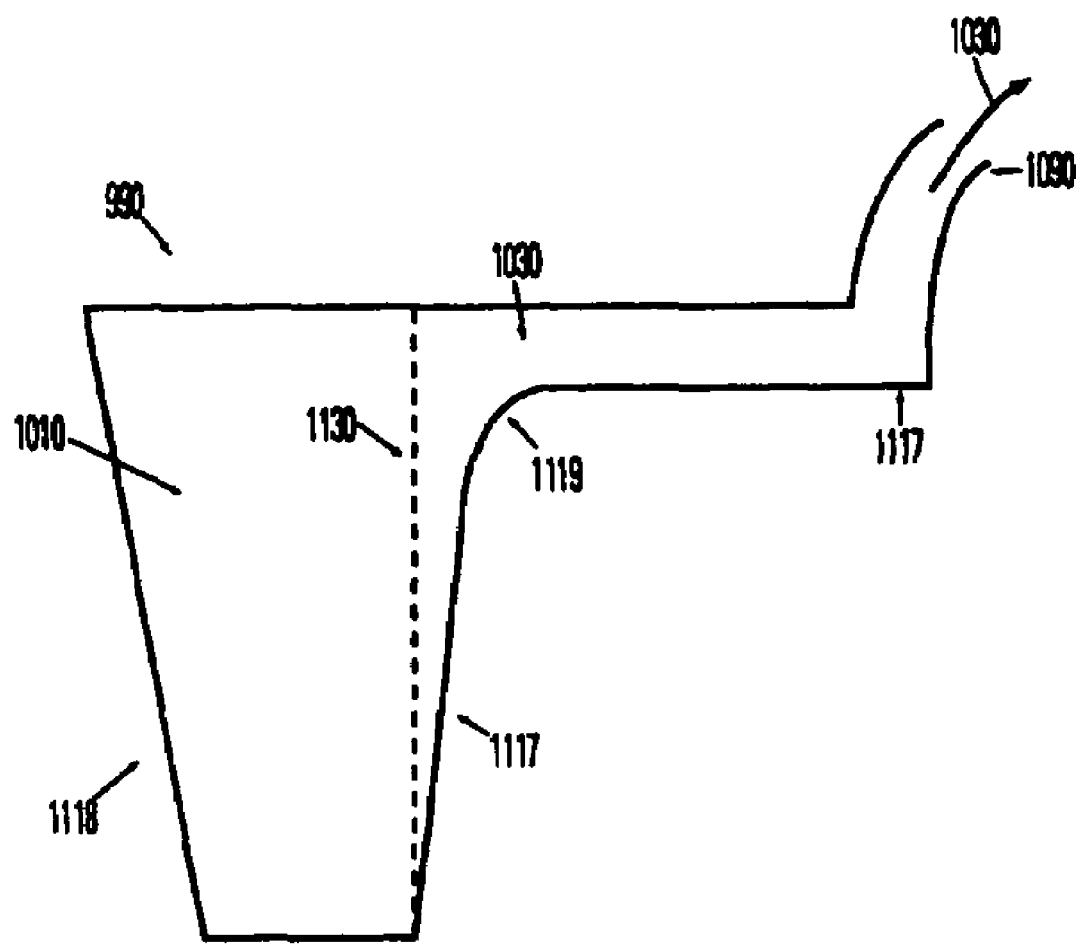
FIG. 46 depicts a conceptual representation of a channel design, in accordance with an embodiment of the present invention.
Figure 47A:
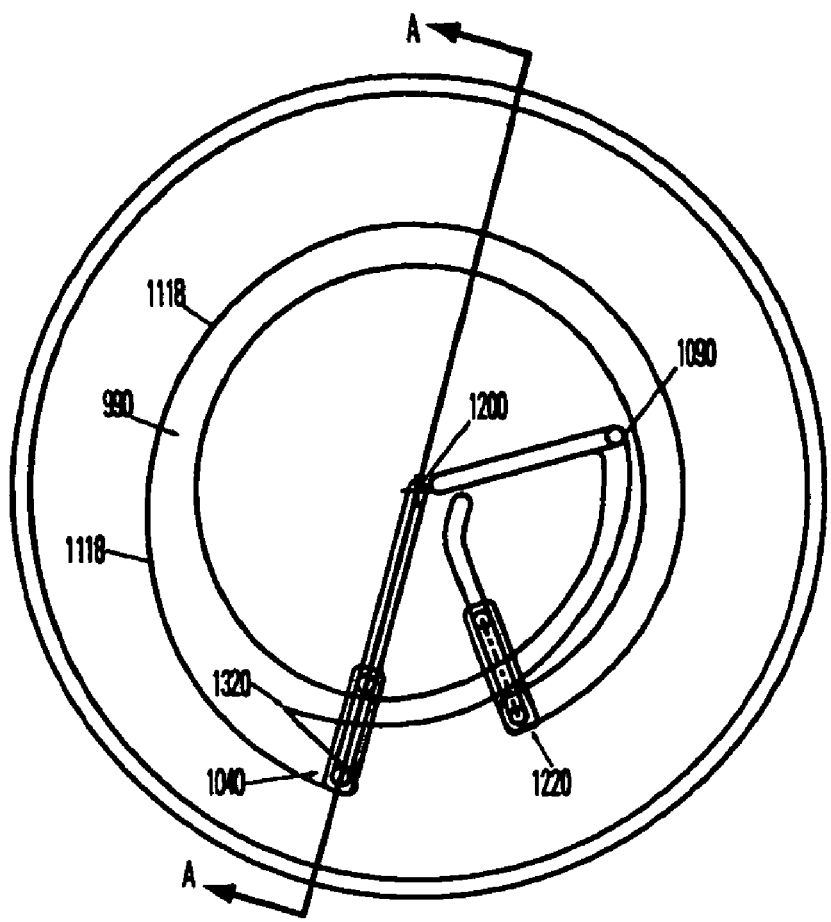
FIGS. 47A and 47B depict an eighth separation channel design, in accordance with an embodiment of the present invention.
Figure 47B:
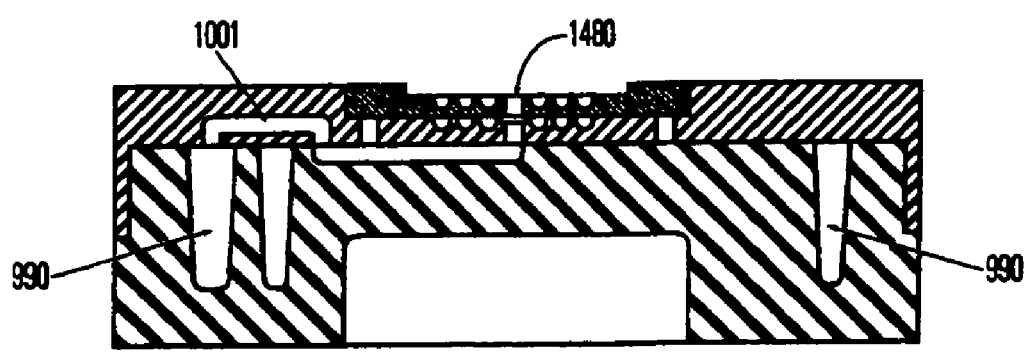

With reference to FIGS. 38B and 47B, current standard designs for separation channels usually have inner and outer walls 1118 that are substantially parallel with each other as shown in 38B, or slightly tapered, as shown in FIG. 47B. However, control can be improved; for example in the purging process, by utilizing a cross-sectional shape similar to that shown in FIG. 46. The walls of the separation channel are generally tapered, and the channel 990 becomes substantially "shallower" at the inner wall 1117, as the inner wall 1117 forms a rounded edge 1119. By placing the waste product removal port 1090 within the shallower section of the inner wall 1117, and the red blood cell removal port at the "deeper" section of the channel 990 and at the outer wall 1118, mixing or contamination of waste product 1030 and red blood cells 1010 is less likely, given the position of the waste product-red blood cell interface 1130 relative to the channel and the ports.

Figure 40A:
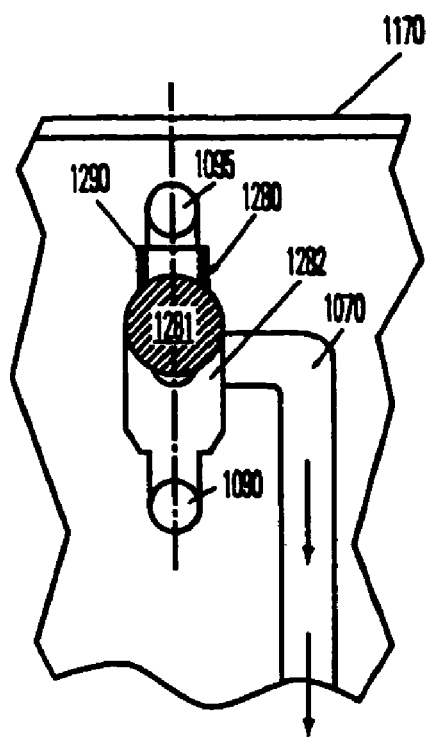
FIGS. 40A and 40B depict a design for a plasma port that includes a ball valve in a first position, in accordance with an embodiment of the present invention.
Figure 40B:
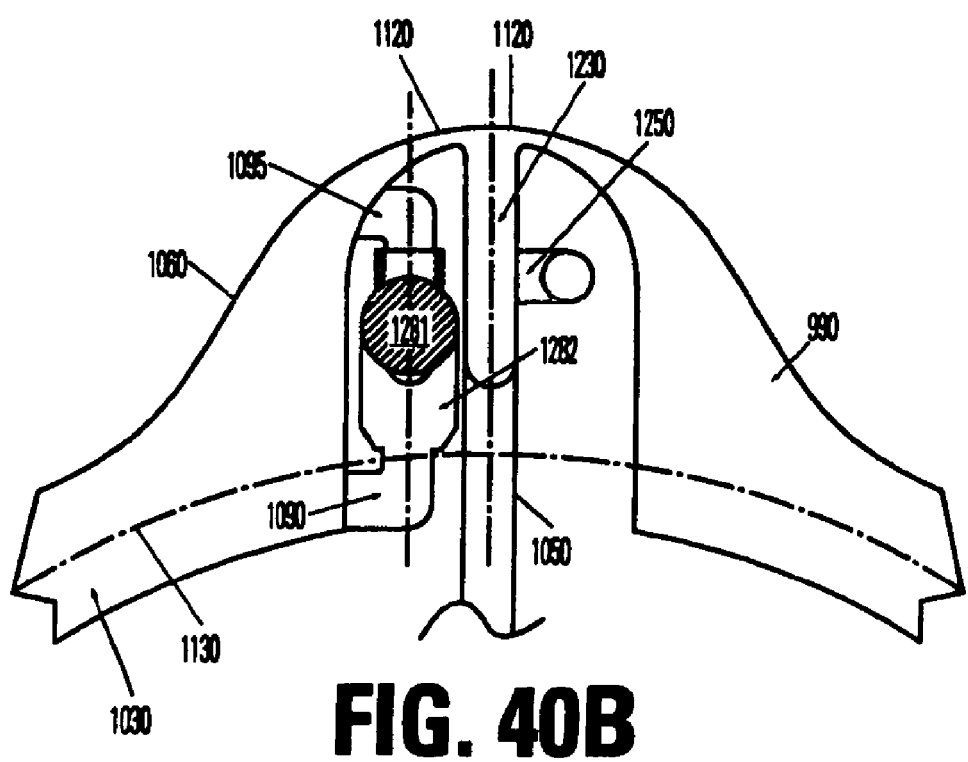

An alternative design for the removal of waste product in the separation channel 990, one during steady flow and one during the purge, is shown in FIGS. 40 and 41. A spring-loaded 1290 ball shuttle valve 1280 is used to control which port 1090, 1095 removes waste product. The ball shuttle valve 1280 includes a ball 1281 attached to a spring in a housing 1282 with three openings. One opening is attached to the waste product removal port 1090 for continuous flow, while another is connected to the waste product removal port 1095 for purging. The third opening is connected to a waste product removal duct 1070 or similar structure. During steady state continuous flow operation shown in FIG. 28, the CFC disk RPM is high (perhaps 4000 to 5000 RPM) and the g-forces on the ball 1281 compress the spring and close the purge port, with the steady flow port open to remove waste product 1030.

Figure 41A:
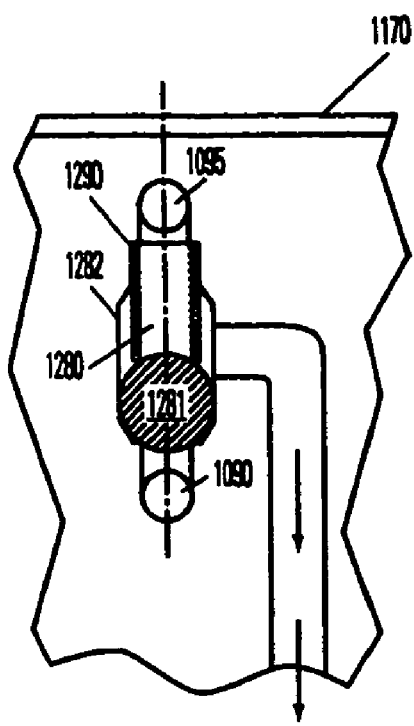
FIGS. 41A and 41B depict a design for a plasma port that includes a ball valve in a second position, in accordance with an embodiment of the present invention.
Figure 41B:
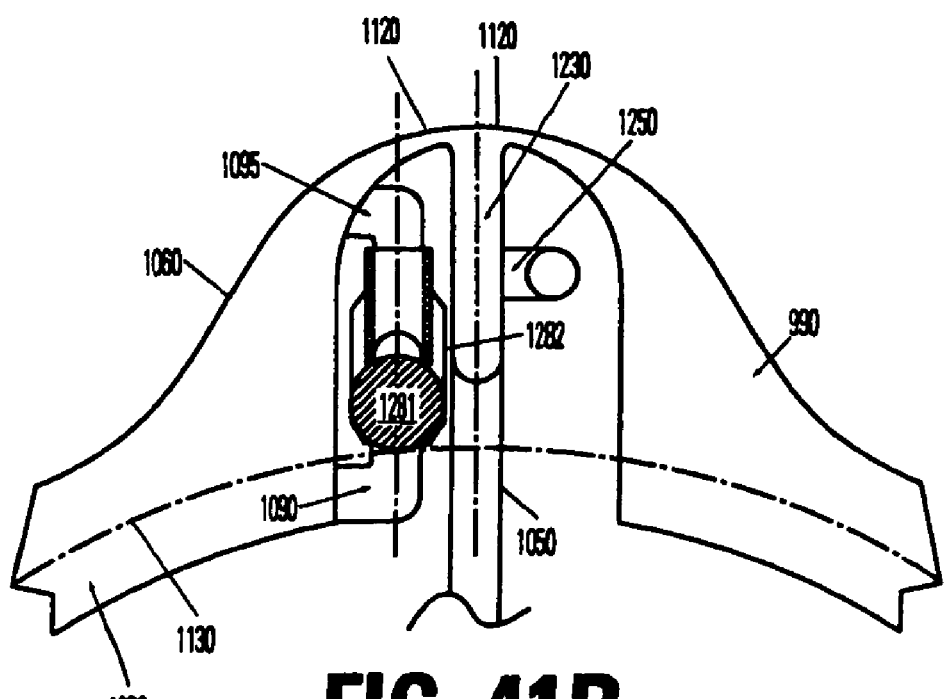

During the purge shown in FIGS. 41A and 41B, the RPM is dropped substantially (to perhaps 1000 RPM). This permits the spring force to overcome the g-force. The ball shuttle valve 1280 thus closes the steady flow port 1090 and opens the waste product purge port 1095. The waste product 1030 is either pumped out during the purge, or the pressure of air (entering the separation channel and displacing waste product) is used to force the waste product out as was described above in other embodiments.

It is not necessary that the separation channel be centered on the axis of rotation of the disk or be circular. FIGS. 47A and 47B show a separation channel 990 that extends about 420 degrees. This channel 990 may, as shown, have an outer wall 1118 spiral of increasing radius from the glycerolized RBC entry port 1220 to concentrated red cell pick-up at port 1040, and the channel may be of decreased radius from the glycerolized RBC entry port 1220 to collect waste product at port 1090. The design may optionally include other features discussed above, such as a knife edge diverter 1320.

Figure 48A:
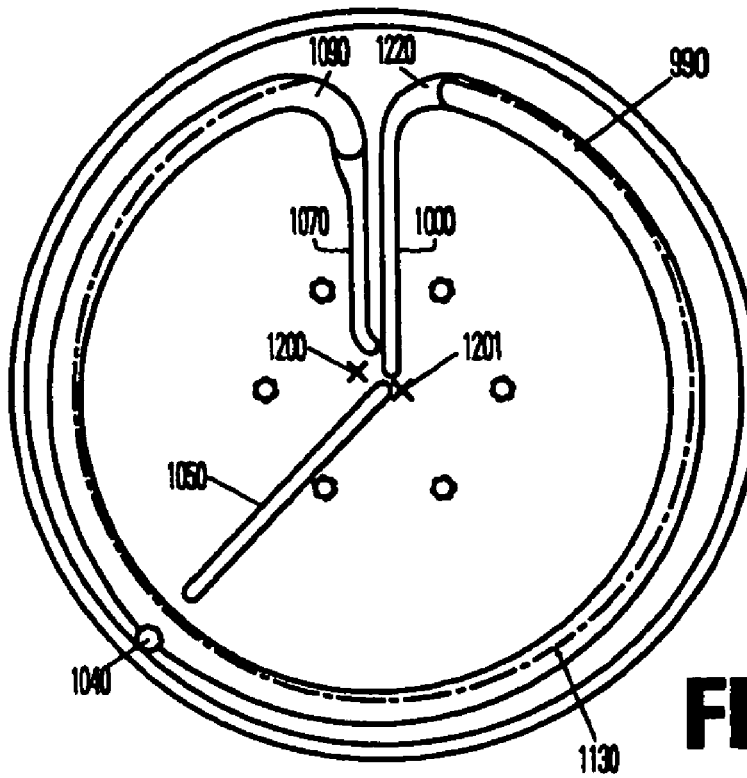
FIGS. 48A and 48B depict a ninth separation channel design, in accordance with an embodiment of the present invention.
Figure 48B:
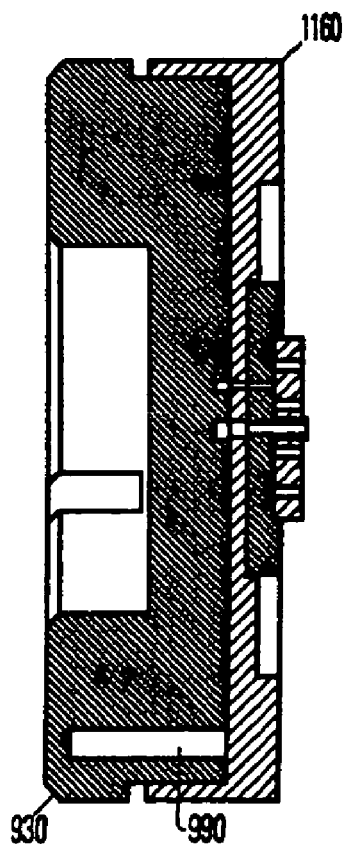

FIG. 48 shows a CFC disk 930 with a slightly spiral separation channel 990 that extends approximately 360° around the CFC disk 930 periphery. The design is substantially circular in that is it is based on a circle 1190, but unlike the circular embodiments described above, the centerpoint of the circle 1201 that is defined by the separation channel 990 is offset from the axis of rotation 1200, and the channel 990 may spiral inward slightly at the waste product port 1090. In some cases, the inward spiral may be continued past 360° to form two concentric separation channels for a portion of the disk.

Figure 49:
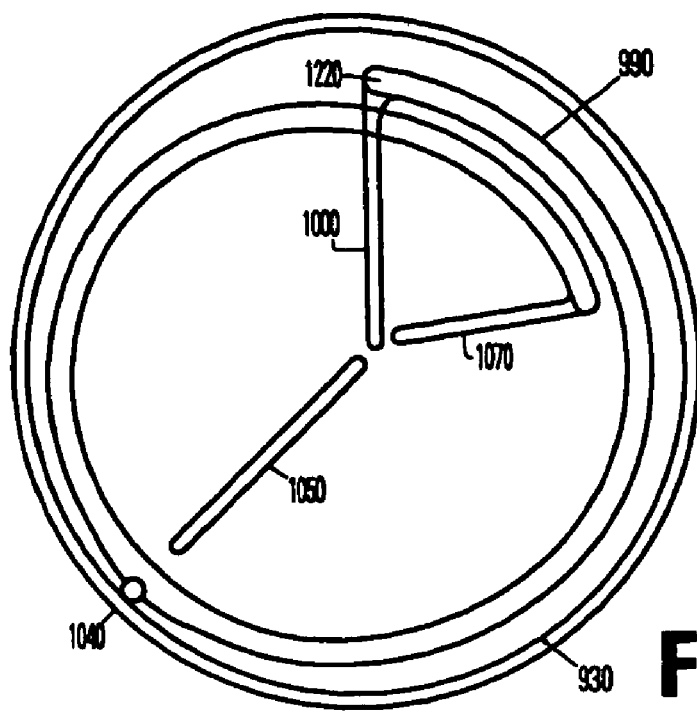
FIG. 49 depicts a tenth separation channel design, in accordance with an embodiment of the present invention.

FIG. 49 shows a CFC disk 930 with another separation channel design where the separation channel 990 extends beyond 360° to 420°. The reasons for extending the channel are to provide greater separation path length for red cell packing or concentration, achieving a higher hematocrit packed red cell product 1010, or a greater separation path length for waste product 1030 (and a smaller radius) to obtain better waste product removal with cellular contamination.

Optical Sensor Control of the Red Cell-Plasma Interface

Figure 50:
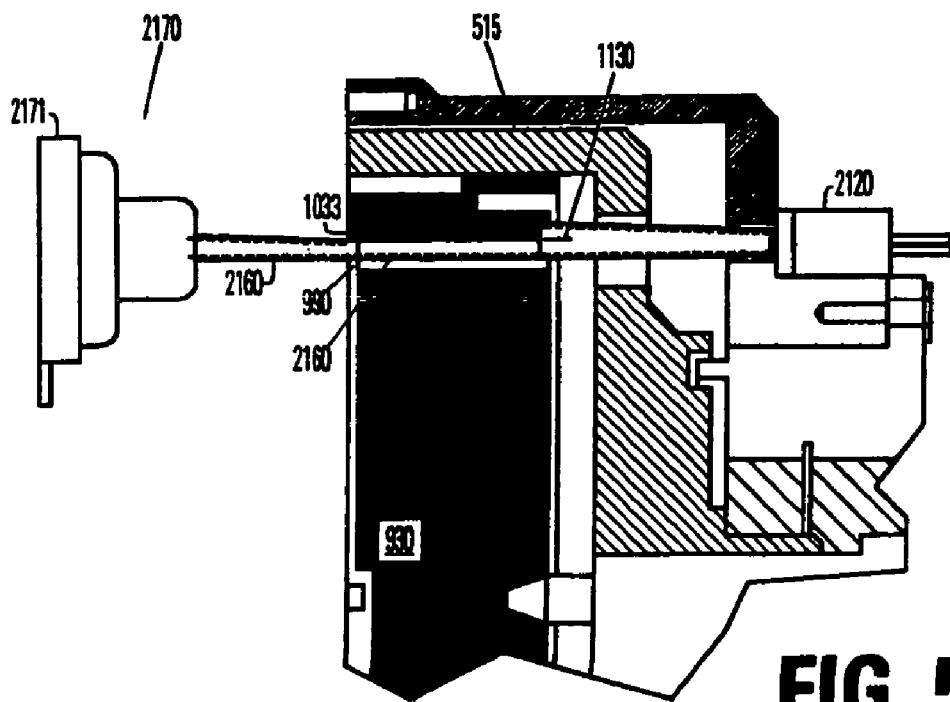
FIG. 50 is a cutaway view of a light detector for use in determining the RBC/plasma interface in a continuous flow centrifuge, in accordance with an embodiment of the present invention.

FIG. 50 shows the design concept used to detect and measure the location of the waste product-red cell interface within the separation channel of a rotating centrifuge disk 930 using a sensor 2170 incorporating an optical detector 2171. A light source 2120 is turned on for a very short time (an arc of about one degree) each rotation of the CFC disk 930 to illuminate a short angular segment or region of the separation channel 990 across all or part of the radial width of this channel. FIG. 50 shows a location of this optical sensing region. The red cell layer 1033 blocks the passage of light but the waste product layer 2160 transmits this light to an optical detector 2171. The optical detector 2171 receives an amount of light proportional to the radial width of the waste product 2160 in the separation channel 990 determined by the location of the red cell-waste product interface 1130. The analog detector output increases when this interface moves radially outward and decreases when it moves radially inward. This detection of the interface location is used during continuous-flow operation in a feedback loop to control the pump flow rates in the system. In operation a desired reference interface location is established for a particular process (for example, maintaining the interface at a particular position relative to the point of a knife edge diverter) and the actual location of the interface 1130 is measured by the described optical means. The error signal of actual minus reference location (which are the optical analog values) is used to change flow rate ratios in proportion to the error signal with appropriate time constants or averaging. This system and method can thus maintain the red cell-waste product interface 1130 in its desired location. Another optical detector 2171 can be placed to provide information about the conditions just outside the waste product removal port 1090.

As noted above, the CFC and cassette components may be made of clear plastic to allow for the use of optical detectors. To prevent scattering, it may be advantageous to place an opaque barrier on the disk and/or cap in the region of interest. The opaque barrier includes a hole so as to more precisely direct the light beam from the light source 2120.

An optical detector 2171 may also look at one or more additional regions in the separation channel 990. One additional region may be identical to the first measurement region but is modified to provide an accurate radial distance calibration. An additional opaque barrier may be added over the red cell portion of the separation channel in this region. This barrier extends into the waste product portion of the channel to provide only a waste product radial distance seen by the optical sensor. This fixed distance and the optical output represent a fixed hematocrit. This can be used to calibrate the optical sensor output in the measurement region. Such a calibration will compensate for changes in waste product transmissibility, light source intensity, light scattering, and light absorption through CFC disk surfaces.

EXAMPLES

The current invention is able to use one console or electromechanical instrument to perform multiple blood treatment processes. Each process requires a different disposable set or product specifically designed to implement that process in combination with specific software for each processes.

For all processes shown schematically in FIGS. 51-60 the disposable set described above is removed from a sterile package and hung on the pins of the console. Solution bags or bottles are either attached by the operator using the Luer-lock, spike or other attachments means. The bags or bottles could also be pre-attached. Bacterial filters (e.g., 0.2 micron) may be placed in the flow paths from these bags to ensure the maintenance of sterility. The bags are hung in designated locations on the console.

The console "calibration" button is depressed and calibrations and system software status are checked. Data collection may be performed manually by the operator using a bar code wand reader (not shown) and automatically via the bar code reader console.

Various ways of implementing the processes contemplated by the instant invention are illustratively depicted in the schematic diagrams of FIGS. 51-60. It will be understood that these Figures are intended as non-limiting examples of processes and that a feature of the invention is that other processes can be performed by selecting and implementing a different series of operations and states.

Example 1

Automatic Glycerolization of Standard Unit of Packed RBCs in Storage Solution

Red cells are collected from a donor in a standard bag with a standard anticoagulant. They are concentrated by standard methods to a hematocrit of about 90% and storage solution is added. This bag of a standard packed RBC blood component is then attached with a sterile docking device to the sterile disposable set, using a cassette configured for a glycerolization process that interacts with the control module. Glycerol solution is in a bottle attached to the disposable set using a standard spike; although it will be readily apparent to one of skill in the art that solutions other than glycerol may be used in accordance with this embodiment of the present invention. Sterility is achieved by using a bacterial filter for glycerol added to the RBCs. Glycerol solution is slowly added based on RBC volume. Then, the RBCs are concentrated, by removing fluid, to a hematocrit of about 75% to 80%. Glycerolized RBCs are stored in the glycerolized RBC freezing bag. They can now be frozen and stored in a −80° C. freezer.

Figure 51:
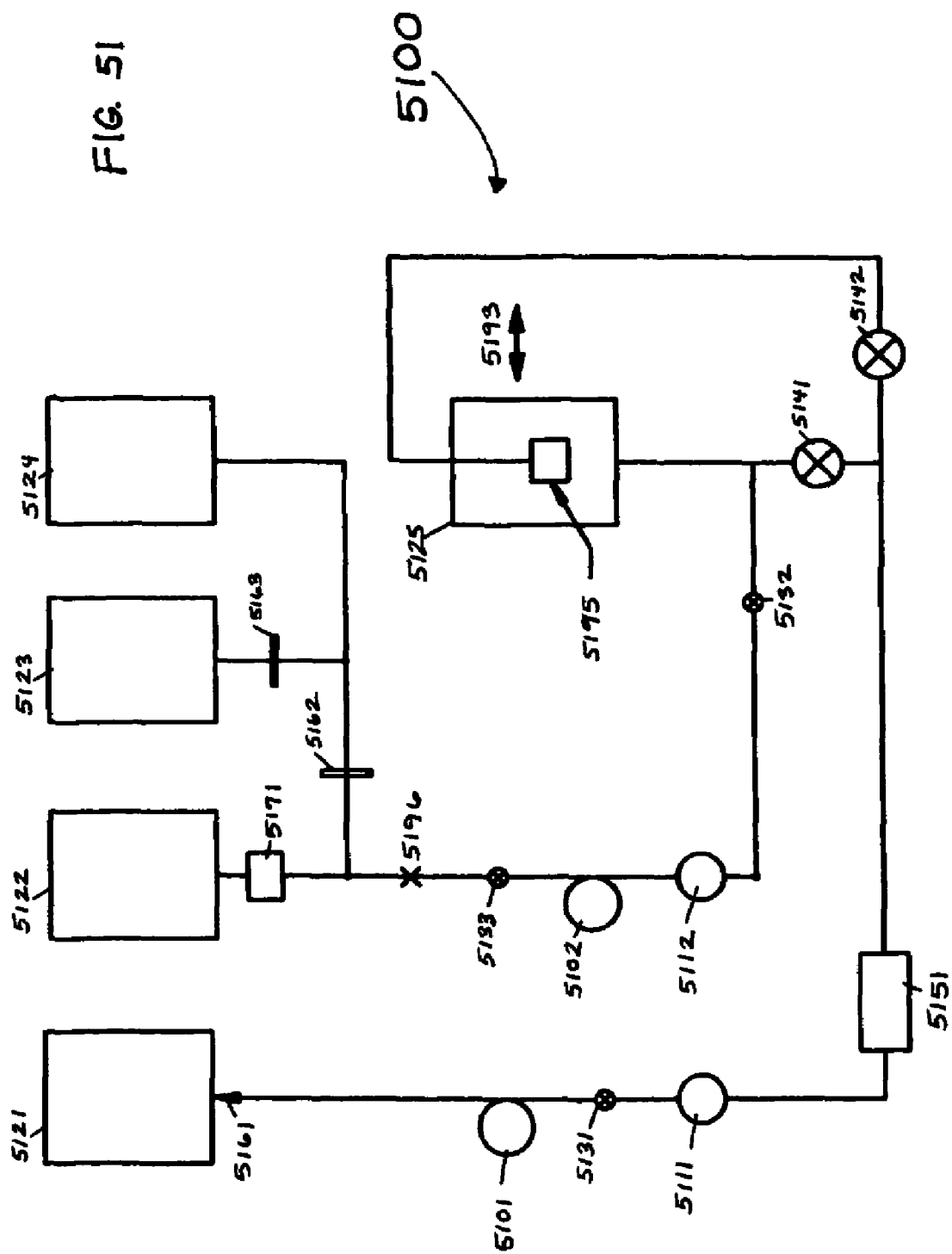
FIG. 51 is a schematic of a system to implement a glycerolization process, in accordance with an embodiment of the present invention.
Figure 52:
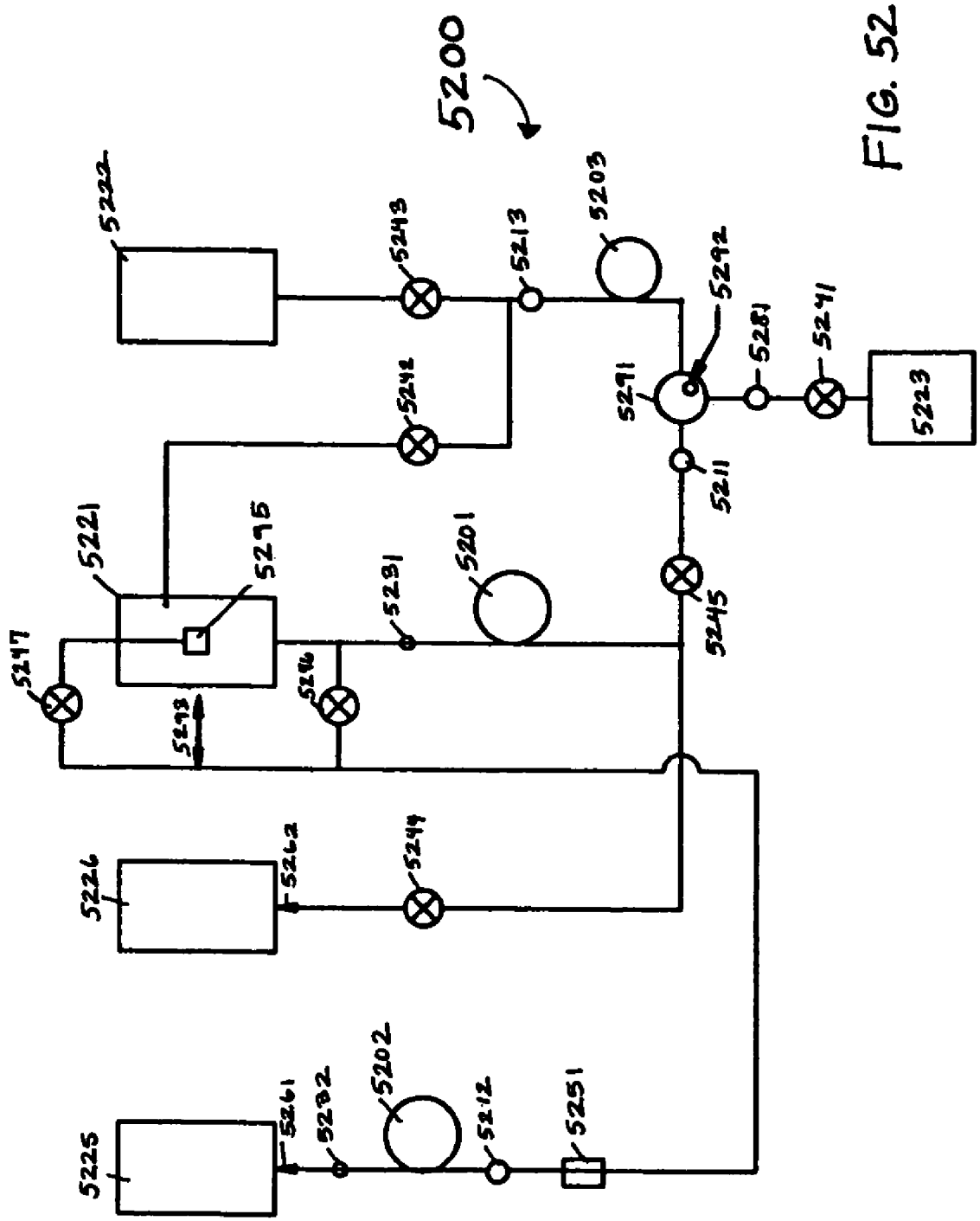
FIG. 52 is a schematic of a system to implement a glycerolization process, in accordance with an embodiment of the present invention.

More specifically, as illustratively depicted in FIGS. 51 and 52, the present invention may be configured as a system 5100 to implement a glycerolization process. With reference to FIG. 51, such a system 5100 may include a recirculation bag 5125 connected to a bag of packed RBCs in storage solution 5122 and a glycerol (e.g., 57% glycerol) bottle 5121. The bag of packed RBCs 5122 is connected to the system 5100 via a sterile dock 5171, and the glycerol bottle 5121 is connected by a standard spike 5161. A bacterial filter 5151 is additionally included to maintain sterility of the system 5100. The recirculation bag 5125 further includes a spray nozzle 5195 that provides a conical spray of glycerol solution into the contents of the recirculation bag 5125. A mixer or shaker apparatus 5193 is also included, to continually mix the contents of the recirculation bag 5125. A satellite bag 5123 and frozen red cell product bag 5124 are additionally included in the system 5100. Fluid communication between the satellite bag 5123 and frozen red cell product bag 5124 and the remainder of the glycerolization system 5100 is controlled by manual clamps 5162, 5163.

A glycerol pump 5101 and blood pump 5102 are included to pump the various fluids through the system 5100. Pressure measurement devices 5111, 5112 are included to monitor the flow of the various fluids through the tubing, and ultrasonic air sensors 5131, 5132 are further included to monitor the flow of air through the tubing (e.g., to determine when the fluid contents of a particular bag have been evacuated). A microprocessor or other, similar electronic device (not shown) collects the information from the pressure measurement devices 5111, 5112 and ultrasonic air sensors 5131, 5132 and controls the valves 5141, 5142 and pumps 5101, 5102 accordingly, to implement the glycerolization process of this embodiment of the present invention. Additionally, the bags and various other components of the system are connected to one another by tubing in communication with a cassette (not shown) designed specifically for the operation of this embodiment of the present invention, as discussed in greater detail above.

To implement the process of this embodiment of the present invention, a glycerolization solution may be added to RBCs by controlling the flow rate, dispersion and mixing of glycerolizing solution into the RBC volume. An RBC bag 5122 is sterilely docked to the disposable set. The RBCs are transferred (pumped) from their product bag 5122 to a recirculation bag 5125 that is part of the set. The RBCs are pumped at a constant flow rate until the product bag 5122 is empty. Then, the time and volume of RBCs transferred are known. The total volume of glycerolizing solution is a fixed ratio to this transferred red cell volume. The pump 5101 that pumps the glycerolizing solution is controlled to achieve this volume. The pump flow rates and times and the step by step sequence of operations are controlled by the microprocessor and software specific to this process.

Dispersion of glycerolizing solution into the RBC volume in the recirculation bag 5125 is achieved by a conical spray of solution produced within this RBC volume. This spray distributes droplets of solution into the red cell volume, achieving dispersion and some mixing and reducing localized high concentrations of glycerolizing solution in this RBC volume. High concentrations and poor mixing may result in RBC damage. A spray nozzle 5195 at the end of a tube inside the recirculation bag 5125 achieves this conical spray. The bag 5125 contents are also continuously mixed using a bag shaker 5193.

The glycerolized RBCs are then transferred to another bag 5124 that is suitable for placement in a standard blood bank centrifuge bucket. The RBCs and glycerolizing solution are separated and a percentage of glycerolizing solution is removed. This is performed to achieve about 60% to about 80% hematocrit red cells, to reduce the total volume of glycerol and RBC bag volume, and aid in the removal of glycerol in a subsequent deglycerolization (wash) procedure after the frozen RBCs have been thawed. A large volume of glycerol is needed in the glycerolization process because of dilution by the plasma and storage solution mixed with the RBCs.

As illustratively depicted in FIG. 52, the system 5200 of the present invention may be configured for a concentration operation to concentrate RBCs for freezing (e.g., as part of a glycerolization process). This configuration of the system 5200 includes a recirculation bag 5221 connected to a bag of packed RBCs in storage solution 5226 and a glycerol bottle 5225. The bag of packed RBCs 5226 and glycerol bottle 5225 are connected to the system 5200 with standard spikes 5261, 5262. A bacterial filter 5251 is also included to maintain sterility of the system 5200. The recirculation bag 5221 further includes a spray nozzle 5295 that provides a conical spray of glycerol solution into the contents of the recirculation bag 5221. A mixer or shaker apparatus 5293 may also be included, to continually mix the contents of the recirculation bag 5221. A glycerolized RBC bag 5222 and waste product bag 5223 are additionally included in the system 5200. A free plasma hemoglobin sensor 5281 is included, as well.

A CFC 5291 is included, as described in greater detail above. In this concentration embodiment of the present invention, the CFC 5291 separates glycerolized RBCs from a waste product (e.g., glycerolizing solution, some plasma and RBC storage solution); thereby concentrating the RBCs. An optical detector 5292 is included with the CFC 5291 to monitor the operation of the CFC 5291, as described above.

A glycerol pump 5202, recirculation pump 5201 and RBC pump 5203 are included to pump the various fluids through the system 5200. Pressure measurement devices 5211, 5212, 5213 are included to monitor the flow of the various fluids through the tubing, and ultrasonic air sensors 5231, 5232 are further included to monitor the flow of air through the tubing (e.g., to determine when the fluid contents of a particular bag have been evacuated). A microprocessor or other, similar electronic device (not shown) collects the information from the pressure measurement devices 5211, 5212, 5213, ultrasonic air sensors 5231, 5232, free plasma hemoglobin sensor 5281 and optical detector 5292, and controls the valves 5241-5247, pumps 5201, 5202, 5203 and CFC 5291, accordingly, to implement the concentration process. Additionally, the bags and various other components of the system are connected to one another by tubing in communication with a cassette (not shown) designed specifically for the operation of this embodiment of the present invention, as discussed in greater detail above.

The glycerolized RBCs are concentrated (a volume of glycerolizing solution plus some plasma and RBC storage solution are removed) using the CFC disk 5291. This is a recirculation process in which RBCs are removed from the recirculation bag 5221, fluid is separated and discarded, and the RBCs (at a higher hematocrit) are returned to the recirculation bag 5221 (while the bag 5221 is being shaken and its contents mixed). This occurs until a specific hematocrit is achieved in the recirculation bag 5221. The hematocrit is known by the ratio of outlet RBC pump flow rate and inlet blood flow rate. An optical detector 5292 is used to maintain a fixed location in the CFC separation channel by varying the RBC pump flow rate in a feedback loop with the optical detector 5292 providing a signal proportional to the red cell-plasma (i.e., waste product) interface location.

The glycerolized RBCs are then pumped out of the recirculation bag 5221 and into a bag suitable for freezing 5222.

Example 2

Automatic Deglycerolization of RBCs

The system of the present invention may be used to automatically deglycerolize (i.e., RBC washing and removal of glycerol and free plasma hemoglobin) a unit of glycerolized, frozen and then thawed RBCs; although it will be readily apparent to one of skill in the art that solutions other than glycerol may be removed in accordance with this embodiment of the present invention. The overall approach for deglycerolization is to mix the glycerolized RBCs first with a hypertonic solution that shrinks the RBCs and expels some of the glycerol from the RBCs. Then, the RBCs are washed in an isotonic solution to remove glycerol and free plasma hemoglobin from the fluid surrounding the RBCs. During this wash process, glycerol diffuses out of the cells and the RBCs return to normal volume.

Figure 53:
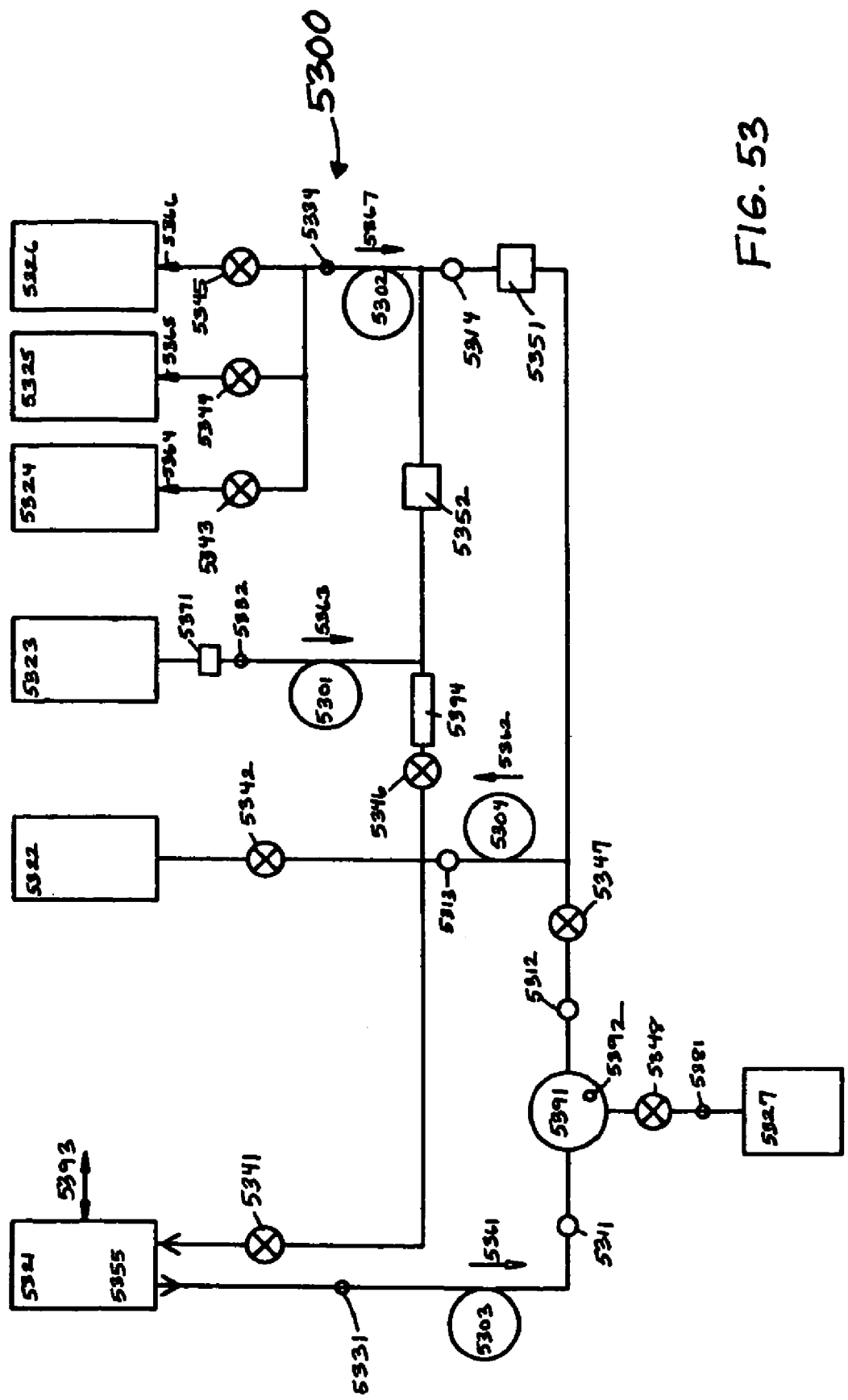
FIG. 53 is a schematic of a system to implement a deglycerolization process, in accordance with an embodiment of the present invention.

As illustratively depicted in FIG. 53, the present invention may be configured as a system 5300 to perform an automatic deglycerolization process. In this configuration, the system 5300 includes a recirculation bag 5321 with a blood filter 5355, connected to a set of three solution bags 5324, 5325, 5326 (e.g., for containing (1) a hypertonic solution, (2) an isotonic wash solution and (3) a red cell additive or storage solution, respectively) and a bag of thawed, glycerolized RBCs 5323. The bag of thawed RBCs 5323 is connected to the system 5300 via a sterile dock 5371, and the three solution bags 5324, 5325, 5326 are connected with standard spikes 5364, 5365, 5366. Bacterial filters 5351, 5352 are additionally included to maintain sterility of the system 5300, and a static mixer 5394 is included to assist in mixing the RBCs with the various solutions contained in the solution bags 5324, 5325, 5326. A mixer or shaker apparatus 5393 may also be included, to continually mix the contents of the recirculation bag 5321. A deglycerolized RBC bag 5322 and waste product bag 5327 are additionally included in the system. A free plasma hemoglobin sensor 5381 is included, as well.

A CFC 5391 is included, as described in greater detail above. In this concentration embodiment of the present invention, the CFC 5391 separates RBCs from a waste product (e.g., glycerolizing solution, some plasma, RBC storage solution and solutions from solution bags). An optical detector 5392 is included with the CFC 5391 to monitor the operation of the CFC 5391, as described above.

A thawed RBC pump 5301, solution pump 5302, blood pump 5303 and RBC pump 5304 are included to pump the various fluids through the system 5300. Pressure measurement devices 5311, 5312, 5313, 5314 are included to monitor the flow of the various fluids through the tubing, and ultrasonic air sensors 5331, 5332, 5333, 5334 are further included to monitor the flow of air through the tubing (e.g., to determine when the fluid contents of a particular bag have been evacuated). A microprocessor or other, similar electronic device (not shown) collects the information from the pressure measurement devices 5311, 5312, 5313, 5314, ultrasonic air sensors 5331, 5332, 5333, 5334, free plasma hemoglobin sensor 5381 and optical detector 5392, and controls the valves 5341-5348, pumps 5301, 5302, 5303, 5304 and CFC 5391, accordingly, to implement the deglycerolization process. Additionally, the bags and various other components of the system are connected to one another by tubing in communication with a cassette (not shown) designed specifically for the operation of this embodiment of the present invention, as discussed in greater detail above.

In operation, a frozen glycerolized RBC bag 5323 is thawed in a standard fashion. A deglycerolization cassette (not shown) is inserted into the control module. The disposable set bags are hung. The solutions are hung and spiked. The thawed glycerolized RBC bag 5323 is hung and attached with a sterile docking device 5371 to a disposable set. The recirculation bag 5321 is mounted on the bag shaker 5393. The START button is depressed and the display indicates "Prime System," and the process timer in the display indicates time from start.

The solution pump 5302 is used to add the solutions at the required flow rates and with the required equilibration times to the recirculation bag 5321. Solenoid operated finger-type pinch valves 5341-5348 are used to pinch closed or open the tubing selectively to turn fluid flows on or off. These pinch valves 5341-5348 are computer-controlled, and are generally of the type that have been used successfully and reliably on conventional autotransfusion, apheresis and hemodialysis systems. Hall effect sensors (not shown) independently confirm the proper opening and closing of these valves 5341-5348. Pinch valves 5341-5348 are opened or closed to select the appropriate solution for the initial dilutions, and the solution pump 5302 adds these solutions to the recirculation bag 5321 after the RBCs have been pumped into this bag 5321 from the glycerolized RBC bag 5323. All saline and storage solutions pass through a bacterial filter 5351, 5352 to ensure sterility.

In the subsequent deglycerolization process, the solution pump 5302 adds saline to blood as it exits the CFC 5391 using the RBC pump 5304 during blood recirculation. The solution pump 5302 also is used to prime the system 5300 with saline (i.e., fill all blood lines with saline and eliminate air) during a pre-dilution stabilization period. The solution pump 5302 is used to add storage solution at the end of deglycerolization and to purge blood out of the CFC 5391 and lines by pumping solution through these devices and pushing blood ahead of the solution into the deglycerolized RBC bag 5322.

The blood pump 5303 is used to pump blood out of the recirculation bag 5321 and into either the recirculation bag 5321 or the deglycerolized RBC bag 5322. Blood pump timing and flow rates are computer-controlled. A blood particulate filter sac 5355 in the recirculation bag 5321 is used to eliminate particulates, clots and white cell agglomerates that form during the deglycerolization process. The blood pump 5303, solution pump 5302, RBC pump 5304 and thawed RBC pump 5301 flow rates are controlled to achieve rapid, optimal deglycerolization by recirculation of blood through the CFC 5391 with waste removal, followed by wash solution (e.g., 0.9% saline, 0.2% glucose) addition.

Pressure measurements are made by pressure transducers 5311, 5312, 5313, 5314 in the control module. Diaphragm pressure isolators are used to obtain an impervious barrier and ensure sterility. The pressure measurements are made for the following reasons: to control the limits of CFC 5391 operation (e.g., measuring inlet pressure); to ensure proper, safe system operation within acceptable pressure ranges; and to inform the user when bags are full or empty (i.e., by pressure increases or decreases). Ultrasonic sensors 5331, 5332, 5333, 5334 are used to detect air; indicating when bags are empty and to determine and terminate pump flow when the glycerolized RBC bag 5323, solution bags 5324, 5325, 5326 or recirculation bag 5321 are empty.

The pressure measurements, the mode selection (i.e., glycerolization or deglycerolization) by the user, and the control logic for that mode provide inputs to the computer (i.e., microprocessor) controller. The outputs controlled by the computer include the timing (i.e., on/off) and speeds (i.e., fluid flow rates) of the pumps 5301, 5302, 5303, 5304 and the timing (i.e., on/off) of the tubing pinch valves 5341-5348.

More specifically, as illustratively depicted in FIG. 53, a deglycerolization process may be performed with the system 5300 of the present invention with three solutions: a hypertonic solution in a first solution bag 5324 (e.g., 12% NaCl); an isotonic wash solution in a second solution bag 5325 (e.g., 0.9% NaCl, 0.2% glucose); and a red cell additive or storage solution in a third solution bag 5326 (e.g., AS3 NUTRICEL® Additive Solution; available from Gambro BCT, Inc., Lakewood, Colo.). An objective of this process and system is sterile deglycerolization and long-term refrigerated storage (e.g., at least two weeks) of the deglycerolized red cell product. The storage solution is selected to achieve this two-week (or longer) refrigerated storage after deglycerolization.

The hypertonic solution is pumped by the solution pumps 5302 and the thawed glycerolized RBCs are simultaneously pumped by the thawed RBC pump 5301 through a static mixer 5394 and into a recirculation bag 5321, which is shaken to achieve good mixing. The flow rate ratio of the solution to the RBCs is fixed at an optimal value for minimal hemolysis. This process step ends when the thawed deglycerolized RBC bag 5323 is empty and all RBCs are in the recirculation bag 5321. Ultrasonic air detector 5332 detects when the thawed deglycerolized RBC bag 5323 is empty. Thus, the volume of hypertonic solution is dependent upon the volume of thawed RBCs and is maintained at a ratio that minimizes hemolysis and maximizes RBC recovery.

An equilibration interval of about 2 to 5 minutes then occurs in which the recirculation bag 5321 is shaken and its contents mixed. The RBCs begin to shrink in this process step, expelling glycerol. Shrinking the RBCs to a near optimal size, at a near optimal rate may minimize hemolysis. The RBC size may reduced sufficiently in this process step, so that, in subsequent steps (e.g., the isotonic saline wash) the RBCs do not rupture, causing excessive hemolysis occurs.

The next process step is to introduce additional hypertonic solution from solution bag 5324 at a rate and a volume that is optimal for minimal hemolysis. Since the total volume of thawed RBCs is known from the flow rate and duration of pumping with the thawed RBC pump 5301 into the recirculation bag 5321, the desired fixed volume ratio of hypertonic solution to RBCs can be calculated and the solution pump 5302 controlled to achieve this volume. This hypertonic solution volume is added while the bag shaker 5393 is shaking and mixing the recirculation bag 5321 contents.

The next process step is to pump blood from the recirculation bag 5321 (using the blood pump 5303) into the CFC 5391, and pump cells out of the CFC 5391 (using the RBC pump 5304) back to the recirculation bag 5321. Waste fluid is expelled from the CFC 5391 to the waste bag 5327. Isotonic solution (i.e., wash solution) is pumped by the solution pump 5302 out of the isotonic solution bag 5325 into the RBC flow stream after the RBC pump 5304. The blood pump flow rate is more or less fixed at an optimum of about 200 to 300 mL/min. The RBC pump 5304 is controlled by the optical detector 5392 to maintain a fixed red cell-plasma interface location within the CFC 5391 disk separation channel. The ratio of RBC pump flow to blood pump flow is proportional to entering blood flow hematocrit and to CFC 5391 disk rotational speed. The latter is kept constant. The hematocrit in the recirculation bag 5321 is kept constant by changing the flow rate of isotonic solution into the RBC stream, using the hematocrit value calculated from blood 5303 and RBC pump 5304 flow rates in this feedback control loop. Another method of hematocrit control may also be used: two pressure sensors at either end of a laminar flow element (shown, e.g., in FIG. 59 as elements 5911, 5912 and 5997) may be used along with a temperature sensor (not shown) in the blood line entering the CFC 5391 disk to measure blood pressure drop, which correlates directly with viscosity and hematocrit.

The recirculation process removes fluid (i.e., waste product) from the blood and replaces it with isotonic solution in a continuous concentration and dilution process. The optimal hematocrit values for a rapid, efficient wash are about 45% entering the CFC 5391 disk to about 65% leaving the disk. This wash process step time is about 15 minutes, with 1750 to 2000 mL of isotonic solution consumed. A short wash and overall process time may be desirable to maximize the number of units of frozen RBCs that can be washed per hour for use in emergencies and to minimize overall time and costs. This wash process step ends when the fixed volume of isotonic solution is consumed.

The next process step is an additional wash with the same parameters, but using the red cell storage solution from the corresponding bag 5326. This process step continues until about 150 to 250 mL of the red cell storage solution is consumed. Then the recirculation bag 5321 is emptied via the blood 5303 and RBC 5304 pumps through the CFC 5391 disk and into the deglycerolized RBC bag 5322. The CFC 5391 disk removes additional waste fluid.

The last process step is to purge the recirculation bag 5321 and CFC 5391 by pumping additional red cell storage solution into the recirculation bag 5321, into the CFC 5391 and into the deglycerolized RBC bag 5322. The CFC 5391 remains filled with the red cell storage solution at the end of the process (about 40 to 60 mL of volume). The hematocrit in the deglycerolized RBC bag is about 50% to 60%.

Figure 54:
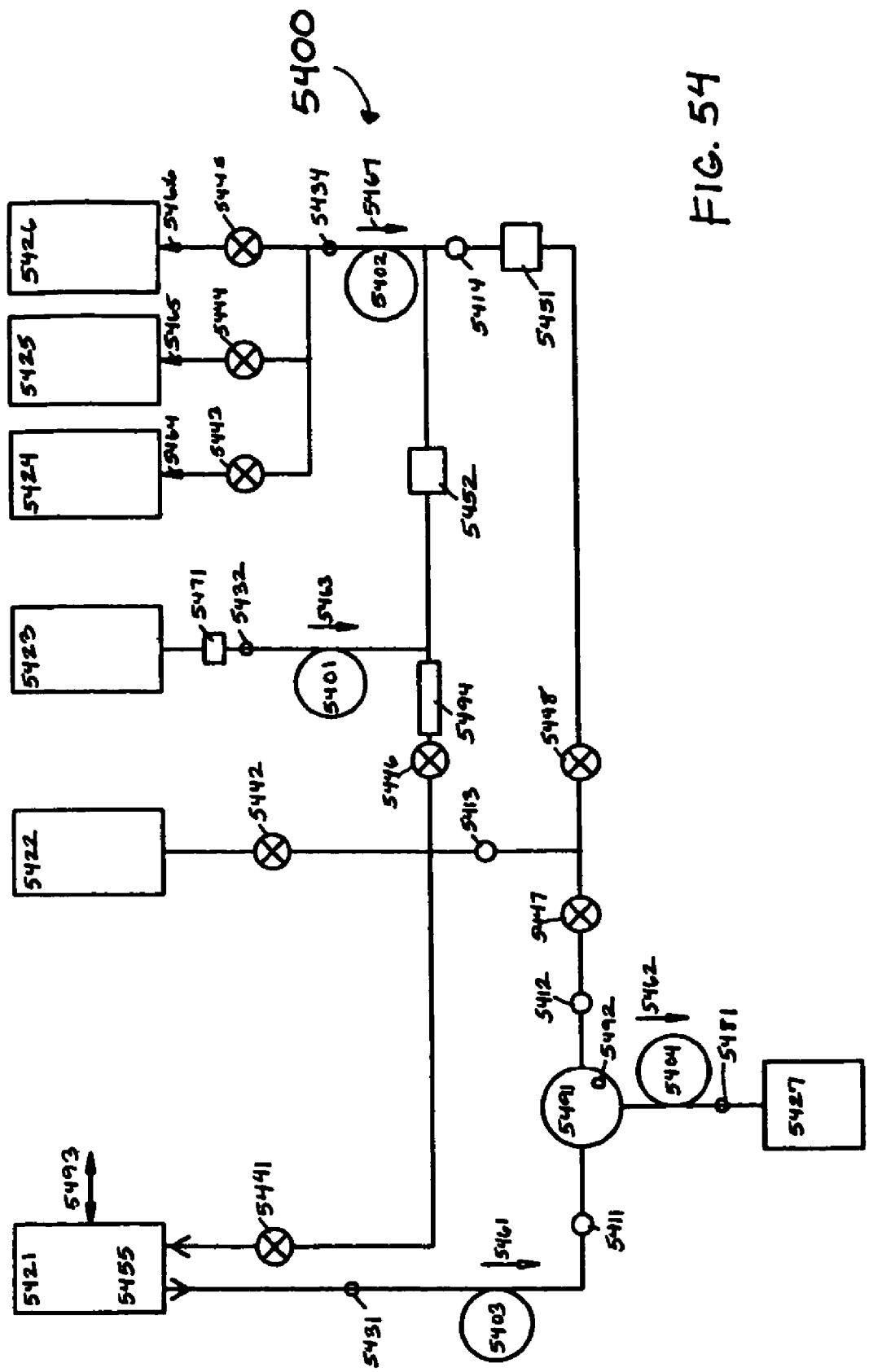
FIG. 54 is a schematic of a system to implement a deglycerolization process, in accordance with an embodiment of the present invention.

The only difference between the processes illustratively depicted in FIGS. 53 and 54 is that the process depicted in FIG. 54 does not use an RBC pump, but instead uses a plasma pump 5404. The flow rate of RBCs out of the CFC 5491 is then determined by the difference between the CFC 5491 inlet blood flow and the CFC 5491 outlet plasma flow. The RBC flow rate is therefore calculated and used in the same manner as the pumped RBC flow rate to control the red cell-plasma interface within the CFC 5491 disk and to calculate CFC inlet (and recirculation bag 5421) hematocrit.

Figure 55:
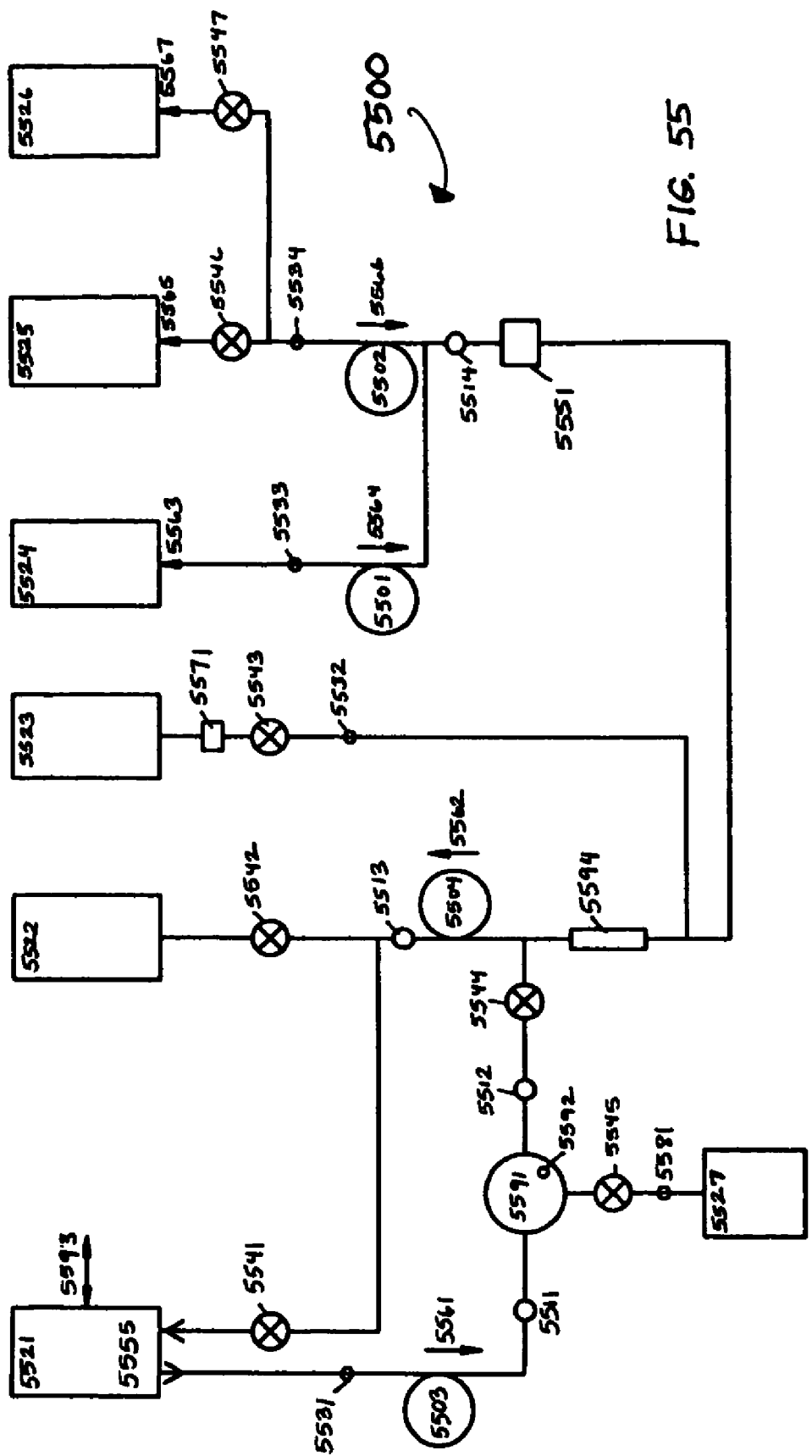
FIG. 55 is a schematic of a system to implement a deglycerolization process, in accordance with an embodiment of the present invention.

The process illustratively depicted in FIG. 55 is also similar in many respects to those depicted in FIGS. 53 and 54. The process of FIG. 55 differs in that it performs the mixing of two solutions to replace a single isotonic (e.g., 12% NaCl) solution. This permits the osmolality (e.g., % saline) to be varied during the first two process steps; the addition of a hypertonic solution to RBCs as they are transferred from the thawed glycerolized RBC bag 5523 to the recirculation bag 5521; and the addition of a hypertonic solution to RBCs in the recirculation bag 5521. Thus, the hypertonicity can be varied during these two process steps to achieve optimal values and results. This may be accomplished by using the solution pumps 5501, 5502 to vary the ratio of, for example, the hypertonic solution and isotonic solutions. This can achieve a slow, controlled reduction in wash solution hypertonicity in order to maintain shrunken RBCs during the wash process or achieve a slow rate of size increase. Maintaining the RBCs in a substantially smaller, shrunken state during the wash may achieve several benefits: the glycerol within the RBC is more effectively removed by keeping a substantial osmotic gradient on the RBC and minimizing cell volume; the surface area to volume ratio of the cell is increased to improve diffusion rate of glycerol out of the cell and wash solution into it; and a reduced RBC volume during the wash decreases hemolysis by preventing membrane damage to some fraction of RBCs that swell excessively during an isotonic solution wash. To accomplish this, the configuration of the system in FIG. 55 includes two solution pumps 5501, 5502, rather than one solution pump and one thawed RBC pump, as described with respect to the embodiments of the present invention depicted in FIGS. 53 and 54. The other steps of the process illustratively depicted in FIG. 55 are substantially identical to those depicted in FIGS. 53 and 54.

Figure 56:
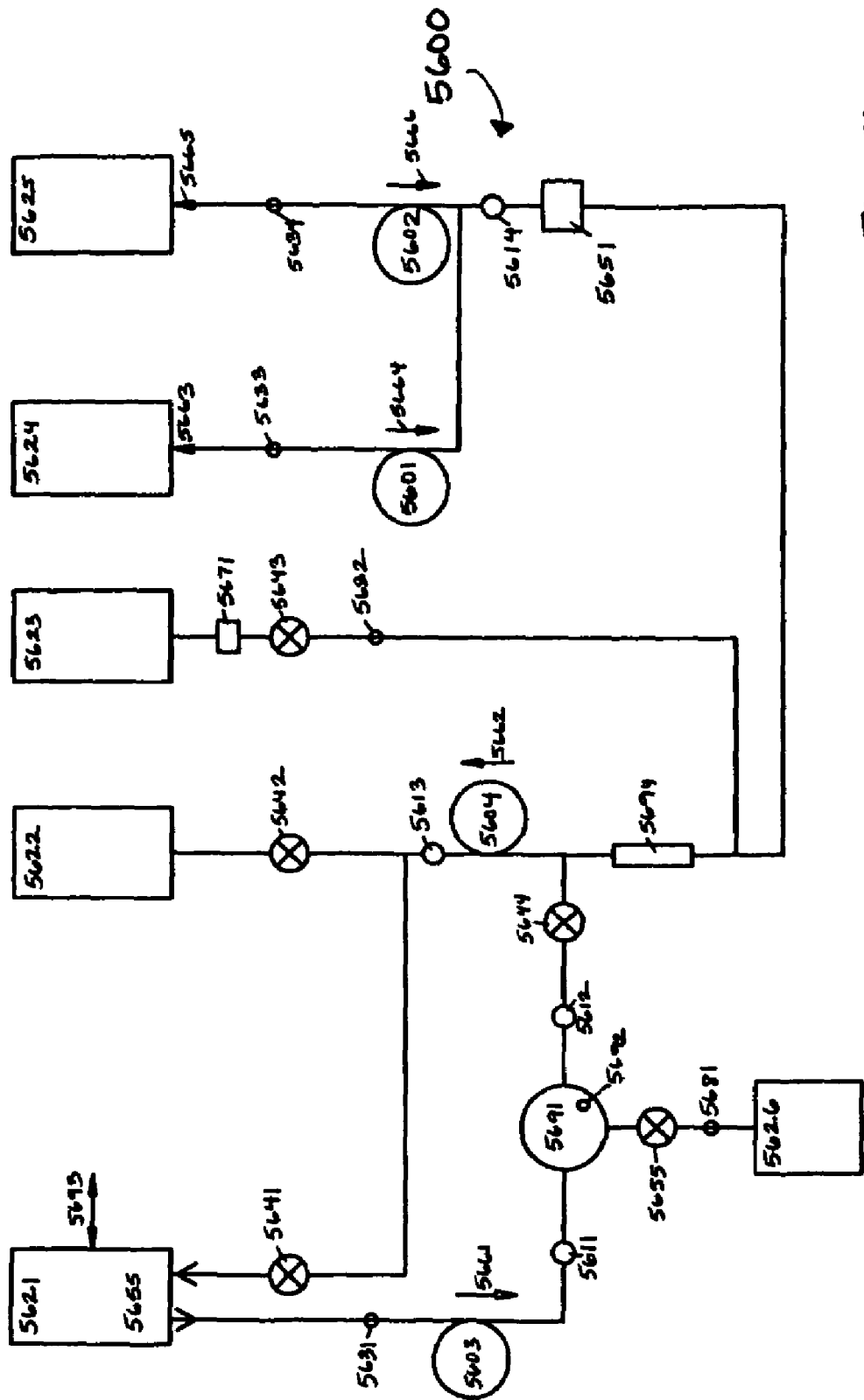
FIG. 56 is a schematic of a system to implement a deglycerolization process, in accordance with an embodiment of the present invention.
Figure 57:
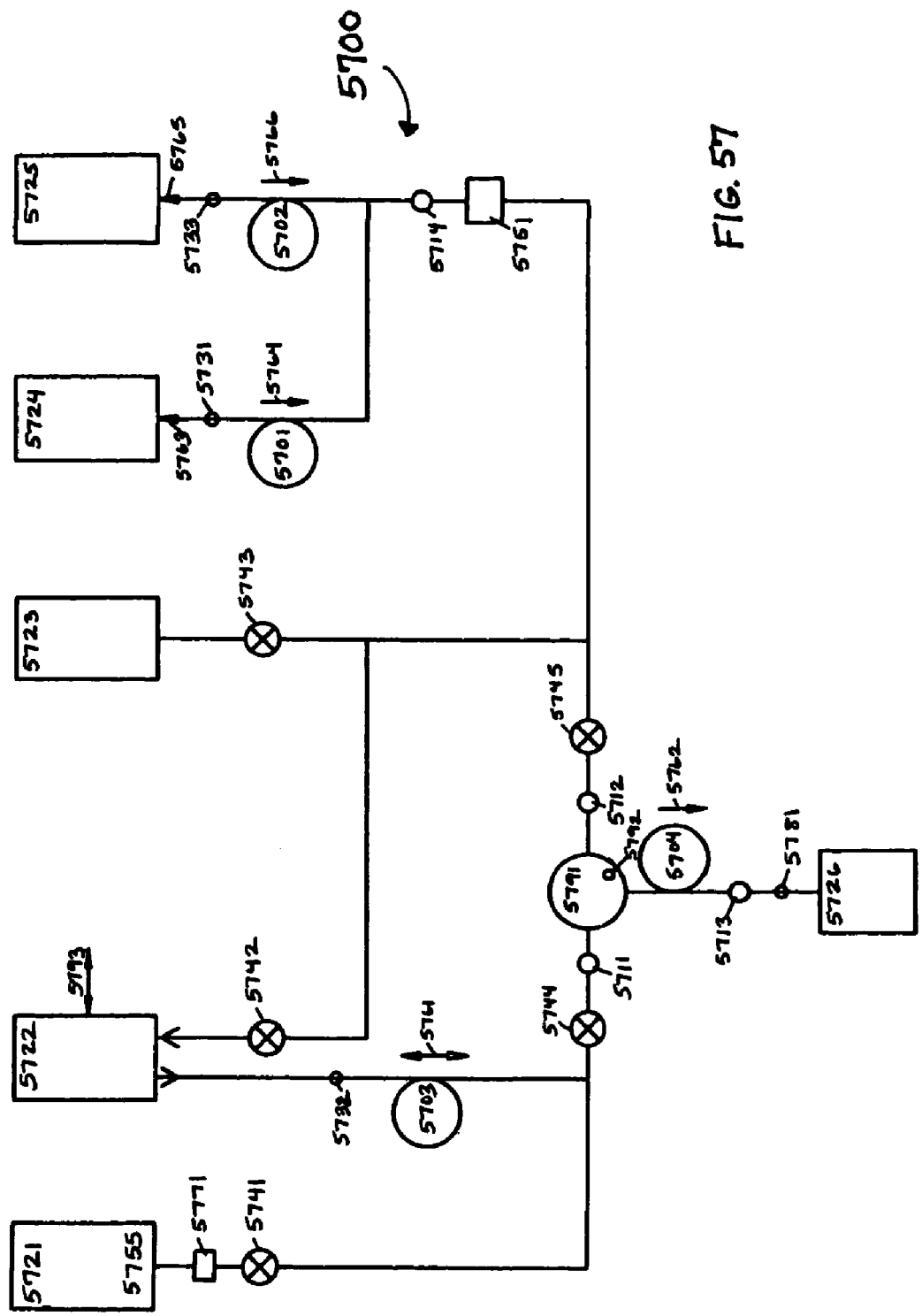
FIG. 57 is a schematic of a system to implement a deglycerolization process, in accordance with an embodiment of the present invention.
Figure 58:
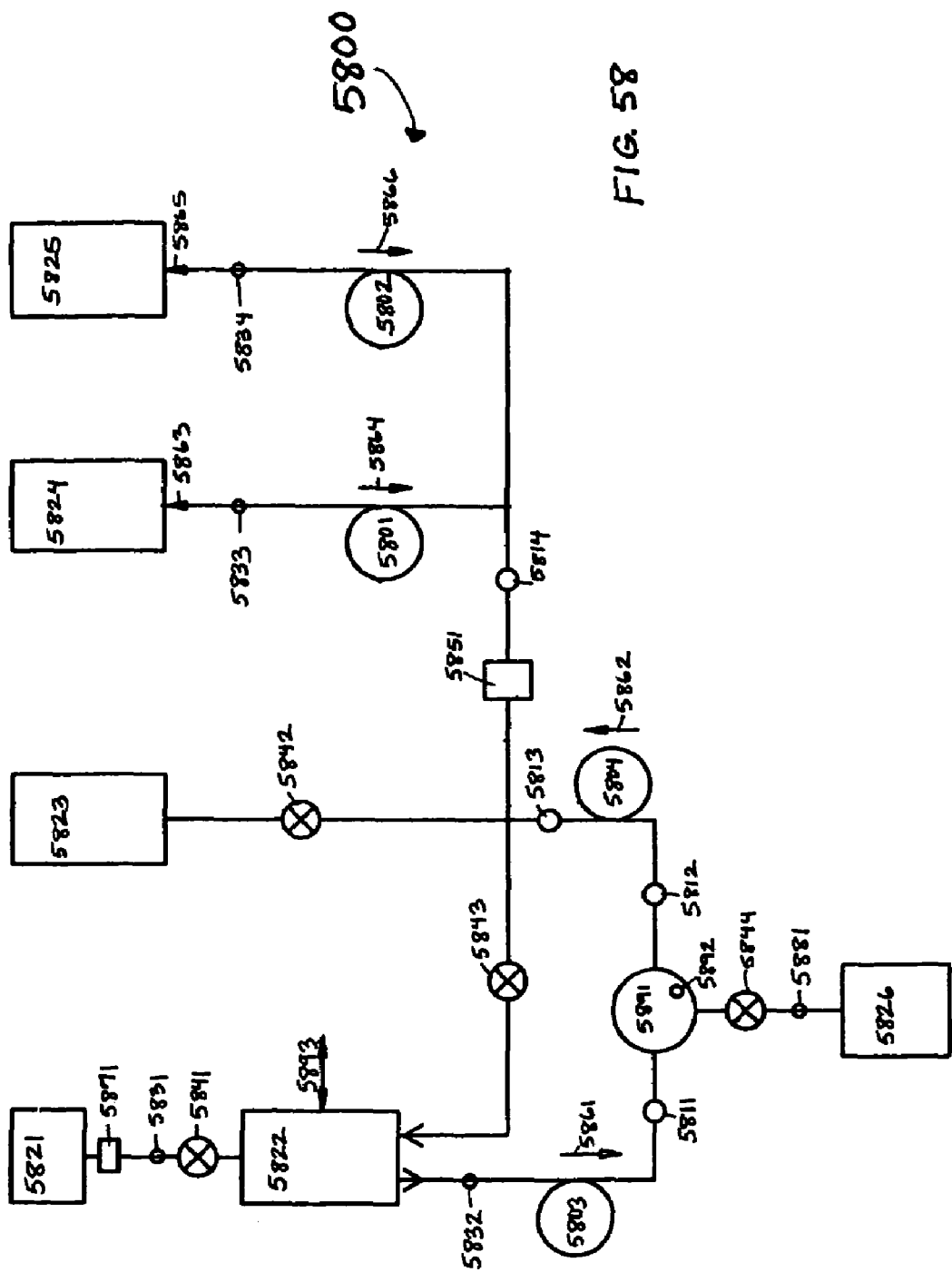
FIG. 58 is a schematic of a system to implement a deglycerolization process, in accordance with an embodiment of the present invention.

The process illustratively depicted in FIGS. 56-58 is also similar in many respects to those depicted in FIGS. 53 and 54. One difference is that only two solutions are used in these embodiments, and each solution flow rate and volume is controlled by its own pump.

The process illustratively depicted in FIG. 56 is almost identical to that depicted in FIG. 53, except for the use of two independently pumped solutions contained in solution bags 5624, 5625. The RBC pump 5604 transfers RBCs from the thawed deglycerolized RBC bag 5623 to the recirculation bag 5621; there is no separate thawed RBC pump.

The process illustratively depicted in FIG. 57 is almost identical to that depicted in FIG. 54, except for the use of two independently pumped solutions contained in solution bags 5724, 5725. Another difference is the pumping of the thawed glycerolized RBCs into the recirculation bag 5721 using the blood pump 5703. The initial solution quantity is added directly to the recirculation bag 5721 at a desired ratio to RBC flow rate. No static mixer is used.

The process illustratively depicted in FIG. 58 is similar to that depicted in FIG. 56. The differences are the gravity drainage of thawed glycerolized RBCs directly into the recirculation bag 5822 and that the initial addition of solution is made directly into the recirculation bag 5822.

Example 3

Alternative Solutions for Use in Deglycerolization Processes

The current storage solutions generally contain both glucose and electrolytes such as sodium phosphate, sodium citrate and sodium chloride. They are prepared at pH 5.7 or thereabouts since autoclaving to sterilize the solutions causes caramelization of the glucose when both glucose and salts are present at a pH much above 6.2. The principal requirements for storage of RBCs after deglycerolization are hemolysis less than 1% and survival of transfused RBCs above 75% after 24 hours in human volunteers.

In order to obtain good refrigerated cell storage, the cells must be able to maintain metabolic processes. The presence of certain metabolites, such as glucose, phosphate and adenine has been shown to achieve this, but for maximum benefit, the pH should be in the physiological range of 7.0 or higher. Alkaline pH is not currently used in RBC storage solutions because of the obstacle of sterilization by heat, which at high pH caramelizes the glucose used in storage solution.

The present invention provides one answer to this problem, by providing an alkaline pH wash solution in two bags; one containing the glucose (e.g., hypertonic glucose in the range of 30% to 60%), and the other containing the electrolytes (e.g., an isotonic solution containing sodium phosphate and adenine plus any other solutes such as sodium citrate or NaCl necessary to provide the desired osmolality without exceeding concentrations unacceptable for transfusion). These may be combined at the time of use by the systems of various embodiments of the present invention. The pH of the electrolyte solution is basic (e.g., between about 7.0 and 9.0). Although entirely practical, this may require another solution bag in addition to the hypertonic solution, the wash solution and the additive.

In practice, the hypertonic solution is used "full strength" for the initial hypertonic dilution. The subsequent wash is created by mixing the two solutions to produce a wash solution of either a fixed osmolality or a series of different osmolalities or a continually changing osmolality in order to optimize the efficiency of the wash process. At the end of the wash, the wash solution contains the constituents present in the two solutions at concentrations and osmolality suitable to serve as a storage solution during subsequent refrigerated storage.

The goal of these approaches is to elevate the pH of the RBCs during both wash and post-wash storage, and to enable a more effective control of osmolality during the wash process. These approaches shorten the deglycerolization process; reduce hemolysis; permit longer refrigerated storage of deglycerolized RBCs; and, in some cases, may decrease the number and total volume of solutions needed.

Example 4

Intra-Operative Autotransfusion System

Use of the system of the present invention for intra-operative autotransfusion provides significant advantages over conventional autotransfusion systems, due, in large part, to the use of the CFC. Continuous flow centrifugation permits all fluid flow rates (e.g., blood, waste, saline) to be directly controlled. This results in the ability of the system of the present invention to respond immediately to changes in inlet hematocrit and to maintain a particular waste removal efficiency with an optimized setting of fluid flow rates as determined by the logic algorithm implemented by the microprocessor. The outlet hematocrit is maintained always at the desired level (i.e., about 50% to 55%), although this may be altered if medically desirable. The performance of a continuous flow system is not dependent on the quantity of blood in the reservoir to be processed. The current batch-processing centrifuge bowls process blood differently for a full bowl than for a partially-full bowl. There is frequently a partially-full bowl processed when the final amount of blood in the reservoir is processed. The control afforded by continuous flow centrifugation permits the entire process to be made automatic, from sensing the presence of blood in the reservoir to controlling fluid flow rates to achieve a fixed output blood hematocrit and a selected level of waste removal at any inlet hematocrit. The continuous flow process is also inherently faster than batch processing.

The CFC has a relatively small internal blood volume and, consequently, a much smaller size than a conventional centrifuge bowl. This reduces the amount of disposable plastic and associated cost. It also reduces the mass of plastic and fluid subjected to high centrifugal forces; decreasing both the probability and magnitude of centrifuge structural failures.

Figure 59:
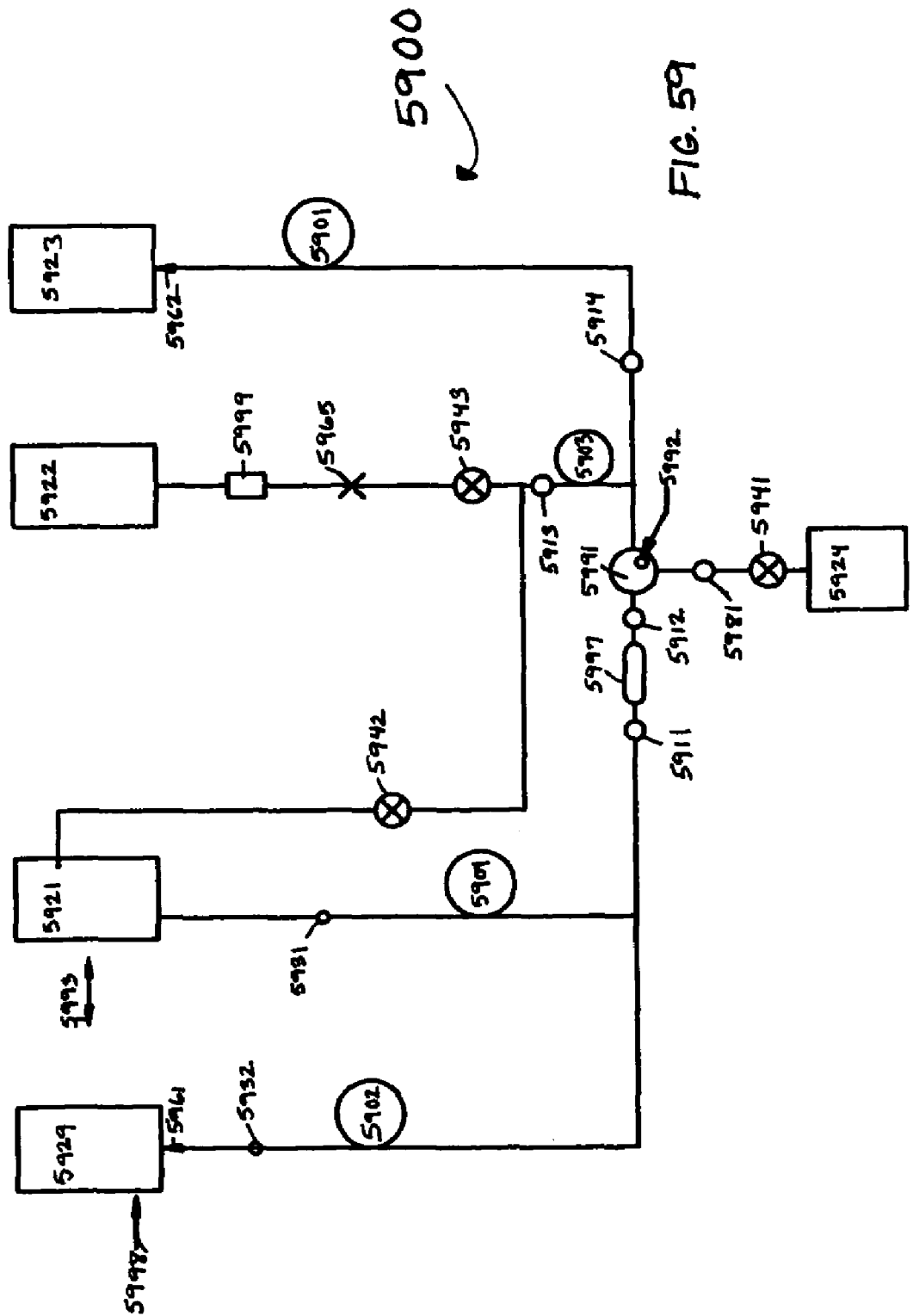
FIG. 59 is a schematic of a system to implement an intraoperative autotransfusion process, in accordance with an embodiment of the present invention.

An autotransfusion system 5900 utilizing the CFC 5991 of the present invention is illustratively depicted in FIG. 59. The system 5900 includes a recirculation bag 5921 with a blood filter, connected to a filtered blood reservoir 5929 with a level detector 5998, and a bag for washed RBCs 5922. A saline bag 5923 is additionally included in the system 5900. The bag of washed RBCs 5922 is connected to the system 5900 via a Luer lock fitting 5999, and the saline bag 5923 and filtered blood reservoir 5929 are connected with standard spikes 5962, 5961. A manual clamp 5965 is used when the washed RBC bag 5922 is disconnected from the system 5900. A mixer or shaker apparatus 5993 is included, to continually mix the contents of the recirculation bag 5921. A waste product bag 5924 is additionally included in the system 5900, along with a free plasma hemoglobin sensor 5981. A laminar flow element 5997 is included, as well.

A CFC 5991 is included, as described in greater detail above. In this embodiment of the present invention, the CFC 5991 separates washed RBCs from a waste product; thereby preparing the RBCs for reintroduction (i.e., transfusion) into a patient. An optical detector 5992 is included with the CFC 5991 to monitor the operation of the CFC 5991, as described above.

A saline pump 5901, filtered blood pump 5902, RBC pump 5903 and recirculation pump 5904 are included to pump the various fluids through the system 5900. Pressure measurement devices 5911, 5912, 5913, 5914 are included to monitor the flow of the various fluids through the tubing, and ultrasonic air sensors 5931, 5932 are further included to monitor the flow of air through the tubing (e.g., to determine when the fluid contents of a particular bag have been evacuated). A microprocessor or other, similar electronic device (not shown) collects the information from the pressure measurement devices 5911, 5912, 5913, 5914, ultrasonic air sensors 5931, 5932, free plasma hemoglobin sensor 5981 and optical detector 5992, and controls the valves 5941, 5942, 5943, pumps 5901, 5902, 5903, 5904 and CFC 5991, accordingly, to implement the autotransfusion process. Additionally, the bags and various other components of the system are connected to one another by tubing in communication with a cassette (not shown) designed specifically for the operation of this embodiment of the present invention, as discussed in greater detail above.

A separate disposable (e.g., standard suction wand, suction tubing and a blood or cardiotomy reservoir) is used to collect blood from the surgical field in any surgical procedure (e.g., cardiac, vascular, orthopedic and the like) where significant blood loss may occur. The blood reservoir 5929 may contain a blood filter and a defoamer. Blood is pumped from the blood reservoir 5929 to the CFC 5991 through a laminar flow tube 5997. A saline pump 5901 adds saline to wash the RBCs in the CFC 5991. A waste pump (not shown) may be included to remove waste fluid from the CFC 5991 to a waste bag. Output (i.e., washed) blood flows to the blood bag 5922. The presence of blood in the reservoir 5929 is sensed by starting the blood pump 5902. If blood is in the reservoir 5929, the blood 5902, saline 5901, and RBC pumps 5903 continue to operate until the reservoir is empty 5929. Air from the reservoir 5929 is detected by a standard ultrasonic air bubble detector 5932. This signal is used to turn off all pumps. The blood pump 5902 reverse-flows a few milliliters to push air out of the blood line back into the reservoir 5929. Then, the pumps start up in 15 seconds. If air is detected, the blood pump 5902 pumps the air back into the reservoir 5929 and the pumps stop. This process is repeated until blood is collected in the reservoir 5929, and pump operation resumes until the reservoir 5929 is empty.

Pressures are measured at the entrance 5911 and exit 5912 of the laminar flow tube 5997. The pressure drop across this tube 5997 is proportional to blood flow rate and to blood viscosity, which is a direct function of hematocrit. Viscosity is also temperature-dependent and the local temperature is measured and used in the logic algorithm to more accurately correlate viscosity with hematocrit. The fluid flow rates of the blood 5902, saline 5901 and RBC pumps 5903 are controlled by the algorithm to achieve the desired outlet blood hematocrit and the appropriate waste removal efficiency at any measured inlet blood hematocrit. Pressure is measured between the RBC pump 5903 and the washed RBC bag 5922 to alert the operator when the blood bag 5922 is full and should be replaced with another bag. Blood can flow from this blood bag 5922 directly to the patient while blood is being processed, or the blood bag 5922 can be removed and hung nearer the patient for gravity or pressure infusion. The recirculation wash process may be the same as that described in Example 2, above.

Example 5

Process for the Production of Leukoreduced Platelets from Pooled Buffy Coats

The system of the present invention may be used to pool buffy coats and separate platelet and white cell products from them. The platelet product may be leukoreduced. The objectives for this process are: to take multiple buffy coats produced, e.g., in an alternate embodiment of the present invention, and to combine or pool these buffy coats; to provide a single therapeutic dose of leukoreduced platelet product and an optional white cell product from pooled buffy coats; to achieve a high degree of and possibly adequate leukoreduction by centrifugal separation (e.g., with a small, low-cost leukofilter optionally added, if necessary to ensure consistent leukoreduction); to remove RBCs from the buffy coat by centrifugation; to achieve significant time and cost advantages by automating a process that is now only performed manually; and to eliminate the expensive leukofilter from this process entirely, or use a much smaller and less expensive one.

Figure 60:
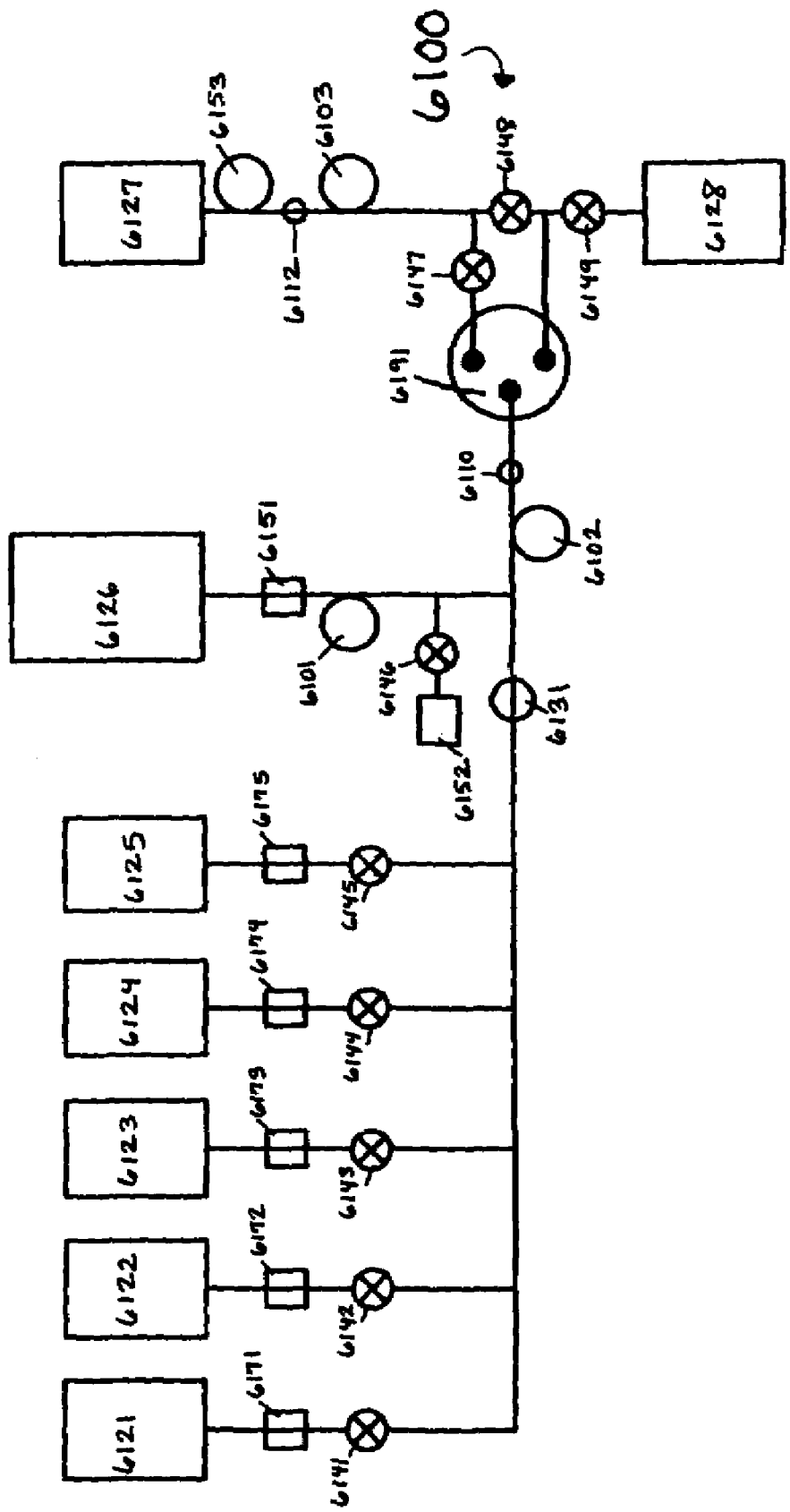
FIG. 60 is a schematic of a system to implement a process for the preparation of a therapeutic dose of leukoreduced platelets from pooled buffy coats, in accordance with an embodiment of the present invention.

A system 6100 for preparing leukoreduced platelets from pooled buffy coats is illustratively depicted in FIG. 60. The system includes at least one buffy coat bag 6121-6125; each connected to the system via a sterile dock 6171-6175, respectively. A Platelet Additive Solution (PAS) bag 6126 is also included, along with a bacterial filter 6151 to maintain sterility of the system 6100. An air vent filter 6152 is included, as well as a leukofilter 6153. A platelet product bag 6127 and white cell product 6128 bag collect the various blood products separated by continuous flow centrifugation.

A CFC 6191 is included, as described in greater detail above. In this embodiment of the present invention, the CFC 6191 separates the platelet product from the white cell product portion of the pooled buffy coats. An optical detector (not shown) is included with the CFC 6191 to monitor the operation of the CFC 6191, as described above.

A PAS pump 6101, cell pump 6102 and a platelet pump 6103 are included to pump the various fluids through the system 6100. Pressure measurement devices 6111, 6112 are included to monitor the flow of the various fluids through the tubing, and an ultrasonic air sensor 6131 is further included to monitor the flow of air through the tubing (e.g., to determine when the fluid contents of a particular bag have been evacuated). A microprocessor or other, similar electronic device (not shown) collects the information from the pressure measurement devices 6111, 6112, ultrasonic air sensor 6131 and optical detector (not shown), and controls the valves 6141-6149, pumps 6101, 6102, 6103 and CFC 6191, accordingly, to implement the process of this embodiment of the invention. Additionally, the bags and various other components of the system are connected to one another by tubing in communication with a cassette (not shown) designed specifically for the operation of this embodiment of the present invention, as discussed in greater detail above.

In operation, buffy coat bags 6121-6125 (up to about 5) are sterilely docked (e.g., via a Luer fitting 6171-6175, respectively) to the disposable set and a bag of PAS 6126 is attached (e.g., via standard spike or other connector) to the set. Solution sterility is maintained with a bacterial filter 6151. This disposable set cassette is inserted into the console, the door is closed, and the bags are hung on hangers on the console sides. The bar code on the cassette is read by the console to implement the leukoreduction from pooled buffy coat process. The user pushes the "Start" button and the complete process is thereafter automatic. At the end of the process, the platelet 6127 and white cell 6128 product bags are sealed off and removed from the set. The disposable set is then discarded.

The process includes the following: provide platelet storage solution to each buffy coat bag (in addition to the approximately 20 mL of plasma in each bag from a blood separation process); pump buffy coat into white cells and any contaminating RBCs at the periphery, platelets at a smaller radius and solution at radii smaller than the platelet layer; and remove white and red cells from the CFC 6191 to a white cell product bag 6128 and simultaneously pump platelets and PAS through a leukofilter 6153 to a platelet product bag 6127. The process also includes: rinsing each buffy coat bag 6121-6125 with PAS after the bag is emptied; emptying the bags 6121-6125 again; and centrifuging the fluid to separate and remove to product bags 6127, 6128 the residual platelets, leukocytes and RBCs. The process may additionally include a purge of the leukofilter 6153 with PAS to remove a percentage of trapped platelets.

It will be readily apparent to one of skill in the art that the various process steps and methods of the above-described embodiments of the present invention can be combined to make additional process alternatives without departing from the main concepts of the invention. It will be evident that other processes could be implemented using the basic console and cassette design. The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A system for deglycerolizing red blood cells ("RBCs"), comprising:
   a recirculation bag; and
   a continuous flow centrifuge ("CFC") to separate a waste product from fluid containing RBCs, said CFC in fluid communication with said recirculation bag by a first tubing segment, said first tubing segment terminating at its first end at said CFC, and terminating at its second end at said recirculation bag;
   a blood pump to pump fluid containing RBCs from said recirculation bag to said CFC, said blood pump configured on said first tubing segment;
   a first valve to control the flow of fluid into said recirculation bag, said first valve configured on a second tubing segment, said second tubing segment terminating at its first end at said CFC, and terminating at its second end at said recirculation bag;
   a deglycerolized RBC bag to contain deglycerolized RBCs, said deglycerolized RBC bag in fluid communication with said second tubing segment by a third tubing segment, said third tubing segment terminating at its first end at said deglycerolized RBC bag, and terminating at its second end at a first junction with said second tubing segment, said first junction configured on said second tubing segment between said CFC and said first valve;
   a second valve to control the flow of fluid into said deglycerolized RBC bag, said second valve configured on said third tubing segment; and
   a cassette through which said first, second and third tubing segments pass.

2. The system of claim 1, further comprising an optical sensor to detect a position of an interface within said CFC.

3. The system of claim 1, further comprising a recirculation bag shaker to shake said recirculation bag, and wherein said recirculation bag further includes a blood filter to eliminate particulates, clots and white cell agglomerates that form during operation of said system.

4. The system of claim 1, further comprising a free plasma hemoglobin sensor to detect hemoglobin in said waste product.

5. The system of claim 1, further comprising a console that houses said cassette.

6. The system of claim 1, further comprising:
   a RBC pump to pump fluid from which waste product has been removed by said CFC from said CFC, said RBC pump configured on said second tubing segment between said CFC and said first junction;
   a third valve to control the flow of fluid from said CFC, said third valve configured on said second tubing segment between said CFC and said RBC pump;
   a waste product bag to contain waste product separated with said CFC, said waste product bag in fluid communication with said CFC by a fourth tubing segment, said fourth tubing segment terminating at its first end at said waste product bag, and terminating at its second end at said CFC; and a fourth valve to control the flow of fluid to said waste product bag, said fourth valve configured on said fourth tubing segment between said CFC and said waste product bag.

7. The system of claim 6, further comprising:

a first pressure measurement device to detect the flow of fluid from said blood pump to said CFC through said first tubing segment, said first pressure measurement device configured along said first tubing segment between said blood pump and said CFC;

a second pressure measurement device to detect the flow of fluid from which waste product has been removed by said CFC through said second tubing segment, said second pressure measurement device configured along said second tubing segment between said CFC and said RBC pump;

a third pressure measurement device to detect the flow of fluid from said RBC pump through said second tubing segment, said third pressure measurement device configured along said second tubing segment between said RBC pump and said first junction; and a first ultrasonic sensor to detect air in said first tubing segment, said first ultrasonic sensor configured along said first tubing segment between said recirculation bag and said blood pump.

8. The system of claim 1, further comprising:

a glycerolized RBC bag to contain glycerolized RBCs, said glycerolized RBC bag in fluid communication with said second tubing segment by a fifth tubing segment, said fifth tubing segment terminating at its first end at said glycerolized RBC bag, and terminating at its second end at said first junction with said second tubing segment, wherein said glycerolized RBC bag is attached to said fifth tubing segment by a sterile dock;

a thawed RBC pump to pump glycerolized RBCs from said glycerolized RBC bag, said thawed RBC pump configured on said fifth tubing segment between said glycerolized RBC bag and said first junction;

a second ultrasonic sensor to detect air in said fifth tubing segment, said second ultrasonic sensor configured along said fifth tubing segment between said glycerolized RBC bag and said thawed RBC pump;

a static mixer to combine said glycerolized RBCs with a solution, said static mixer configured on said fifth tubing segment between said thawed RBC pump and said first junction; and a fifth valve to control the flow of fluid from said static mixer, said fifth valve configured on said fifth tubing segment between said static mixer and said first junction.

9. The system of claim 8, further comprising:

a first solution bag to contain a first solution, said first solution bag connected with a spike to a first end of a first solution tubing segment, and said first solution tubing segment terminating at its second end to a solution junction on a sixth tubing segment;

a first solution valve to control the flow of said first solution from said first solution bag, said first solution valve configured on said first solution tubing segment;

a second solution bag to contain a second solution, said second solution bag connected with a spike to a first end of a second solution tubing segment, and said second solution tubing segment terminating at its second end to a first solution tubing segment junction on said first solution tubing segment, said first solution tubing segment junction configured on said first solution tubing segment between said first solution valve and said solution junction;

a second solution valve to control the flow of said second solution from said second solution bag, said second solution valve configured on said second solution tubing segment;

a third solution bag to contain a third solution, said third solution bag connected with a spike to a first end of said sixth tubing segment, said sixth tubing segment terminating at its second end at a second junction configured on said fifth tubing segment between said thawed RBC pump and said static mixer;

a third solution valve to control the flow of said third solution from said third solution bag, said third solution valve configured on said sixth tubing segment between said third solution bag and said solution junction;

a solution pump to pump a solution from a solution bag, said solution pump configured on said sixth tubing segment between said solution junction and said second junction;

a third ultrasonic sensor to detect air in said sixth tubing segment, said third ultrasonic sensor configured along said sixth tubing segment between said solution junction and said solution pump;

a first bacterial filter to maintain sterility of said system, said first bacterial filter configured on said sixth tubing segment between said solution pump and said second junction;

a second bacterial filter to maintain sterility of said system, said second bacterial filter configured on a seventh tubing segment, said seventh tubing segment terminating at its first end at a third junction on said sixth tubing segment between said solution pump and said first bacterial filter, and terminating at its second end at a fourth junction on said second tubing segment between said CFC and said first junction; and a solution pressure measurement device to detect the flow of a solution from said solution pump through said seventh tubing segment, said solution pressure measurement device configured along said seventh tubing segment between said third junction and said second bacterial filter.

10. The system of claim 9, wherein said first solution is a hypertonic solution, said second solution is an isotonic solution, and said third solution is a wash solution.

11. The system of claim 9, further comprising:

a sixth valve to control the flow of a solution through said seventh tubing segment, said sixth valve configured on said seventh tubing segment between said second bacterial filter and said fourth junction;

a seventh valve to control the flow of fluid from which waste product has been removed by said CFC through said second tubing segment, said seventh valve configured on said second tubing segment between said second CFC and said fourth junction;

a fourth pressure measurement device to detect the flow of fluid from said blood pump to said CFC through said first tubing segment, said fourth pressure measurement device configured along said first tubing segment between said RBC pump and said CFC;

a fifth pressure measurement device to detect the flow of fluid from which waste product has been removed by said CFC through said second tubing segment, said second pressure measurement device configured along said second tubing segment between said CFC and said fourth junction;

a sixth pressure measurement device to detect the flow of fluid through said second tubing segment, said sixth pressure measurement device configured along said second tubing segment between said first junction and said fourth junction;

a third ultrasonic sensor to detect air in said first tubing segment, said third ultrasonic sensor configured along said first tubing segment between said recirculation pump and said blood pump; and a waste product bag to contain waste product separated with said CFC, said waste product bag in fluid communication with said CFC by a waste product tubing segment, said waste product tubing segment terminating at its first end at said waste product bag, and terminating at its second end at said CFC; and a waste pump to pump a waste product from said CFC, said waste pump configured on said waste product tubing segment between said CFC and said waste product bag.

12. The system of claim 1, further comprising:

a first solution bag to contain a first solution, said first solution bag connected with a spike to a first end of a first solution tubing segment, and said first solution tubing segment terminating at its second end to a solution junction on an eighth tubing segment;

a first solution pump to pump said first solution from said first solution bag, said first solution pump configured on said first solution tubing segment;

a second solution bag to contain a second solution, said second solution bag connected with a spike to a first end of said eighth tubing segment, said eighth tubing segment terminating at its second end at either said first junction or a fifth junction with said second tubing segment, said fifth junction configured between said CFC and said first junction;

a second solution pump to pump a solution from a solution bag, said second solution pump configured on said eighth solution tubing segment between said second solution bag and said solution junction;

a bacterial filter to maintain sterility of said system, said bacterial filter configured on said eighth tubing segment between said solution junction and said and said eighth tubing segment junction;

a fourth ultrasonic sensor to detect air in said first solution tubing segment, said fourth ultrasonic sensor configured along said first solution tubing segment between said first solution bag and said first solution pump;

a fifth ultrasonic sensor to detect air in said eighth tubing segment, said fifth ultrasonic sensor configured along said eighth solution tubing segment between said second solution bag and said second solution pump; and a solution pressure measurement device to detect the flow of a solution through said eighth tubing segment, said solution pressure measurement device configured along said eighth tubing segment between said solution junction and said bacterial filter.

13. The system of claim 12, wherein said eighth tubing segment terminates at its second end at said fifth junction, said system further comprising:

a glycerolized RBC bag to contain glycerolized RBCs, said glycerolized RBC bag in fluid communication with said eighth tubing segment by a glycerolized tubing segment, said glycerolized tubing segment terminating at its first end at said glycerolized RBC bag, and terminating at its second end at a glycerolized junction with said eighth tubing segment between said fifth junction and said bacterial filter, wherein said glycerolized RBC bag is attached to said glycerolized tubing segment by a sterile dock;

a glycerolized valve to control the flow of glycerolized RBCs from said glycerolized RBC bag, said glycerolized valve configured on said glycerolized tubing segment;

a sixth ultrasonic sensor to detect air in said glycerolized tubing segment, said sixth ultrasonic sensor configured along said glycerolized tubing segment between said glycerolized valve and said glycerolized junction; and a static mixer to combine said glycerolized RBCs with a solution, said static mixer configured on said eighth tubing segment between said glycerolized junction and said fifth junction.

14. The system of claim 13, further comprising:

a third solution bag to contain a third solution, said third solution bag connected with a spike to a first end of a third solution tubing segment, said third solution tubing segment terminating at its second end at a third solution junction on said eighth tubing segment, said third solution junction configured on said eighth tubing segment between said second solution bag and said fifth ultrasonic sensor;

a third solution valve to control the flow of said third solution from said third solution bag, said third solution valve configured on said third solution tubing segment; and a second solution valve to control the flow of said second solution from said second solution bag, said second solution valve configured on said eighth tubing segment between said second solution bag and said third solution junction.

15. The system of claim 12, wherein said eighth tubing segment terminates at its second end at said fifth junction, said system further comprising:

a glycerolized RBC bag to contain glycerolized RBCs, said glycerolized RBC bag in fluid communication with said first tubing segment by a glycerolized tubing segment, said glycerolized tubing segment terminating at its first end at said glycerolized RBC bag, and terminating at its second end at a glycerolized junction with said first tubing segment between said blood pump and said CFC, wherein said glycerolized RBC bag is attached to said glycerolized tubing segment by a sterile dock;

a glycerolized valve to control the flow of glycerolized RBCs from said glycerolized RBC bag, said glycerolized valve configured on said glycerolized tubing segment;

an eighth valve to control the flow of fluid into said CFC, said eighth valve configured on said first tubing segment between said glycerolized junction and said CFC;

an ninth valve to control the flow of fluid from said CFC, said ninth valve configured on said second tubing segment between said CFC and said fifth junction;

a seventh pressure measurement device to detect the flow of fluid into said CFC through said first tubing segment, said seventh pressure measurement device configured along said first tubing segment between said glycerolized junction and said CFC;

an eighth pressure measurement device to detect the flow of fluid from which waste product has been removed by said CFC through said second tubing segment, said eighth pressure measurement device configured along said second tubing segment between said CFC and said fifth junction;

a waste product bag to contain waste product separated with said CFC, said waste product bag in fluid communication with said CFC by a waste product tubing segment, said waste product tubing segment terminating at its first end at said waste product bag, and terminating at its second end at said CFC;

a waste pump to pump a waste product from said CFC, said waste pump configured on said waste product tubing segment between said CFC and said waste product bag; and a ninth pressure measurement device to detect the flow of waste product from said waste pump through said waste product tubing segment, said ninth pressure measurement device configured along said waste product tubing segment between said waste product pump and said waste product bag.

16. The system of claim 1, further comprising:

a glycerolized RBC bag to contain glycerolized RBCs, said glycerolized RBC bag in fluid communication with said recirculation bag with a glycerolized tubing segment, said glycerolized tubing segment terminating at its first end at said glycerolized RBC bag, and terminating at its second end at said recirculation bag, wherein said glycerolized RBC bag is attached to said glycerolized tubing segment by a sterile dock;

a glycerolized valve to control the flow of glycerolized RBCs from said glycerolized RBC bag to said recirculation bag, said glycerolized valve configured on said glycerolized tubing segment;

a glycerolized ultrasonic sensor to detect air in said glycerolized tubing segment, said glycerolized ultrasonic sensor configured along said glycerolized tubing segment between said glycerolized valve and said glycerolized RBC bag; and a RBC pump to pump fluid from which waste product has been removed by said CFC from said CFC, said RBC pump configured on said second tubing segment between said CFC and said first junction.

17. A method of deglycerolizing red blood cells ("RBCs"), comprising:

providing a RBC deglycerolizing system, including
a continuous flow centrifuge ("CFC") adapted to separate deglycerolized RBCs from a waste product,
a glycerolized RBC bag containing thawed, glycerolized RBCs,
at least two solution bags containing at least one solution,
a recirculation bag, said recirculation bag in fluid communication with said glycerolized RBC bag, said at least two solution bags, said CFC and a deglycerolized RBC bag by way of tubing, and
a cassette through which said tubing passes;

configuring said deglycerolizing system with a console including electronic and mechanical components to operate said deglycerolizing system; and operating said deglycerolizing system to deglycerolize RBCs.

* * * * *